(12) United States Patent
Wang et al.

(10) Patent No.: US 7,417,181 B2
(45) Date of Patent: Aug. 26, 2008

(54) PLANTS WITH INCREASED PHOSPHOROUS UPTAKE

(75) Inventors: Zeng-Yu Wang, Ardmore, OK (US); Maria Harrison, Ardmore, OK (US); Kai Xiao, Hebei Province (CN)

(73) Assignee: The Samuel Roberts Noble Foundation, Ardmore, OK (US)

( * ) Notice: Subject to any disclaimer, the term of this patent is extended or adjusted under 35 U.S.C. 154(b) by 202 days.

(21) Appl. No.: 11/400,802

(22) Filed: Apr. 7, 2006

(65) Prior Publication Data
US 2006/0240537 A1 Oct. 26, 2006

Related U.S. Application Data

(60) Provisional application No. 60/669,242, filed on Apr. 7, 2005, provisional application No. 60/669,275, filed on Apr. 7, 2005.

(51) Int. Cl.
*A01H 5/00* (2006.01)
*C12N 5/14* (2006.01)
*C12N 15/63* (2006.01)
*C07H 21/00* (2006.01)

(52) U.S. Cl. .................. 800/295; 435/419; 435/320.1; 536/23.6

(58) Field of Classification Search ........................ None
See application file for complete search history.

(56) References Cited

U.S. PATENT DOCUMENTS

2004/0031072 A1* 2/2004 La Rosa et al. ............. 800/278

FOREIGN PATENT DOCUMENTS

WO WO 99/20746 4/1999

OTHER PUBLICATIONS

Database EMBL, Database accession o. AJ511832, Nov. 11, 2002 (abstract).
Durmus et al., "Cloning and comparative protein modeling of two purple acid phosphatase isozymes from sweet potatoes (*Ipomoea batatas*)," *Biochimica et Biophysica Acta*, 1434:202-209, 1999.
Liu et al., "Cloning and characterization of two phosphate transporters from *Medicago truncatula* roots: Regulation in response to phosphate and to colonization by arbuscular mycorrhizal (AM) fungi," *Molecular Plant- Microbe Interactions*, 11:14-22, 1998.
Schenk et al., "Binuclear metal centers in plant purple acid phosphatases: Fe-Mn in sweet potato and Fe-Zn in soybean," *Arch Biochem. Biophys.*, 370:183-189, 1999.
Xiao et al., "Cloning and characterization of a novel purple acid phosphatase gene(MtPAP1) from *Medicago truncatula* Barrel Medic," *J. Integrative Plant Biol.*, 48:204-211, 2006.
Xiao et al., "Improved phosphorus acquisition and biomass production in Arabidopsis by transgenic expression of a purple acid phosphatase gene from *M. trunatula*," *Plant Science*, 170:191-202, 2006.
Asmar et al., "Barley genotypes differ in activity of soluble extracellular phosphatase and depletion of organic phosphorus in the rhizosphere soil," *Plant Soil*, 172:117-122, 1995.
Baldwin et al., "LEPS2, a phosphorus starvation-induced novel acid phosphatase from tomato," *Plant Physiol.*, 125:728-737, 2001.
del Pozo et al., "A type 5 aicd phosphatase gene from *Arabidopsis thaliana* is induced by phosphate starvation and by some other types of phosphate mobilising/oxidative stress conditions," *Plant J.*, 19:579-589, 1999.
Duff et al., "The role of acid phosphatases in plant phosphorus metabolism," *Physiol. Plant.*, 90:791-800, 1994.
Gilbert et al., "Acid phosphatase activity in phosphorus-deficient white lupin roots," *Plant Cell Environ.*, 22:801-810, 1999.
Goldstein et al., "Phosphate Starvation Inducible Metabolism in *Lycopersicon esculentum*: I. Excretion of Acid Phosphatase by Tomato Plants and Suspension-Cultured Cells," *Plant Physiol.*, 87:711-715, 1988.
Goldstein et al., "Phosphate Starvation Inducible Metabolism in *Lycopersicon esculentum*: II. Characterization of the Phosphate Starvation Inducible-Excreted Acid Phosphatase," *Plant Physiol.*, 87:716-720, 1988.
Haran et al., "Characterization of Arabidopsis acid phosphatase promoter and regulation of acid phosphatase expression," *Plant Physiol.*, 124:615-626, 2000.
Hegeman and Grabau, "A novel phytase with sequence similarity to purple acid phosphatases is expressed in cotyledons of germinating soybean seedlings," *Plant Physiol.*, 126:1598-1605, 2001.
Helal, "Varietal differences in root phosphatase activity as related to the utilization of organic phosphatase," *Plant Soil*, 123:161-163, 1990.
Hunter et al., "Comparison of acid phosphatases in two genotypes of white clover with different responses to applied phosphate," *J. Plant Nutr.*, 22:679-692, 1999.
Li et al., "Purple acid phosphatases of *Arabidopsis thaliana*. Comparative analysis and differential regulation by phosphate deprivation," *J. Biol. Chem.*, 277:27772-27781, 2002.
Li et al., "Secretion of active recombinant phytase from soybean cell-suspension cultures," *Plant Physiol.*, 114:1103-1111, 1997.
McLachlan, "Acid phosphatase activity of intact roots and phophorus nutrition in plants. II Variations among wheat roots," *Aust. J. Agric. Res.*, 31:441-448, 1980.
Miller et al., "Molecular control of acid phosphatase secretion into the rhizosphere of proteoid roots from phosphorus-stressed white lupin," *Plant Physiol.*, 127:594-606, 2001.

(Continued)

*Primary Examiner*—Phuong T. Bui
*Assistant Examiner*—Vinod Kumar
(74) *Attorney, Agent, or Firm*—Sonnenschein Nath & Rosenthal LLP

(57) ABSTRACT

The invention provides plant acid phosphatase coding sequences. Also provided are constructs comprising these sequences, plants transformed therewith and methods of use thereof. In certain aspects of the invention, transgenic plants are provided exhibiting improved phosphorous utilization.

18 Claims, 11 Drawing Sheets

OTHER PUBLICATIONS

Nakazato et al., "The glycosylphosphatidylinositol-anchored phosphatase from *Spirodela oligorrhiza* is a purple acid phosphatase," *Plant Physiol.*, 118:1015-1020, 1998.

Richardson et al., "Extracellular secretion of *Aspergillus phytase* from Arabidopsis roots enables plants to obtain phosphorus from phytate," *Plant J.*, 25:641-649, 2001.

Schenk et al., "Identification of mammalian-like purple acid phosphatases in a wide range of plants," *Gene*, 250:117-125, 2000.

Tarafdar et al., "Organic phosphorus compounds as a phosphorus source for higher plants through the activity of phosphatases produced by plant roots and microorganisms," *Biol. Fertil. Soils*, 5:308-312, 1988.

Tomscha et al., "Phosphatase under-producer mutants have altered phosphorus relations," *Plant Physiol.*, 135:334-345, 2004.

Vance et al., "Phosphorus acquisition and use: critical adaptation by plants for securing a nonrenewable resource," *New Phytol.*, 157:423-447, 2003.

Wasaki et al., "Secreted acid phosphatase is expressed in cluster roots of lupin in response to phosphorus deficiency," *Plant Soil*, 248:129-136, 2003.

Wasaki et al., "Structure of a cDNA for an acid phosphatase from phosphate-deficient lupin (*Lupinus albus* L.) roots," *Soil Sci. Plant Nutr.*, 45:439-449, 1999.

Wasaki et al., "Secreting portion of acid phosphatase in roots of lupin (*Lupinus albus* L.) and a key signal for the secretion from the roots," *Soil Sci. Plant Nutr.*, 45:937-945, 1999.

Wasaki et al., "Molecular cloning and root specific expression of secretory acid phosphatase from phosphate deficient lupin (*Lupinus albus* L.)," *Soil Sci. Plant Nutr.*, 46:427-437, 2000.

Whitelaw, "Growth promotion of plants inoculated with phosphate-solubilizing fungi," *Advances in Agronomy*, 69:99-151, 2000.

Xiao et al., "Isolation and characterization of root-specific phosphate transporter promoters from *Medicago truncatula*," *Plant Biol.*, 8:1-11, 2006.

Yan et al., "Induction of a major leaf acid phosphatase does not confer adaptation to low phosphorus availability in common bean," *Plant Physiol.*, 125:1901-1911, 2001.

Yu et al., "Extraction of apoplastic sap from plant roots by centrifugation," *New Phytol.*, 143:299-304, 1999.

Zimmermann et al., "Engineering the root-soil interface via targeted expression of a synthetic phytase gene in trichoblasts," *Plant Biotechnol. J.*, 1:353-360, 2003.

Zimmermann, "Differential expression of three purple acid phosphatases from potato," *Plant Biol.*, 6:519-528, 2004.

* cited by examiner

FIG. 1A-B

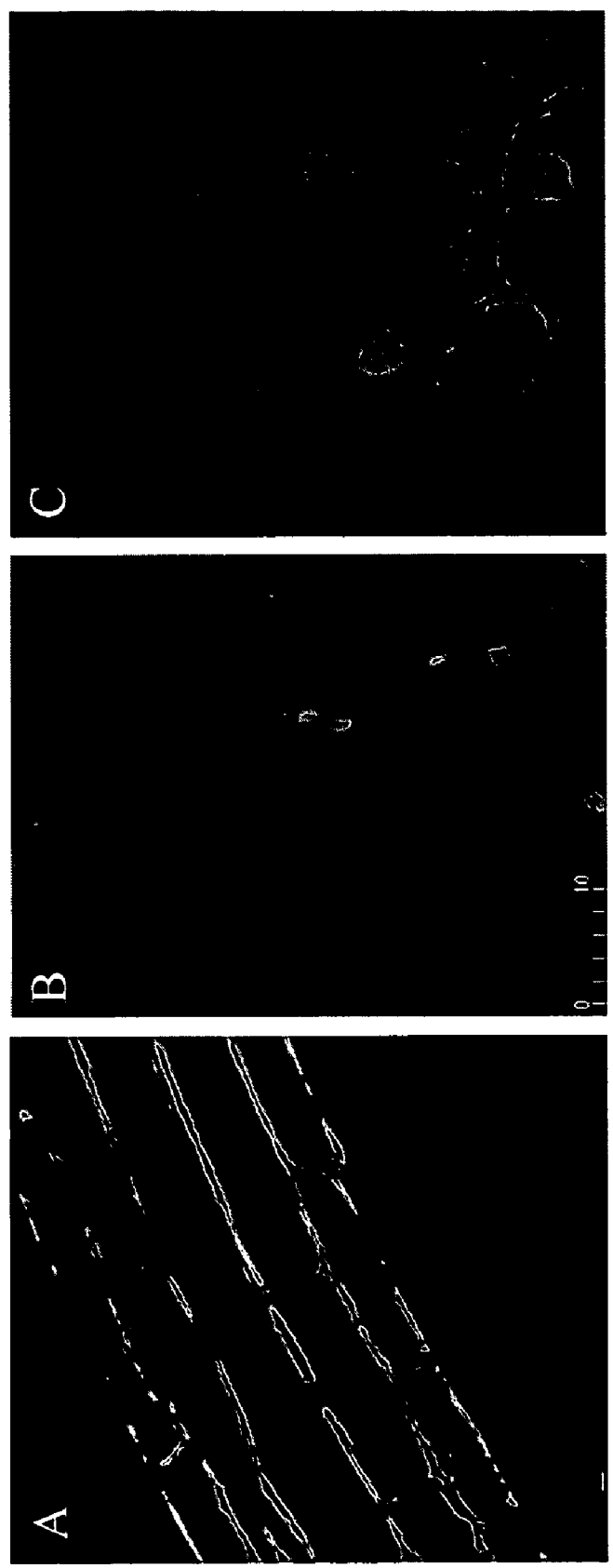
FIG. 3A-C

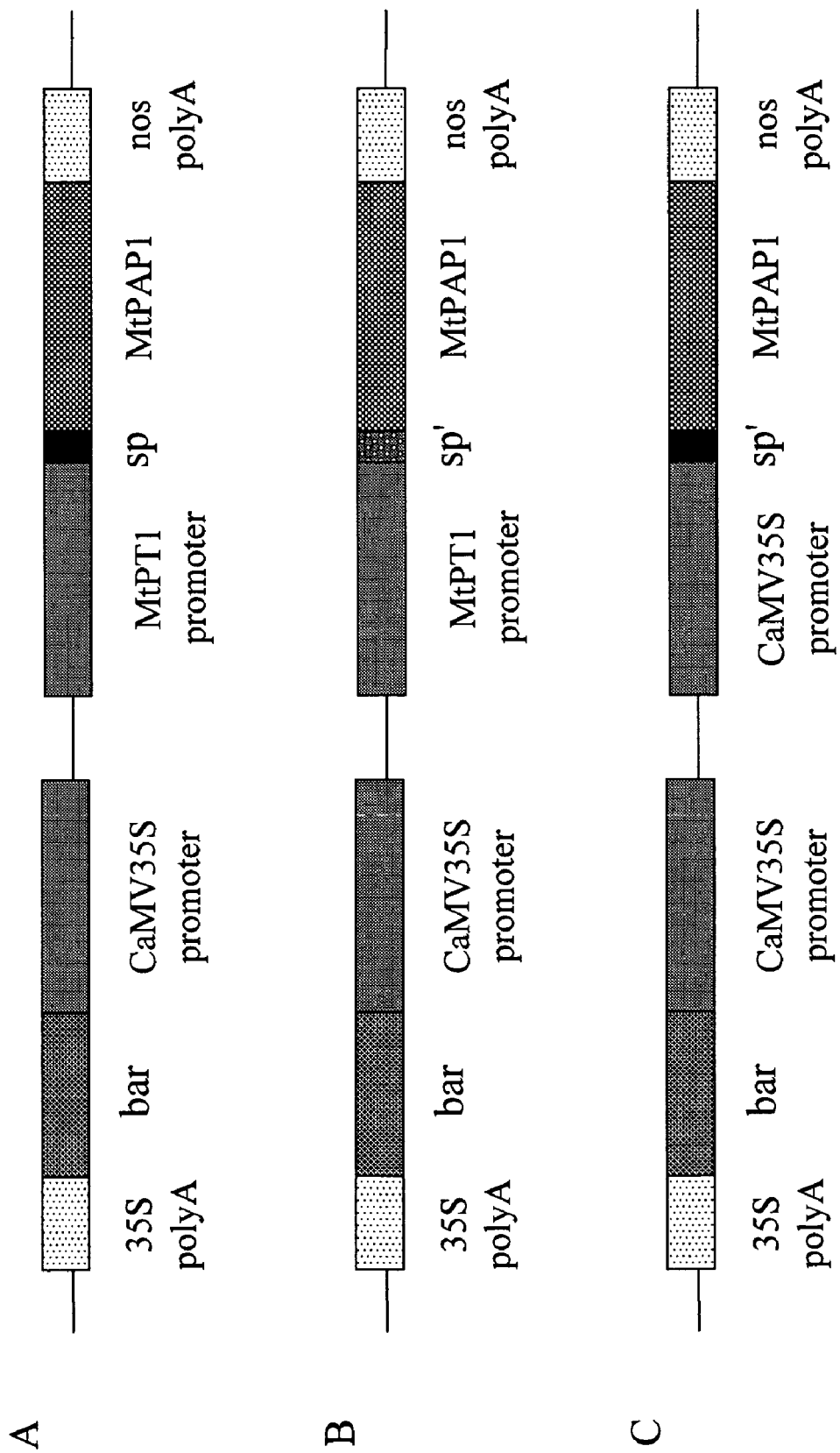
FIG. 4A-C

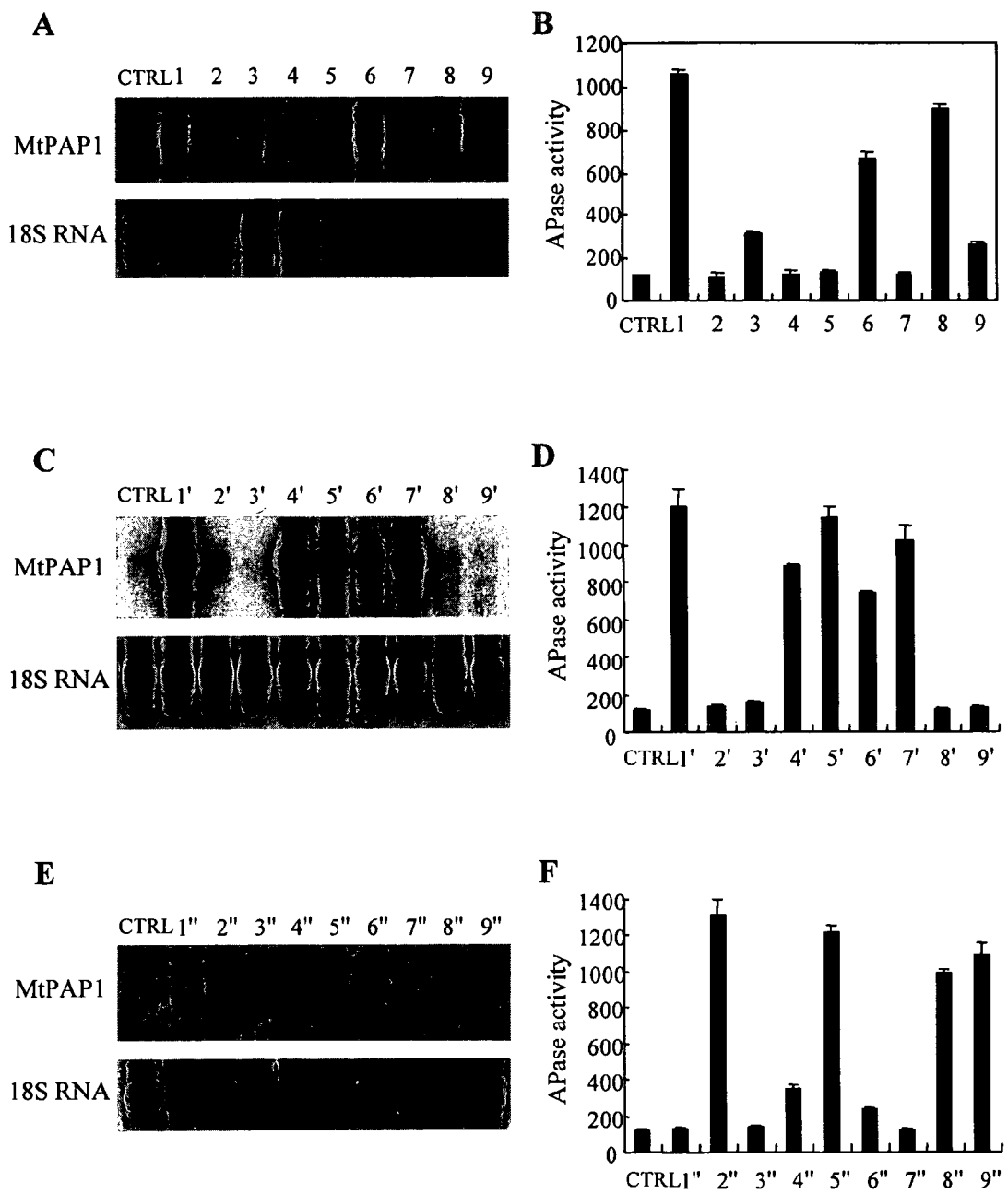
FIG. 5A-F

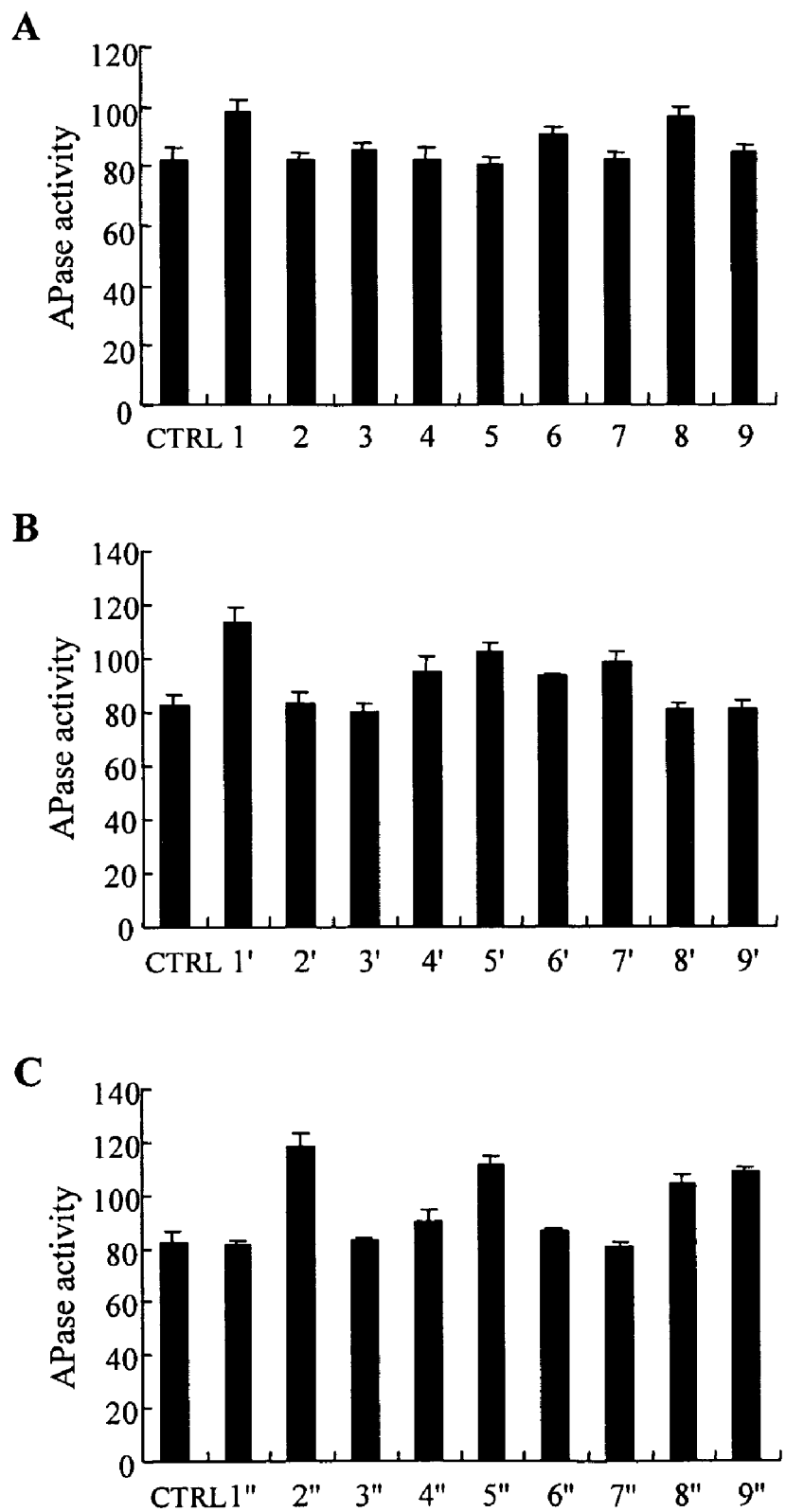
FIG. 6A-C

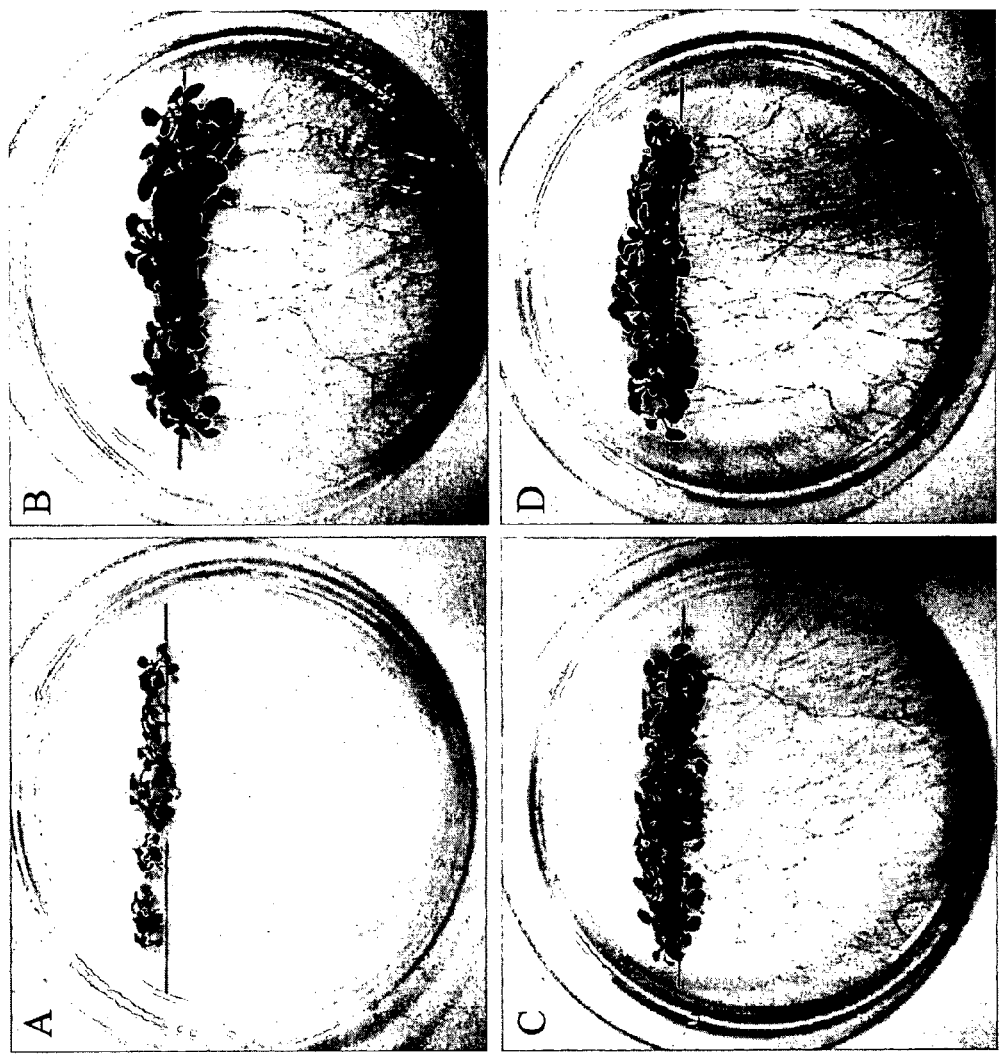
FIG. 7A-D

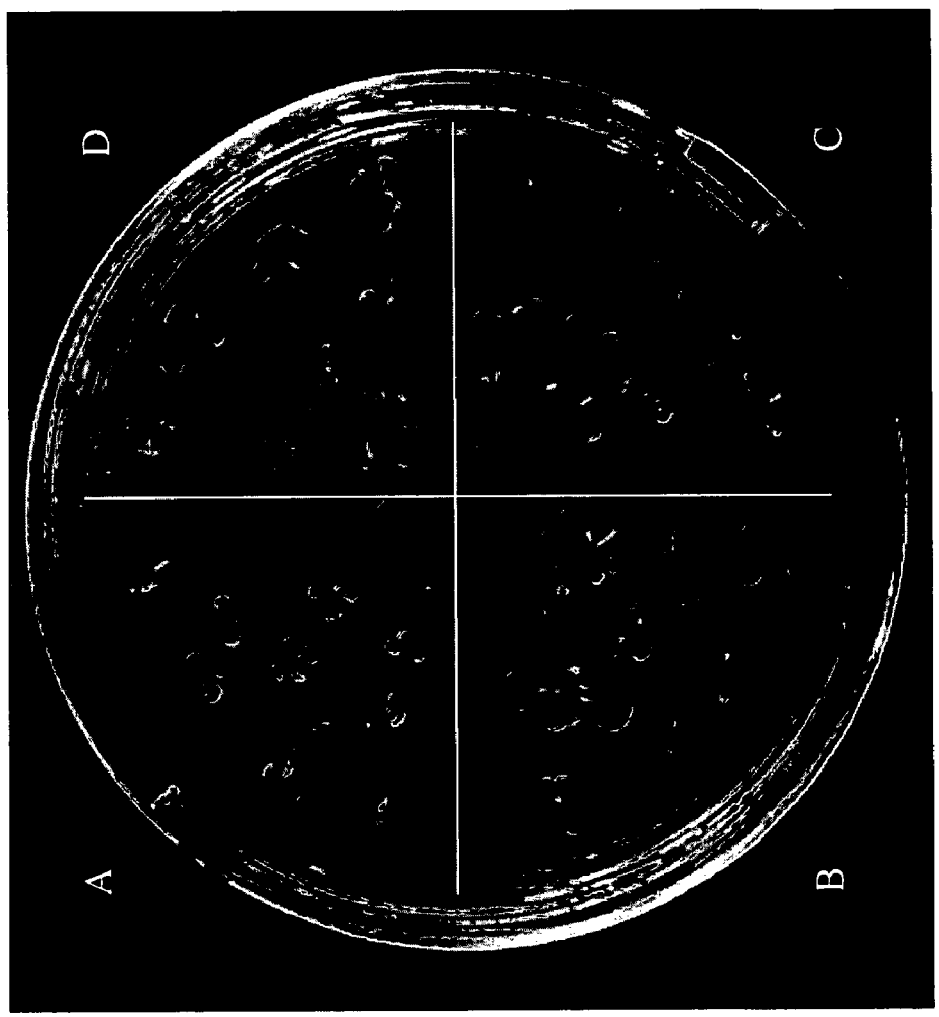
FIG. 8A-D

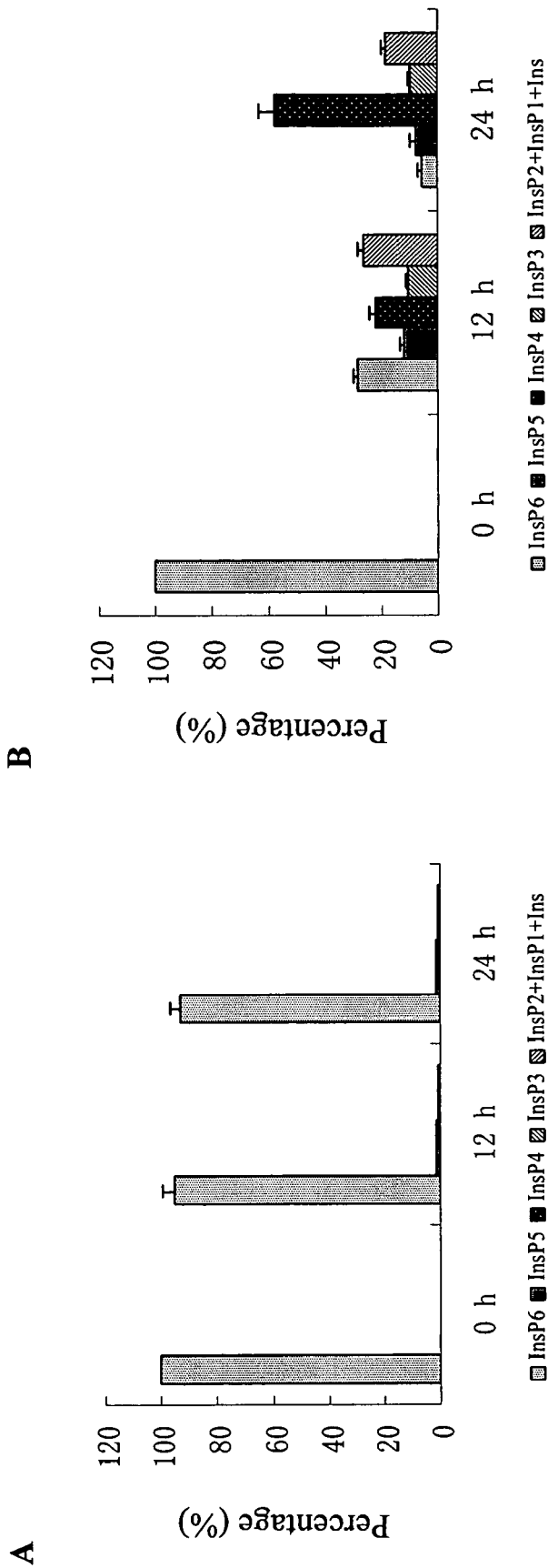
FIG. 9A-B

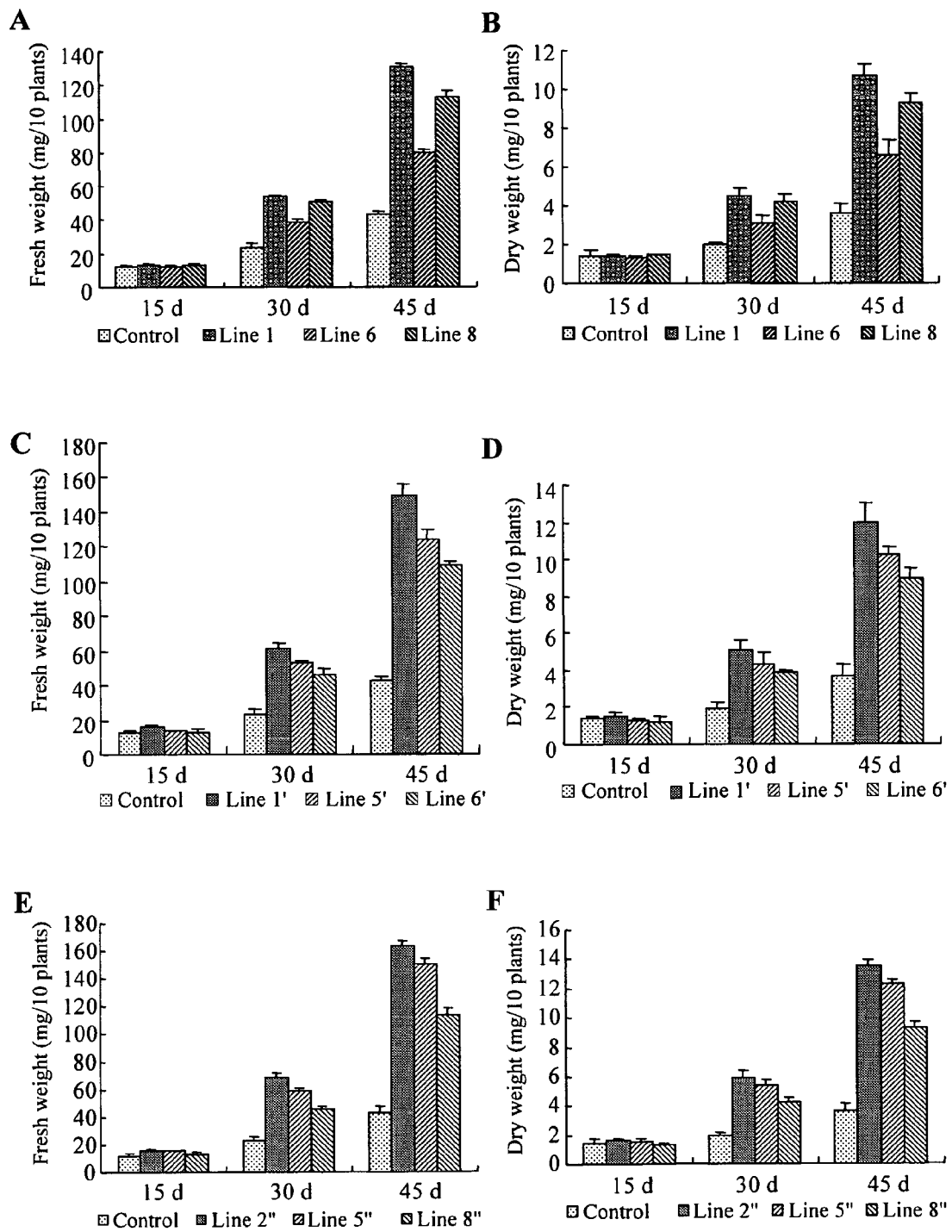
FIG. 10A-F

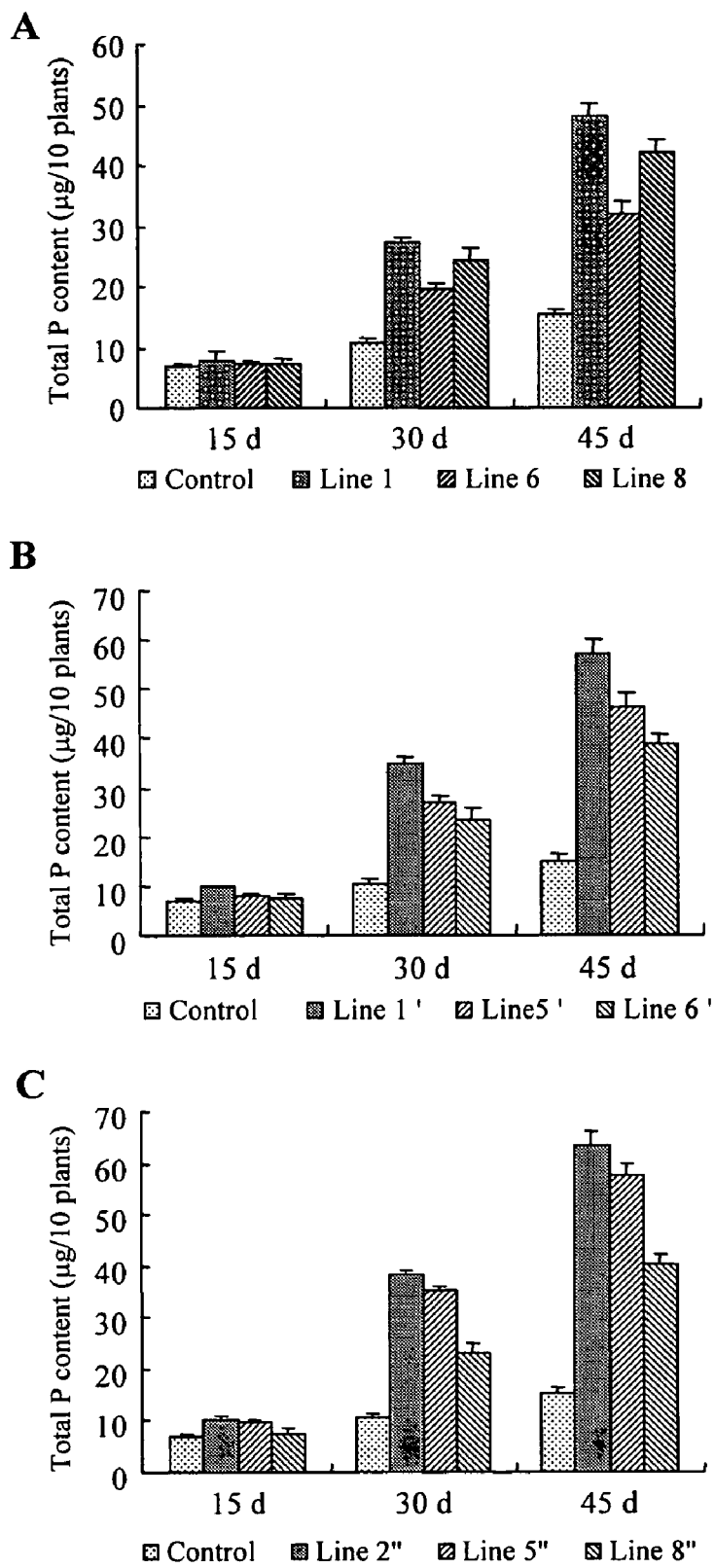
FIG. 11A-C

```
                           SEQUENCE LISTING

<160> NUMBER OF SEQ ID NOS: 51

<210> SEQ ID NO 1
<211> LENGTH: 1698
<212> TYPE: DNA
<213> ORGANISM: Medicago truncatula

<400> SEQUENCE: 1
ctgcaggctc aaaagggtct ttgagttttg aagaaaaatg ggttttcttc atagtttatt      60
attagcttta tgtttggttt tgaatttggt gtttgtgtgt aatggaggca gaactagtac     120
ttttgttagg aaagttgaga agaccattga tatgccactt gatagtgatg ttttgatgt      180 tccttctggt tataatgctc cccaacaggt tcatataaca caaggtgatc atgtggggaa     240
agcagtgatc gtatcgtggg tgactgagga tgaaccaggc tcgaacgcag tgcgttactg     300
gagtaagaac agcaagcaga agaggctagc taaagggaaa attgttactt atagattttt     360
caattacact tctggtttta tccatcacac tactattagg aatttagagt acaataccaa     420
atattattac gaggttggac tcgggaacac aacaaggcag ttttggttta caactcctcc     480
tgaaatcggt cctgatgtgc catacacatt tggtctaata ggggatcttg gtcagagcta     540
tgattcaaac aagacacttt ctcactacga attgaaccca acaaaaggac aaacagtgtt     600
gtttgttgga gatctctcat atgcagataa ctacccgaat catgacaatg ttaggtggga     660
tacttgggga agatttgcag aaaggagcgt tgcttatcaa ccgtggatat ggactgttgg     720
aaaccatgaa cttgatttg ctccagaaat tggagaaaca aaaccattca agccttactc     780
gcaccgatac cgtactcctt acaaagcatc gcaaagtacc tcgcccttt ggtattctat      840 caagagagct tcagctcaca tcattgtgtt ggcttcatat tcagcatatg gaaaatatac      900
accacaatac aaatggcttg aacaggagct accaaaagtt aacaggacag aaactccttg     960
gttgattgtt ctcatgcatt caccttggta taatagctac aattatcatt acatggaagg    1020
ggaatcaatg agagtaatgt atgagccatg gtttgttaag tacaaggttg atgtcgtgta    1080
tgctggccat gtccacgcct atgaacgttc tgaacgtgtg tccaatgttg catataatgt    1140
tgtaaatggt atttgcactc ctataaaaga tcaatcagct cctgtataca taaccattgg    1200
agatggaggg aaccttgaag gcttagcaac caacatgaca gaaccacaac cagagtactc    1260
agcatacaga gaggccagct ttggacatgc catttttgac ataaagaaca gaacacatgc    1320
tcactacagc tggcatagga atcaagatgg ttactctgtt gaggctgatt ctcattggtt    1380
cttcaacaga ttttggcacc cagttgatga ttccacaact catgtttccc attaacacgt    1440
tgatgttaag caataaagtc atatgattat gtaattattg tttgtgggtc aataccacca    1500
acaattatga ttatcataat cattacctt cattttactt tgtatcactg ttatataact     1560
gcaaaggaag aagtttcatt tgtaatttgt aattttcttt ttgttgtaat aactatatag    1620
atgcagatag gaaccccaaa atgaaatcct atacctcaga cctatggctc ctaaaaaaaa    1680
aaaaaaaaaa aaaaaaaa                                                  1698

<210> SEQ ID NO 2
<211> LENGTH: 465
```

-continued

```
<212> TYPE: PRT
<213> ORGANISM: Medicago truncatula

<400> SEQUENCE: 2

Met Gly Phe Leu His Ser Leu Leu Ala Leu Cys Leu Val Leu Asn
 1               5                  10                  15

Leu Val Phe Val Cys Asn Gly Gly Arg Thr Ser Thr Phe Val Arg Lys
             20                  25                  30

Val Glu Lys Thr Ile Asp Met Pro Leu Asp Ser Asp Val Phe Asp Val
         35                  40                  45

Pro Ser Gly Tyr Asn Ala Pro Gln Gln Val His Ile Thr Gln Gly Asp
     50                  55                  60

His Val Gly Lys Ala Val Ile Val Ser Trp Val Thr Glu Asp Glu Pro
 65                  70                  75                  80

Gly Ser Asn Ala Val Arg Tyr Trp Ser Lys Asn Ser Lys Gln Lys Arg
                 85                  90                  95

Leu Ala Lys Gly Lys Ile Val Thr Tyr Arg Phe Phe Asn Tyr Thr Ser
             100                 105                 110

Gly Phe Ile His His Thr Thr Ile Arg Asn Leu Glu Tyr Asn Thr Lys
         115                 120                 125

Tyr Tyr Tyr Glu Val Gly Leu Gly Asn Thr Thr Arg Gln Phe Trp Phe
     130                 135                 140

Thr Thr Pro Pro Glu Ile Gly Pro Asp Val Pro Tyr Thr Phe Gly Leu
145                 150                 155                 160

Ile Gly Asp Leu Gly Gln Ser Tyr Asp Ser Asn Lys Thr Leu Ser His
                 165                 170                 175

Tyr Glu Leu Asn Pro Thr Lys Gly Gln Thr Val Leu Phe Val Gly Asp
             180                 185                 190

Leu Ser Tyr Ala Asp Asn Tyr Pro Asn His Asp Asn Val Arg Trp Asp
         195                 200                 205

Thr Trp Gly Arg Phe Ala Glu Arg Ser Val Ala Tyr Gln Pro Trp Ile
     210                 215                 220

Trp Thr Val Gly Asn His Glu Leu Asp Phe Ala Pro Glu Ile Gly Glu
225                 230                 235                 240

Thr Lys Pro Phe Lys Pro Tyr Ser His Arg Tyr Arg Thr Pro Tyr Lys
                 245                 250                 255

Ala Ser Gln Ser Thr Ser Pro Phe Trp Tyr Ser Ile Lys Arg Ala Ser
             260                 265                 270

Ala His Ile Ile Val Leu Ala Ser Tyr Ser Ala Tyr Gly Lys Tyr Thr
         275                 280                 285

Pro Gln Tyr Lys Trp Leu Glu Gln Glu Leu Pro Lys Val Asn Arg Thr
     290                 295                 300

Glu Thr Pro Trp Leu Ile Val Leu Met His Ser Pro Trp Tyr Asn Ser
305                 310                 315                 320

Tyr Asn Tyr His Tyr Met Glu Gly Glu Ser Met Arg Val Met Tyr Glu
                 325                 330                 335

Pro Trp Phe Val Lys Tyr Lys Val Asp Val Val Tyr Ala Gly His Val
             340                 345                 350

His Ala Tyr Glu Arg Ser Glu Arg Val Ser Asn Val Ala Tyr Asn Val
         355                 360                 365

Val Asn Gly Ile Cys Thr Pro Ile Lys Asp Gln Ser Ala Pro Val Tyr
     370                 375                 380

Ile Thr Ile Gly Asp Gly Gly Asn Leu Glu Gly Leu Ala Thr Asn Met
385                 390                 395                 400
```

```
Thr Glu Pro Gln Pro Glu Tyr Ser Ala Tyr Arg Glu Ala Ser Phe Gly
                405                 410                 415

His Ala Ile Phe Asp Ile Lys Asn Arg Thr His Ala His Tyr Ser Trp
            420                 425                 430

His Arg Asn Gln Asp Gly Tyr Ser Val Glu Ala Asp Ser His Trp Phe
        435                 440                 445

Phe Asn Arg Phe Trp His Pro Val Asp Ser Thr Thr His Val Ser
    450                 455                 460

His
465

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 3

Gly Asp Leu Gly
  1

<210> SEQ ID NO 4
<211> LENGTH: 5
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 4

Gly Asp Leu Ser Tyr
  1               5

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 5

Gly Asn His Glu
  1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Val Leu Met His
  1

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
```

-continued

Peptide

<400> SEQUENCE: 7

Gly His Val His
 1

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
tgtcgacatg ggttttcttc atag                                              24

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 9
tccatgggat gggaaacatg agttgt                                            26

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 10
agtcgacatg gcaactacta aat                                               23

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 11
agtcgaccgt agcacatgtt gaa                                               23

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 12
tgtcgacggc agaactagta cttt                                              24

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Synthetic Primer

<400> SEQUENCE: 13
tccatgggat gggaaacatg agttgt                                              26

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 14
aggatcctat tatatgcatg ggctg                                               25

<210> SEQ ID NO 15
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 15
tccatggact gaatttgtta cctagt                                              26

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 16
gccatgggtt ttcttcatag ttta                                                24

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 17
aggttaccat tgttggtggt attga                                               25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 18
tccatggcaa ctactaaatc tttt                                                24

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      Primer

```
<400> SEQUENCE: 19
tccatgggcg tagcacatgt tgaact                                              26

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 20
tccatgggca gaactagtac ttt                                                 23

<210> SEQ ID NO 21
<211> LENGTH: 25
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 21
aggttaccat tgttggtggt attga                                               25

<210> SEQ ID NO 22
<211> LENGTH: 1533
<212> TYPE: DNA
<213> ORGANISM: Medicago truncatula

<400> SEQUENCE: 22
gctggagttc gaatcccgaa cacccccactt ctccacattt aaaatgtgtg aactcaagtc         60
actatgttat tgaccaaaaa aacaaaatg agaaaaaaaa agaccaagcg gggaaaagta         120
cccatttacc aagtcgatac aaatactaat tgacttttat tttttggtta aaaataataa        180
ttgacttttt ttaggggaaa taataataat tgacattttt tttttaatat ttttgacaaa        240
aaattgactt tatgtaccga ttataattat cataaaccca cataatataa cgtcatagtt        300
taattgacag ttggtctgaa acaaaatata gtttaacttg ttagtttttt tagaggagtt        360
aaattgccag ttggttgcat tgcataatat ggcgcatgca cgagttgata tatactattt        420
gatttgataa gagtatacga tacttgtacg ttttgtactt gtgatatatt atgttattgc        480
ggaatatttt atgaaaaaat ttatggttga cattcaaact aaaatgttta cttaatggta        540
gagttataaa cctcgggtcc gcgtaagcat agctcagttg gcagagacat gcattattat        600
atgtaggggc tggggttcaa accccggaca ccccacttat tcatcttgaa aaatatgaat        660
tctaaccact aaattacttg accaaaataa cccaaaatcc tgatgtagga gatcctctga        720
ttaatgtata attttttgaaa gaatgtataa catatagttg aatattaggt tgcaacagat        780
acaaggggta ttaaatatat tgagcatatc ctcaagtgga atcaatgtca aatctgaaat        840
atcgtttaat ttccttaacg gatgtcctat attttcatt ggttatgtct atgtattaag         900
aatatattac ttaaaaacta taaattaatt agagtccaac ttaaaatttt attaagttac        960
aaaaaatagt gcttgtgaag cgttgacatt ggtgaatgct tatgattaat taggcatata       1020
ccccattgat gctaaattga ttctttttga ctttggatgc attcctgatt tggctaggat       1080
tgttacctat atatagctga gtttgattat ctgctcacag tgtgcataaa cctagcttct       1140
cataccactt tacttcttta tcaacttggc ttcttgcaag aggtacgaac tctatctatc       1200
```

```
tcccttattg agtttgtaga caccaaatga gtattcatgt tgtacatttt tttttggcaa    1260
atcttggtcg catcatacaa ctgtagagat taatggctcg agataactaa gatatattta    1320
aagagtttag tactcgagtg tatgtgtgta taaaaatata tataattttc attggtatta    1380
ggcacaattt aggtaggtta ctttatagtt ttgagcagtt tatccatttc ttacctcagc    1440
ctcacaaatg tcaagttagt ttttttttg tttactaata tttaatgtgt cttgtgctta    1500
attatgcagg gaaaaactag gtaacaaatt cag                                 1533

<210> SEQ ID NO 23
<211> LENGTH: 1238
<212> TYPE: DNA
<213> ORGANISM: Medicago truncatula

<400> SEQUENCE: 23
ccacttgtct ttatttttta agggcaggga ccaccttgtt atttgcttaa aattgaacga     60
aaatattaag attatagtct ctttaggatt acttaaaaaa tcaacaagca aactatgaat    120
ggataattta tgatatagca taatagaaac tattatacaa acccagaatt ttgttattgg    180
agaacctcta actaccagta tagttgaata ttggggttgca acagatacaa ggggtattaa    240
atatattgag catatatctg tttccacaag tggaatcaat gtcaaatcta aaaatatct    300 cttaattacc ttaagtggaa tggatgtcct agatttttaa ttggttatgt atctgtatta    360
aggatatatt actcggaaag aataaattag catgtgaact attatagttc cctaaaaaaa    420
aaagtcaact attatagtgg ttttcctcta aaaagagag taattacac ttcgctttcc     480 ttacagatgt ttgaattact gttccatctc ctcttatatt aaaatataca ttttattctc    540
ctcttattca aaacatatta tgctaaaaaa aaatctatt agggattttg aatcgttgaa    600
caacataatt gttttactta agtcttaagg tgtttaaatc tctttaggtc aacatcccga    660
aattatgctt aagcatgttt aaatttgtga ttaatgaaat tactttggtg attagctagt    720
gaatttcaac tcttgatata tccaatagca attgccgcaa aagttgtata aatttagttg    780
tacaaatatc atttatctat aatacatttt tcattcctaa ttttatatca aataaacatg    840
gttggatgca agtgatttac atgtgtttcc tattatttat ttacatttt tattacaatg    900 atgtatgtgt ttctgttaat gttgaatgct tagggtatcc aagtttaatc attaattaac    960
ataactagca ttcagattta agaaacaaga aaattaatta aaaaaaaaat agtgcttata   1020
aagcgtttac attgatgaat gcttgtgagt ggtgattagg ttaggcatat accattgatg   1080
ctgaattgat tcctttgacc tagcaaggtt catgttacct atatatatgc atattaatag   1140
tttagctgct caaagtgcag gcacctagct agctcctcat acaaacttga cttctcacaa   1200
ggaggtcttc tctctctcta tctctctagc ttggggac                           1238

<210> SEQ ID NO 24
<211> LENGTH: 1705
<212> TYPE: DNA
<213> ORGANISM: Medicago truncatula

<400> SEQUENCE: 24
gtgatctgca ggtgcagctt gacaaccgac taggttagaa tatcacattg accttatcac     60
ttatatagtg tacctaagat aaataaatgc gacattactg ttacttaata tccaacaata   120
taaacagggt ggattcgaat cctaaccgct gcttactttt ctgcaaccaa aaataggtaa    180
acttgctctg ttgcaatcag ataaaaattg caagacatct aacccttata ttttatatcg    240
tcaacttaca aaaataagta acaagaattg tttggacgaa acgactttcc ttttggatac    300
```

-continued

```
gatactctac ttatcagttt attacttgtt aaacgatttg gtacactggc gacattcgac      360
catcatagag ctctagcgtc gacacgatta tgagttagcc tcaatctggt ttttgctatg      420
ttttgttagt ttctgtttat ttgcatttgt ttttattttg ttcagtggag atgaagatgg      480
gtggtggctt tgtttcggct atgtgatttg gtatgaaaat cttgaatctg attttctgaa      540
ttaatgatat gggttcttta tttagggtgt gttctgttg gatgcatatc tcgattcaac       600
atgactgctt ttatcctaat gttgcttgaa agggttagtt gcgtagatgc cccgtgttga      660
tggtagtagt cgttcatcgt acctaaagta ttttatccac cgtggtttct ttttgtatca      720
ttggtggaca atgatatatt tatattgttt gttcatcact cgatgtgcga tgaaatttca      780
agatcactac gactctgtga attcagttag taggtggttg atttgcctcg aaaccgtgtt      840
tatggcaaat gaccaataca tctatttaaa tgcttagaat attcattttg cgttttttt       900 gcaattccgt ttcgcccaca tatgtaggtt cgccagattt tccatgctag tggttgtcta      960
gagttagttc tcttttatta ccacttttgt accgacttta tttacggatt aattatcatc     1020
ataaacccac ataatataat gtcatagttt gattgtcatt gctcgatatg gcgcatgcac     1080
aagttgatat actatttgac gagtgtttgg ttggtacttg tacgttttgt acttgtgata     1140
tattattgtg taatagttta tgaaaaattt tatggttgac attccaacta aaaaatttac     1200
ttaatggtag agttatacaa acccaaaatc ttgatgtcgg agatcctcaa attaatgtac     1260
atatagttga atattaggtt gcaacagata caaggggtat taaatatatt gagcatatcc     1320
tcaagtggaa tcaatgtcaa atctgaaata tcgtttaatt tccctaagta gaatggatgt     1380
cctagatttt taattggtca tgtctatgta ttaagtatat attacttaaa aagtataaat     1440
taattagagc ccgttgctgc tagaaactgc aaatttaaa caaaaatagt gcttgtgaag      1500
ggttgacatt gatgaatgtt tatgattaat gaggcatata ccccattgat gctaaattga     1560 ttcttttaa ctcatgaggc ataccctggct tggctgggat tgttacgtat atatatagct      1620
gagtttaatt atctgctcac agtgtgcata aacctaactc cttataccac tttacttctt     1680
tatcaacttg gtttcttgca aggag                                           1705
```

<210> SEQ ID NO 25
<211> LENGTH: 464
<212> TYPE: PRT
<213> ORGANISM: Glycine max

<400> SEQUENCE: 25

```
Met Gly Val Val Glu Gly Leu Leu Ala Leu Ala Leu Val Leu Ser Ala
  1               5                  10                  15

Cys Val Met Cys Asn Gly Gly Ser Ser Ser Pro Phe Ile Arg Lys Val
                 20                  25                  30

Glu Lys Thr Val Asp Met Pro Leu Asp Ser Asp Val Phe Ala Val Pro
             35                  40                  45

Pro Gly Tyr Asn Ala Pro Gln Gln Val His Ile Thr Gln Gly Asp Leu
         50                  55                  60

Val Gly Lys Ala Val Ile Val Ser Trp Val Thr Val Asp Glu Pro Gly
     65                  70                  75                  80

Ser Ser Glu Val His Tyr Trp Ser Glu Asn Ser Asp Lys Lys Lys Ile
                 85                  90                  95

Ala Glu Gly Lys Leu Val Thr Tyr Arg Phe Phe Asn Tyr Ser Ser Gly
                100                 105                 110

Phe Ile His His Thr Thr Ile Arg Asn Leu Glu Tyr Lys Thr Lys Tyr
```

```
                115                 120                 125
Tyr Tyr Glu Val Gly Leu Gly Asn Thr Thr Arg Gln Phe Trp Phe Val
    130                 135                 140

Thr Pro Pro Glu Ile Gly Pro Asp Val Pro Tyr Thr Phe Gly Leu Ile
145                 150                 155                 160

Gly Asp Leu Gly Gln Ser Phe Asp Ser Asn Lys Thr Leu Ser His Tyr
                165                 170                 175

Glu Leu Asn Pro Arg Lys Gly Gln Thr Val Leu Phe Val Gly Asp Leu
            180                 185                 190

Ser Tyr Ala Asp Asn Tyr Pro Asn His Asp Asn Ile Arg Trp Asp Ser
        195                 200                 205

Trp Gly Arg Phe Thr Glu Arg Ser Val Ala Tyr Gln Pro Trp Ile Trp
    210                 215                 220

Thr Ala Gly Asn His Glu Asn His Phe Ala Pro Glu Ile Gly Glu Thr
225                 230                 235                 240

Val Pro Phe Lys Pro Tyr Thr His Arg Tyr His Val Pro Tyr Lys Ala
                245                 250                 255

Ser Gln Ser Thr Ser Pro Phe Trp Tyr Ser Ile Lys Arg Ala Ser Ala
            260                 265                 270

His Ile Ile Val Leu Ala Ser Tyr Ser Ala Tyr Gly Lys Tyr Thr Pro
        275                 280                 285

Gln Tyr Lys Trp Leu Glu Lys Glu Leu Pro Lys Val Asn Arg Thr Glu
    290                 295                 300

Thr Pro Trp Leu Ile Val Leu Met His Ser Pro Trp Tyr Asn Ser Tyr
305                 310                 315                 320

Asn Tyr His Tyr Met Glu Gly Glu Thr Met Arg Val Met Tyr Glu Pro
                325                 330                 335

Trp Phe Val Gln Tyr Lys Val Asp Val Val Phe Ala Gly His Val His
            340                 345                 350

Ala Tyr Glu Arg Ser Glu Arg Val Ser Asn Val Ala Tyr Asn Ile Val
        355                 360                 365

Asn Gly Leu Cys Ala Pro Val Asn Asp Lys Ser Ala Pro Val Tyr Ile
    370                 375                 380

Thr Ile Gly Asp Gly Gly Thr Leu Glu Gly Leu Ala Thr Asn Met Thr
385                 390                 395                 400

Glu Pro Gln Pro Lys Tyr Ser Ala Phe Arg Glu Ala Ser Phe Gly His
                405                 410                 415

Ala Ile Phe Asp Ile Thr Asn Arg Thr His Ala His Tyr Ser Trp His
            420                 425                 430

Arg Asn Gln Asp Gly Val Ala Val Glu Ala Asp Ser Leu Trp Ser Phe
        435                 440                 445

Asn Arg Tyr Trp His Pro Val Asp Asp Ser Thr Ala His Val Ser His
    450                 455                 460

<210> SEQ ID NO 26
<211> LENGTH: 465
<212> TYPE: PRT
<213> ORGANISM: Ipomoea batatas

<400> SEQUENCE: 26

Met Gly Ala Ser Arg Thr Gly Cys Tyr Leu Leu Ala Val Val Leu Ala
1               5                   10                  15

Ala Val Met Asn Ala Ala Ile Ala Gly Ile Thr Ser Ser Phe Ile Arg
            20                  25                  30
```

```
Lys Val Glu Lys Thr Val Asp Met Pro Leu Asp Ser Asp Val Phe Arg
            35                  40                  45

Val Pro Pro Gly Tyr Asn Ala Pro Gln Gln Val His Ile Thr Gln Gly
         50                  55                  60

Asp His Val Gly Lys Ala Met Ile Val Ser Trp Val Thr Val Asp Glu
 65                  70                  75                  80

Pro Gly Ser Ser Lys Val Val Tyr Trp Ser Glu Asn Ser Gln His Lys
                 85                  90                  95

Lys Val Ala Lys Gly Asn Ile Arg Thr Tyr Thr Tyr Phe Asn Tyr Thr
            100                 105                 110

Ser Gly Tyr Ile His His Cys Thr Ile Arg Asn Leu Glu Tyr Asn Thr
        115                 120                 125

Lys Tyr Tyr Tyr Glu Val Gly Ile Gly Asn Thr Thr Arg Ser Phe Trp
    130                 135                 140

Phe Thr Thr Pro Pro Glu Val Gly Pro Asp Val Pro Tyr Thr Phe Gly
145                 150                 155                 160

Leu Ile Gly Asp Leu Gly Gln Ser Phe Asp Ser Asn Arg Thr Leu Thr
                165                 170                 175

His Tyr Glu Arg Asn Pro Ile Lys Gly Gln Ala Val Leu Phe Val Gly
            180                 185                 190

Asp Leu Ser Tyr Ala Asp Asn Tyr Pro Asn His Asp Asn Val Arg Trp
        195                 200                 205

Asp Thr Trp Gly Arg Phe Val Glu Arg Ser Thr Ala Tyr Gln Pro Trp
    210                 215                 220

Ile Trp Thr Ala Gly Asn His Glu Ile Asp Phe Ala Pro Glu Ile Gly
225                 230                 235                 240

Glu Thr Lys Pro Phe Lys Pro Phe Thr Lys Arg Tyr His Val Pro Tyr
                245                 250                 255

Lys Ala Ser Gly Ser Thr Glu Thr Phe Trp Tyr Ser Ile Lys Arg Ala
            260                 265                 270

Ser Ala Tyr Ile Ile Val Leu Ser Ser Tyr Ser Ala Tyr Gly Lys Tyr
        275                 280                 285

Thr Pro Gln Tyr Lys Trp Leu Glu Glu Glu Leu Pro Lys Val Asn Arg
    290                 295                 300

Thr Glu Thr Pro Trp Leu Ile Val Leu Met His Ser Pro Trp Tyr Asn
305                 310                 315                 320

Ser Tyr Asn Tyr His Tyr Met Glu Gly Glu Thr Met Arg Val Met Tyr
                325                 330                 335

Glu Pro Trp Phe Val Gln His Lys Val Asp Leu Val Phe Ala Gly His
            340                 345                 350

Val His Ala Tyr Glu Arg Ser Glu Arg Ile Ser Asn Val Ala Tyr Asn
        355                 360                 365

Ile Val Asn Gly Glu Cys Thr Pro Val Arg Asp Gln Ser Ala Pro Val
    370                 375                 380

Tyr Ile Thr Ile Gly Asp Gly Gly Asn Leu Glu Gly Leu Ala Thr Asn
385                 390                 395                 400

Met Thr Asp Pro Gln Pro Glu Tyr Ser Ala Phe Arg Glu Ala Ser Phe
                405                 410                 415

Gly His Ala Thr Leu Asp Ile Lys Asn Arg Thr His Ala Tyr Tyr Ser
            420                 425                 430

Trp His Arg Asn Gln Asp Gly Tyr Ala Val Glu Ala Asp Ser Met Trp
        435                 440                 445

Val Ser Asn Arg Phe Trp His Pro Val Asp Asp Ser Thr Thr Thr Lys
```

```
                     450                 455                 460

Leu
465

<210> SEQ ID NO 27
<211> LENGTH: 465
<212> TYPE: PRT
<213> ORGANISM: Ipomoea batatas

<400> SEQUENCE: 27

Met Gly Ala Ser Arg Thr Gly Cys Tyr Leu Leu Ala Val Val Leu Ala
 1               5                  10                  15

Ala Val Met Asn Ala Ala Ile Ala Gly Ile Thr Ser Ser Phe Ile Arg
                20                  25                  30

Lys Val Glu Lys Thr Val Asp Met Pro Leu Asp Ser Asp Val Phe Arg
            35                  40                  45

Val Pro Pro Gly Tyr Asn Ala Pro Gln Gln Val His Ile Thr Gln Gly
        50                  55                  60

Asp His Val Gly Lys Ala Met Ile Val Ser Trp Val Thr Val Asp Glu
 65                  70                  75                  80

Pro Gly Ser Ser Lys Val Val Tyr Trp Ser Glu Asn Ser Gln His Lys
                85                  90                  95

Lys Val Ala Arg Gly Asn Ile Arg Thr Tyr Thr Tyr Phe Asn Tyr Thr
            100                 105                 110

Ser Gly Tyr Ile His His Cys Thr Ile Arg Asn Leu Glu Tyr Asn Thr
        115                 120                 125

Lys Tyr Tyr Tyr Glu Val Gly Ile Gly Asn Thr Thr Arg Ser Phe Trp
130                 135                 140

Phe Thr Thr Pro Pro Glu Val Gly Pro Asp Val Pro Tyr Thr Phe Gly
145                 150                 155                 160

Leu Ile Gly Asp Leu Gly Gln Ser Phe Asp Ser Asn Arg Thr Leu Thr
                165                 170                 175

His Tyr Glu Arg Asn Pro Ile Lys Gly Gln Ala Val Leu Phe Val Gly
            180                 185                 190

Asp Leu Ser Tyr Ala Asp Asn Tyr Pro Asn His Asp Asn Val Arg Trp
        195                 200                 205

Asp Thr Trp Gly Arg Phe Val Glu Arg Ser Thr Ala Tyr Gln Pro Trp
    210                 215                 220

Ile Trp Thr Ala Gly Asn His Glu Ile Asp Phe Ala Pro Glu Ile Gly
225                 230                 235                 240

Glu Thr Lys Pro Phe Lys Pro Phe Thr Lys Arg Tyr His Val Pro Tyr
                245                 250                 255

Lys Ala Ser Gly Ser Thr Glu Thr Phe Trp Tyr Pro Ile Lys Arg Ala
            260                 265                 270

Ser Ala Tyr Ile Ile Val Leu Ser Ser Tyr Ser Ala Tyr Gly Lys Tyr
        275                 280                 285

Thr Pro Gln Tyr Lys Trp Leu Glu Glu Glu Leu Pro Lys Val Asn Arg
    290                 295                 300

Thr Glu Thr Pro Trp Leu Ile Val Leu Met His Ser Pro Trp Tyr Asn
305                 310                 315                 320

Ser Tyr Asn Tyr His Tyr Met Glu Gly Glu Thr Met Arg Val Met Tyr
                325                 330                 335

Glu Pro Trp Phe Val Gln His Lys Val Asp Leu Val Phe Ala Gly His
            340                 345                 350
```

```
Val His Ala Tyr Glu Arg Ser Glu Arg Val Ser Asn Val Ala Tyr Asp
        355                 360                 365

Ile Val Asn Gly Lys Cys Thr Pro Val Arg Asp Gln Ser Ala Pro Val
        370                 375                 380

Tyr Ile Thr Ile Gly Asp Gly Gly Asn Leu Gly Leu Ala Thr Asn
385                 390                 395                 400

Met Thr Asp Pro Gln Pro Glu Tyr Ser Ala Phe Arg Glu Ala Ser Phe
                405                 410                 415

Gly His Ala Thr Leu Asp Ile Lys Asn Arg Thr His Ala Tyr Tyr Ser
        420                 425                 430

Trp His Arg Asn Gln Asp Gly Tyr Ala Val Glu Ala Asp Ser Met Trp
        435                 440                 445

Val Ser Asn Arg Phe Trp His Pro Val Asp Asp Ser Thr Thr Thr Lys
        450                 455                 460

Leu
465

<210> SEQ ID NO 28
<211> LENGTH: 470
<212> TYPE: PRT
<213> ORGANISM: Nicotiana tabacum

<400> SEQUENCE: 28

Met Gly Val Ser Lys Met Glu Phe Phe Gly Arg Cys Ile Val Leu Val
1               5                   10                  15

Leu Gly Leu Leu Leu Asn Glu Ser Leu Leu Cys Asn Gly Gly Val Thr
            20                  25                  30

Ser Ser Phe Ile Arg Lys Val Glu Lys Thr Val Asp Met Pro Leu Asp
        35                  40                  45

Ser Asp Val Phe Arg Ala Pro Pro Gly Tyr Asn Ala Pro Gln Gln Val
    50                  55                  60

His Ile Thr Gln Gly Asp His Glu Gly Lys Thr Val Ile Val Ser Trp
65                  70                  75                  80

Val Thr Met Asp Glu Pro Gly Ser Ser Thr Val Leu Tyr Trp Ser Glu
                85                  90                  95

Lys Ser Lys Gln Lys Asn Thr Ala Lys Gly Lys Val Thr Thr Tyr Lys
            100                 105                 110

Phe Tyr Asn Tyr Thr Ser Gly Tyr Ile His His Ser Thr Ile Arg His
        115                 120                 125

Leu Glu Phe Asn Thr Lys Tyr Tyr Tyr Lys Ile Gly Val Gly His Thr
    130                 135                 140

Ala Arg Thr Phe Trp Phe Val Thr Pro Pro Val Gly Pro Asp Val
145                 150                 155                 160

Pro Tyr Thr Phe Gly Leu Ile Gly Asp Leu Gly Gln Ser Phe Asp Ser
                165                 170                 175

Asn Lys Thr Leu Thr His Tyr Glu Leu Asn Pro Thr Lys Gly Gln Ala
            180                 185                 190

Val Leu Phe Val Gly Asp Leu Ser Tyr Ala Asp Asn Tyr Pro Asn His
        195                 200                 205

Asp Asn Val Arg Trp Asp Thr Trp Gly Arg Phe Val Glu Arg Ser Thr
    210                 215                 220

Ala Tyr Gln Pro Trp Ile Trp Thr Ala Gly Asn His Glu Ile Asp Phe
225                 230                 235                 240

Ala Pro Glu Ile Gly Glu Thr Lys Pro Phe Lys Pro Tyr Thr His Arg
                245                 250                 255
```

```
Tyr His Val Pro Tyr Arg Ala Ser Asn Ser Thr Ser Pro Leu Trp Tyr
            260                 265                 270

Ser Val Lys Arg Ala Ser Ala Tyr Ile Ile Val Leu Ser Ser Tyr Ser
        275                 280                 285

Ala Tyr Gly Lys Tyr Thr Pro Gln Tyr Lys Trp Leu Glu Glu Glu Leu
        290                 295                 300

Pro Lys Val Asn Arg Thr Glu Thr Pro Trp Leu Ile Val Leu Val His
305                 310                 315                 320

Ser Pro Trp Tyr Asn Ser Tyr Asn Tyr His Tyr Met Glu Gly Glu Thr
                325                 330                 335

Met Arg Val Met Tyr Glu Pro Trp Phe Val Lys Tyr Lys Val Asp Ile
            340                 345                 350

Val Phe Ala Gly His Val His Ala Tyr Glu Arg Thr Glu Arg Ile Ser
        355                 360                 365

Asn Val Ala Tyr Asn Val Val Asn Gly Glu Cys Thr Pro Ile Arg Asp
        370                 375                 380

Gln Ser Ala Pro Ile Tyr Val Thr Ile Gly Asp Gly Gly Asn Leu Glu
385                 390                 395                 400

Gly Leu Ala Thr Asn Met Thr Glu Pro Gln Pro Ala Tyr Ser Ala Phe
                405                 410                 415

Arg Glu Ala Ser Phe Gly His Ala Thr Leu Ala Ile Lys Asn Arg Thr
            420                 425                 430

His Ala Tyr Tyr Ser Trp His Arg Asn Gln Asp Gly Tyr Ala Val Glu
        435                 440                 445

Ala Asp Lys Ile Trp Val Asn Asn Arg Ile Trp Asn Pro Val Asp Glu
450                 455                 460

Ser Met Val Thr Lys Ser
465                 470

<210> SEQ ID NO 29
<211> LENGTH: 470
<212> TYPE: PRT
<213> ORGANISM: Nicotiana tabacum

<400> SEQUENCE: 29

Met Gly Val Arg Arg Thr Ser Phe Leu Gly Cys Phe Ile Leu Ala Val
1               5                   10                  15

Leu Gly Leu Ile Ile Ser Ala Pro Ile Leu Cys Arg Gly Gly Thr Thr
            20                  25                  30

Ser Ser Phe Val Arg Lys Val Glu Lys Thr Ile Asp Met Pro Met Asp
        35                  40                  45

Ser Asp Val Phe Ser Val Pro Pro Gly Tyr Asn Ala Pro Gln Gln Val
    50                  55                  60

His Ile Thr Gln Gly Asp His Val Gly Lys Ala Met Ile Val Ser Trp
65                  70                  75                  80

Val Thr Met Asp Glu Pro Gly Ser Ser Thr Val Leu Tyr Trp Ser Asn
                85                  90                  95

Asn Ser Lys Gln Lys Asn Lys Ala Thr Gly Ala Val Thr Thr Tyr Arg
            100                 105                 110

Phe Tyr Asn Tyr Thr Ser Gly Tyr Ile His His Cys Ile Ile Lys His
        115                 120                 125

Leu Lys Phe Asn Thr Lys Tyr Tyr Tyr Glu Val Gly Ile Gly His Asn
    130                 135                 140

Pro Arg Thr Phe Trp Phe Val Thr Pro Pro Gln Val Gly Pro Asp Val
```

```
                145                 150                 155                 160
Pro Tyr Thr Phe Gly Leu Ile Gly Asp Leu Gly Gln Ser Phe Asp Ser
                165                 170                 175

Asn Arg Thr Leu Thr His Tyr Glu Leu Asn Pro Ile Lys Gly Gln Thr
                180                 185                 190

Val Leu Phe Val Gly Asp Leu Ser Tyr Ala Asp Asn Tyr Pro Asn His
                195                 200                 205

Asp Asn Thr Arg Trp Asp Thr Trp Gly Arg Phe Val Glu Arg Ser Val
            210                 215                 220

Ala Tyr Gln Pro Trp Ile Trp Thr Thr Gly Asn His Glu Ile Asp Phe
225                 230                 235                 240

Ala Pro Glu Ile Gly Glu Thr Lys Pro Phe Lys Pro Tyr Thr His Arg
                245                 250                 255

Tyr Arg Val Pro Tyr Lys Ser Ser Asn Ser Thr Ala Pro Phe Trp Tyr
                260                 265                 270

Ser Ile Lys Arg Ala Ser Ala Tyr Ile Ile Val Leu Ser Ser Tyr Ser
            275                 280                 285

Ala Tyr Gly Met Tyr Thr Pro Gln Tyr Gln Trp Leu Tyr Glu Glu Leu
            290                 295                 300

Pro Lys Val Asn Arg Ser Glu Thr Pro Trp Leu Ile Val Leu Leu His
305                 310                 315                 320

Ser Pro Trp Tyr Asn Ser Tyr Asn Tyr His Tyr Met Glu Gly Glu Thr
                325                 330                 335

Met Arg Val Met Tyr Glu Pro Trp Phe Val Gln Tyr Lys Val Asp Val
                340                 345                 350

Val Phe Ala Gly His Val His Ala Tyr Glu Arg Ser Glu Arg Val Ser
                355                 360                 365

Asn Val Ala Tyr Asn Ile Val Asn Gly Lys Cys Thr Pro Val Arg Asp
            370                 375                 380

Gln Ser Ala Pro Ile Tyr Ile Thr Ile Gly Asp Gly Gly Asn Ile Glu
385                 390                 395                 400

Gly Leu Ala Asn Asn Met Thr Glu Pro Gln Pro Glu Tyr Ser Ala Phe
                405                 410                 415

Arg Glu Pro Ser Phe Gly His Ala Thr Leu Asp Ile Lys Asn Arg Thr
                420                 425                 430

His Ala Tyr Tyr Ser Trp His Arg Asn Gln Glu Gly Tyr Val Val Glu
            435                 440                 445

Ala Asp Lys Leu Arg Leu Tyr Asn Arg Phe Trp His Pro Val Asp Asp
            450                 455                 460

Ser Thr Thr Ala Lys Ser
465                 470

<210> SEQ ID NO 30
<211> LENGTH: 447
<212> TYPE: PRT
<213> ORGANISM: Solanum tuberosum

<400> SEQUENCE: 30

Ser Gly Pro Thr Ser Gly Glu Val Thr Ser Ser Phe Val Arg Lys Ile
1               5                   10                  15

Glu Lys Thr Ile Asp Met Pro Leu Asp Ser Asp Val Phe Arg Val Pro
                20                  25                  30

Pro Gly Tyr Asn Ala Pro Gln Gln Val His Ile Thr Gln Gly Asp His
            35                  40                  45
```

```
Val Gly Lys Ala Val Ile Val Ser Trp Val Thr Met Asp Glu Pro Gly
 50                  55                  60
Ser Ser Thr Val Val Tyr Trp Ser Glu Lys Ser Lys Leu Lys Asn Lys
 65                  70                  75                  80
Ala Asn Gly Lys Val Thr Thr Tyr Lys Phe Tyr Asn Tyr Thr Ser Gly
                 85                  90                  95
Tyr Ile His His Cys Asn Ile Lys Asn Leu Lys Phe Asp Thr Lys Tyr
            100                 105                 110
Tyr Tyr Lys Ile Gly Ile Gly His Val Ala Arg Thr Phe Trp Phe Thr
        115                 120                 125
Thr Pro Pro Glu Ala Gly Pro Asp Val Pro Tyr Thr Phe Gly Leu Ile
130                 135                 140
Gly Asp Leu Gly Gln Ser Phe Asp Ser Asn Lys Thr Leu Thr His Tyr
145                 150                 155                 160
Glu Leu Asn Pro Ile Lys Gly Gln Ala Val Ser Phe Val Gly Asp Ile
                165                 170                 175
Ser Tyr Ala Asp Asn Tyr Pro Asn His Asp Lys Lys Arg Trp Asp Thr
            180                 185                 190
Trp Gly Arg Phe Ala Glu Arg Ser Thr Ala Tyr Gln Pro Trp Ile Trp
        195                 200                 205
Thr Ala Gly Asn His Glu Ile Asp Phe Ala Pro Glu Ile Gly Glu Thr
210                 215                 220
Lys Pro Phe Lys Pro Tyr Thr His Arg Tyr His Val Pro Phe Arg Ala
225                 230                 235                 240
Ser Asp Ser Thr Ser Pro Leu Trp Tyr Ser Ile Lys Arg Ala Ser Ala
                245                 250                 255
Tyr Ile Ile Val Leu Ser Ser Tyr Ser Ala Tyr Gly Lys Tyr Thr Pro
            260                 265                 270
Gln Tyr Lys Trp Leu Glu Glu Leu Pro Lys Val Asn Arg Thr Glu
        275                 280                 285
Thr Pro Trp Leu Ile Val Leu Val His Ser Pro Trp Tyr Asn Ser Tyr
290                 295                 300
Asn Tyr His Tyr Met Glu Gly Glu Thr Met Arg Val Met Tyr Glu Pro
305                 310                 315                 320
Trp Phe Val Gln Tyr Lys Val Asn Met Val Phe Ala Gly His Val His
                325                 330                 335
Ala Tyr Glu Arg Thr Glu Arg Ile Ser Asn Val Ala Tyr Asn Val Val
            340                 345                 350
Asn Gly Glu Cys Ser Pro Ile Lys Asp Gln Ser Ala Pro Ile Tyr Val
        355                 360                 365
Thr Ile Gly Asp Gly Gly Asn Leu Glu Gly Leu Ala Thr Asn Met Thr
370                 375                 380
Glu Pro Gln Pro Ala Tyr Ser Ala Phe Arg Glu Ala Ser Phe Gly His
385                 390                 395                 400
Ala Thr Leu Ala Ile Lys Asn Arg Thr His Ala Tyr Tyr Ser Trp His
                405                 410                 415
Arg Asn Gln Asp Gly Tyr Ala Val Glu Ala Asp Lys Ile Trp Val Asn
            420                 425                 430
Asn Arg Val Trp His Pro Val Asp Glu Ser Thr Ala Ala Lys Ser
        435                 440                 445
```

<210> SEQ ID NO 31
<211> LENGTH: 468
<212> TYPE: PRT

<213> ORGANISM: Arabidopsis thaliana

<400> SEQUENCE: 31

```
Met Gly Arg Val Arg Lys Ser Asp Phe Gly Ser Ile Val Leu Val Leu
1               5                   10                  15
Cys Cys Val Leu Asn Ser Leu Leu Cys Asn Gly Ile Thr Ser Arg
                20                  25                  30
Tyr Val Arg Lys Leu Glu Ala Thr Val Asp Met Pro Leu Asp Ser Asp
            35                  40                  45
Val Phe Arg Val Pro Cys Gly Tyr Asn Ala Pro Gln Gln Val His Ile
        50                  55                  60
Thr Gln Gly Asp Val Glu Gly Lys Ala Val Ile Val Ser Trp Val Thr
65                  70                  75                  80
Gln Glu Ala Lys Gly Ser Asn Lys Val Ile Tyr Trp Lys Glu Asn Ser
                85                  90                  95
Thr Lys Lys His Lys Ala His Gly Lys Thr Asn Thr Tyr Lys Phe Tyr
            100                 105                 110
Asn Tyr Thr Ser Gly Phe Ile His His Cys Pro Ile Arg Asn Leu Glu
        115                 120                 125
Tyr Asp Thr Lys Tyr Tyr Val Leu Gly Val Gly Gln Thr Glu Arg
            130                 135                 140
Lys Phe Trp Phe Thr Pro Pro Glu Ile Gly Pro Asp Val Pro Tyr
145                 150                 155                 160
Thr Phe Gly Leu Ile Gly Asp Leu Gly Gln Ser Tyr Asp Ser Asn Ile
                165                 170                 175
Thr Leu Thr His Tyr Glu Asn Asn Pro Thr Lys Gly Gln Ala Val Leu
            180                 185                 190
Phe Val Gly Asp Ile Ser Tyr Ala Asp Thr Tyr Pro Asp His Asp Asn
        195                 200                 205
Arg Arg Trp Asp Ser Trp Gly Arg Phe Ala Glu Arg Ser Thr Ala Tyr
210                 215                 220
Gln Pro Trp Ile Trp Thr Thr Gly Asn His Glu Leu Asp Phe Ala Pro
225                 230                 235                 240
Glu Ile Gly Glu Asn Arg Pro Phe Lys Pro Phe Thr His Arg Tyr Arg
                245                 250                 255
Thr Pro Tyr Arg Ser Ser Gly Ser Thr Glu Pro Phe Trp Tyr Ser Ile
            260                 265                 270
Lys Arg Gly Pro Ala Tyr Ile Ile Val Leu Ala Ser Tyr Ser Ala Tyr
        275                 280                 285
Gly Lys Tyr Thr Pro Gln Tyr Gln Trp Leu Glu Glu Phe Pro Lys
            290                 295                 300
Val Asn Arg Thr Glu Thr Pro Trp Leu Ile Val Leu Met His Ser Pro
305                 310                 315                 320
Trp Tyr Asn Ser Tyr Asp Tyr His Tyr Met Glu Gly Glu Thr Met Arg
                325                 330                 335
Val Met Tyr Glu Ala Trp Phe Val Lys Tyr Lys Val Asp Val Phe
            340                 345                 350
Ala Gly His Val His Ala Tyr Glu Arg Ser Glu Arg Val Ser Asn Ile
        355                 360                 365
Ala Tyr Asn Val Val Asn Gly Ile Cys Thr Pro Val Lys Asp Gln Ser
370                 375                 380
Ala Pro Val Tyr Ile Thr Ile Gly Asp Gly Gly Asn Ile Glu Gly Leu
385                 390                 395                 400
```

```
Ala Thr Lys Met Thr Glu Pro Gln Pro Lys Tyr Ser Ala Phe Arg Glu
            405                 410                 415

Ala Ser Phe Gly His Ala Ile Phe Ser Ile Lys Asn Arg Thr His Ala
        420                 425                 430

His Tyr Gly Trp His Arg Asn His Asp Gly Tyr Ala Val Glu Gly Asp
            435                 440                 445

Arg Met Trp Phe Tyr Asn Arg Phe Trp His Pro Val Asp Asp Ser Pro
    450                 455                 460

Ser Cys Asn Ser
465

<210> SEQ ID NO 32
<211> LENGTH: 470
<212> TYPE: PRT
<213> ORGANISM: Anchusa Officinalis

<400> SEQUENCE: 32

Met Val Leu Ile Pro Lys Thr Lys Asn Leu Ile Phe Val Ser Leu
  1               5                  10                  15

Ile Leu Ala Phe Asn Ala Ala Thr Leu Cys Asn Gly Gly Ile Thr Ser
             20                  25                  30

Arg Phe Val Arg Lys Leu Ala Ala Ala Thr Asp Met Pro Leu Asn Ser
         35                  40                  45

Asp Val Phe Arg Val Pro Pro Gly Tyr Asn Ala Pro Gln Gln Val His
     50                  55                  60

Ile Thr Gln Gly Asp Leu Glu Gly Glu Ala Met Ile Ile Ser Trp Val
 65                  70                  75                  80

Arg Met Asp Glu Pro Gly Ser Ser Lys Val Leu Tyr Trp Ile Asp Gly
                 85                  90                  95

Ser Asn Gln Lys His Ser Ala Asn Gly Lys Ile Thr Lys Tyr Lys Tyr
            100                 105                 110

Tyr Asn Tyr Thr Ser Gly Phe Ile His His Cys Thr Ile Arg Arg Leu
        115                 120                 125

Lys His Asn Thr Lys Tyr His Tyr Glu Val Gly Ile Gly His Thr Val
    130                 135                 140

Arg Ser Phe Trp Phe Met Thr Pro Pro Glu Val Gly Pro Asp Val Pro
145                 150                 155                 160

Tyr Thr Phe Gly Leu Ile Gly Asp Leu Gly Gln Ser Tyr Asp Ser Asn
                165                 170                 175

Ser Thr Leu Thr His Tyr Glu Phe Asn Pro Thr Lys Gly Gln Ala Val
            180                 185                 190

Leu Phe Val Gly Asp Leu Ser Tyr Ala Asp Thr Tyr Pro Asn His Asp
        195                 200                 205

Asn Val Arg Trp Asp Thr Trp Gly Arg Phe Val Glu Arg Ser Val Ala
    210                 215                 220

Tyr Gln Pro Trp Ile Trp Thr Val Gly Asn His Glu Leu Asp Phe Glu
225                 230                 235                 240

Pro Asp Ile Gly Glu Thr Lys Pro Phe Lys Pro Phe Ser Asn Arg Tyr
                245                 250                 255

Arg Thr Pro Tyr Lys Ala Ser Asn Ser Thr Ser Pro Phe Phe Tyr Ser
            260                 265                 270

Ile Lys Arg Gly Pro Ala His Ile Ile Val Leu Ala Ser Tyr Ser Ala
        275                 280                 285

Tyr Gly Lys Tyr Thr Pro Gln Phe Lys Trp Leu Glu Asp Glu Leu Pro
    290                 295                 300
```

```
Lys Val Asn Arg Thr Glu Ser Pro Trp Leu Ile Val Leu Met His Ala
305                 310                 315                 320

Pro Trp Tyr Asn Ser Tyr Asn Tyr His Tyr Met Glu Gly Glu Thr Met
            325                 330                 335

Arg Val Met Tyr Glu Ala His Gly Phe Val Lys Tyr Lys Val Asp Leu
            340                 345                 350

Val Phe Ala Gly His Val His Ala Tyr Glu Arg Thr Glu Arg Ile Ser
            355                 360                 365

Asn Ile Val Tyr Asn Val Val Asn Gly Ile Cys Thr Pro Val Asn Asp
            370                 375                 380

Ser Ser Ala Pro Ile Tyr Ile Thr Ile Gly Asp Gly Asn Leu Glu
385                 390                 395                 400

Gly Leu Ala Lys Asn Met Thr Glu Pro Gln Pro Lys Tyr Ser Ala Phe
            405                 410                 415

Arg Glu Ala Ser Phe Gly His Ala Thr Leu Asp Ile Lys Asn Arg Thr
            420                 425                 430

His Ala Tyr Tyr Ala Trp His Arg Asn Gln Asp Gly Tyr Ala Val Glu
            435                 440                 445

Ala Asp Thr Leu Trp Ile Phe Asn Arg Tyr Trp Asn Pro Val Asp Glu
            450                 455                 460

Ser Thr Ser Ala Thr Ala
465                 470

<210> SEQ ID NO 33
<211> LENGTH: 461
<212> TYPE: PRT
<213> ORGANISM: Nicotiana tabacum

<400> SEQUENCE: 33

Met Gly Ile Ser Trp Phe Tyr Val Val Ala Ile Leu Leu Phe Ile Thr
1               5                   10                  15

Asn Thr Ala Thr Leu Cys Arg Gly Gly Ile Thr Ser Ser Tyr Val Arg
            20                  25                  30

Lys Val Glu Ser Ser Glu Asp Met Pro Leu Asp Ser Asp Val Phe Arg
        35                  40                  45

Val Pro His Gly Tyr Asn Ala Pro Gln Gln Val His Leu Thr Gln Gly
    50                  55                  60

Asp His Val Gly Lys Gly Val Ile Val Ser Trp Val Thr Met Asp Glu
65                  70                  75                  80

Pro Gly Ser Asn Lys Val Leu Tyr Trp Glu Phe Asn Ser Lys Ile Lys
                85                  90                  95

Gln Ile Ala Lys Gly Thr Val Ser Thr Tyr Lys Tyr His Thr Tyr Asn
            100                 105                 110

Ser Gly Tyr Ile His His Cys Thr Ile Gln Asn Leu Lys Tyr Asn Thr
        115                 120                 125

Lys Tyr Tyr Tyr Met Val Gly Thr Gly His Ser Arg Arg Thr Phe Trp
    130                 135                 140

Phe Val Thr Pro Pro Val Gly Pro Asp Val Ser Tyr Thr Phe Gly
145                 150                 155                 160

Leu Ile Gly Asp Leu Gly Gln Thr Tyr Asp Pro Asn Met Thr Leu Thr
                165                 170                 175

His Tyr Glu Met Asn Pro Thr Gln Gly Gln Thr Val Leu Phe Val Gly
            180                 185                 190

Asp Leu Ser Tyr Ala Asp Lys Tyr Pro Asn His Asp Asn Asn Gly Trp
```

```
                195                 200                 205
Asp Thr Trp Gly Arg Phe Val Glu Arg Ser Asn Ala Tyr Gln Pro Trp
        210                 215                 220

Ile Trp Thr Ala Gly Asn His Asp Val Asp Phe Ala Pro Glu Ile Gly
225                 230                 235                 240

Glu Pro Glu Pro Phe Arg Pro Tyr Thr Asn Arg Tyr Pro Val Pro Tyr
                245                 250                 255

Gln Ala Ser Gly Ser Ser Ser Pro Leu Trp Tyr Ser Ile Lys Arg Ala
                260                 265                 270

Ser Ala Tyr Ile Ile Val Leu Ser Thr Tyr Ser Ala Thr Ser Lys Tyr
                275                 280                 285

Thr Pro Gln Tyr Arg Trp Leu Glu Ala Glu Leu Lys Lys Val Asn Arg
        290                 295                 300

Lys Glu Thr Pro Trp Leu Ile Val Leu Met His Cys Pro Trp Tyr Asn
305                 310                 315                 320

Ser Tyr Gly Tyr His Tyr Met Glu Gly Glu Thr Met Arg Val Ile Tyr
                325                 330                 335

Glu Pro Trp Phe Val Lys Tyr Lys Val Asp Met Val Phe Ala Gly His
                340                 345                 350

Val His Ala Tyr Glu Arg Ser Lys Arg Ile Ser Asn Ile Asp Tyr Lys
        355                 360                 365

Ile Val Ser Gly Glu Cys Thr Pro Ala Ser Asn Pro Ser Ala Pro Val
370                 375                 380

Tyr Ile Thr Val Gly Asp Gly Gly Asn Ile Glu Gly Leu Thr Thr Lys
385                 390                 395                 400

Met Thr Glu Pro Gln Pro Lys Tyr Ser Ala Tyr Arg Glu Ser Ser Phe
                405                 410                 415

Gly His Ala Ile Leu Glu Ile Lys Asn Arg Thr His Ala Tyr Tyr Ser
                420                 425                 430

Trp His Arg Asn Gln Asp Gly Phe Ser Ala Lys Ala Asp Ser Phe Leu
        435                 440                 445

Phe Phe Asn Arg Tyr Trp His Pro Val Asp Glu Ser Tyr
        450                 455                 460

<210> SEQ ID NO 34
<211> LENGTH: 455
<212> TYPE: PRT
<213> ORGANISM: Spirodela punctata

<400> SEQUENCE: 34

Met Ala Arg Leu Val Leu Ala Val Met Leu Leu Leu Asn Ala Ala Ile
1               5                   10                  15

Leu Cys Ser Gly Gly Ile Thr Ser Glu Phe Val Arg Leu Gln Glu Ser
            20                  25                  30

Ala Val Asp Met Pro Leu His Ala Asp Val Phe Arg Met Pro Pro Gly
        35                  40                  45

Tyr Asn Ala Pro Gln Gln Val His Ile Thr Gln Gly Asp His Glu Gly
    50                  55                  60

Arg Ser Ile Ile Val Ser Trp Ile Thr Pro Ser Glu Lys Gly Ser Ser
65                  70                  75                  80

Thr Val Phe Tyr Gly Thr Ser Glu Asn Lys Leu Asp Gln His Ala Glu
                85                  90                  95

Gly Thr Val Thr Met Tyr Lys Phe Tyr Thr Tyr Thr Ser Gly Tyr Ile
                100                 105                 110
```

```
His His Cys Val Leu Thr Asp Leu Lys Tyr Asp Arg Lys Tyr Phe Tyr
        115                 120                 125
Lys Val Gly Glu Gly Ser Ala Ala Arg Leu Phe Trp Phe Lys Thr Pro
    130                 135                 140
Pro Glu Val Gly Pro Asp Val Pro Tyr Thr Phe Gly Leu Ile Gly Asp
145                 150                 155                 160
Leu Gly Gln Thr Phe Asp Ser Asn Val Thr Leu Thr His Tyr Glu Ser
                165                 170                 175
Asn Pro Gly Gly Gln Ala Val Leu Tyr Val Gly Asp Leu Ser Tyr Ala
            180                 185                 190
Asp Val Tyr Pro Asp His Asp Asn Val Arg Trp Asp Thr Trp Gly Arg
        195                 200                 205
Phe Val Glu Arg Ser Thr Ala Tyr Gln Pro Trp Ile Trp Thr Thr Gly
    210                 215                 220
Asn His Glu Ile Asp Tyr Ala Pro Glu Ile Gly Glu Tyr Val Pro Phe
225                 230                 235                 240
Lys Pro Phe Thr His Arg Tyr His Val Pro His Lys Ser Ser Gly Ser
                245                 250                 255
Gly Ser Pro Phe Trp Tyr Ser Ile Lys Arg Ala Ser Ala Tyr Ile Ile
            260                 265                 270
Val Leu Ala Ser Tyr Ser Ala Phe Gly Lys Tyr Thr Pro Gln Ser Glu
        275                 280                 285
Trp Leu Glu Gln Glu Phe Pro Lys Val Asn Arg Ser Glu Thr Pro Trp
    290                 295                 300
Leu Ile Val Leu Met His Ser Pro Leu Tyr Asn Ser Tyr Asn Tyr His
305                 310                 315                 320
Tyr Met Glu Gly Glu Thr Met Arg Val Met Tyr Glu Pro Leu Phe Val
                325                 330                 335
Thr Tyr Lys Val Asp Val Ile Phe Ala Gly His Val His Ala Tyr Glu
            340                 345                 350
Arg Ser Tyr Arg Ile Ser Asn Val Ala Tyr Asn Ile Thr Asp Gly Lys
        355                 360                 365
Cys Thr Pro Thr Ser Asp Leu Ser Ala Pro Val Tyr Ile Thr Val Gly
    370                 375                 380
Asp Gly Asn Gln Glu Gly Leu Ala Ser Ser Met Thr Glu Pro Gln
385                 390                 395                 400
Pro Asn Tyr Ser Ala Tyr Arg Glu Ala Ser Phe Gly His Ala Ile Phe
                405                 410                 415
Gly Ile Lys Asn Arg Thr His Ala Tyr Tyr Asn Trp Tyr Arg Asn Gln
            420                 425                 430
Asp Gly Asn Ala Val Glu Ala Asp Ser Leu Trp Phe Phe Asn Arg Val
        435                 440                 445
Trp Asn Pro Arg Glu Glu Ser
    450                 455

<210> SEQ ID NO 35
<211> LENGTH: 465
<212> TYPE: PRT
<213> ORGANISM: Oryza sativa

<400> SEQUENCE: 35

Met Val Asp Arg Ile Gly Ala Ala Trp Trp Cys Ala Cys Ala Val Gly
1               5                   10                  15
Met Leu Val Val Gly Ala Cys Leu Ala Gly Glu Thr Ser Glu Tyr Arg
            20                  25                  30
```

```
Arg Gln Leu Gly Ser Ala Val Asp Met Pro Leu Asp Ala Asp Val Phe
             35                  40                  45

Arg Ala Pro Pro Gly Arg Asn Ala Pro Gln Gln Val His Ile Thr Gln
 50                  55                  60

Gly Asn His Asp Gly Thr Ala Met Ile Ile Ser Trp Val Thr Thr Ile
 65                  70                  75                  80

Glu Pro Gly Ser Ser Thr Val Leu Tyr Gly Thr Ser Glu Asp Asn Leu
                 85                  90                  95

Asn Phe Ser Ala Asp Gly Lys His Thr Gln Tyr Thr Phe Tyr Asn Tyr
             100                 105                 110

Thr Ser Gly Tyr Ile His His Cys Thr Ile Lys Lys Leu Glu Phe Asp
         115                 120                 125

Thr Lys Tyr Tyr Tyr Ala Val Gly Ile Gly Gln Thr Val Arg Lys Phe
         130                 135                 140

Trp Phe Arg Thr Pro Pro Lys Ser Gly Pro Asp Val Pro Tyr Thr Phe
145                 150                 155                 160

Gly Leu Ile Gly Asp Leu Gly Gln Ser Tyr Asp Ser Asn Ile Thr Leu
                 165                 170                 175

Ala His Tyr Glu Ser Asn Ser Lys Ala Gln Ala Val Leu Phe Val Gly
             180                 185                 190

Asp Leu Cys Tyr Ala Asp Asn Tyr Pro Tyr His Asp Asn Val Arg Trp
         195                 200                 205

Asp Thr Trp Ala Arg Phe Val Glu Arg Asn Val Ala Tyr Gln Pro Trp
     210                 215                 220

Ile Trp Thr Ala Gly Asn His Glu Ile Asp Phe Ala Pro Glu Leu Gly
225                 230                 235                 240

Glu Thr Lys Pro Phe Lys Pro Tyr Ser Tyr Arg Tyr Pro Thr Pro Tyr
                 245                 250                 255

Lys Ala Ser Gly Ser Thr Ala Pro Phe Trp Tyr Ser Val Lys Arg Ala
             260                 265                 270

Ser Ala Tyr Ile Ile Val Leu Ala Ser Tyr Ser Ser Tyr Gly Lys Tyr
         275                 280                 285

Thr Pro Gln Tyr Lys Trp Leu Glu Ala Glu Phe Pro Lys Val Asn Arg
     290                 295                 300

Ser Glu Thr Pro Trp Leu Ile Val Leu Leu His Ala Pro Trp Tyr Asn
305                 310                 315                 320

Ser Tyr Asn Tyr His Tyr Met Glu Gly Glu Ser Met Arg Val Met Tyr
                 325                 330                 335

Glu Pro Trp Phe Val Lys Tyr Lys Val Asp Leu Val Phe Ala Gly His
             340                 345                 350

Val His Ala Tyr Glu Arg Thr His Arg Ile Ser Asn Val Ala Tyr Asn
         355                 360                 365

Ile Val Asn Gly Gln Cys Thr Pro Val His Asp Gln Ser Ala Pro Val
     370                 375                 380

Tyr Ile Thr Ile Gly Asp Gly Gly Asn Gln Glu Gly Leu Ala Thr Asn
385                 390                 395                 400

Met Thr Ala Pro Gln Pro Gly Tyr Ser Ala Phe Arg Glu Ser Ser Phe
                 405                 410                 415

Gly His Ala Ile Leu Asp Ile Lys Asn Arg Thr His Ala Tyr Tyr Thr
             420                 425                 430

Trp His Arg Asn Gln Asp Gly Asn Ala Val Ala Ala Asp Ser Met Trp
         435                 440                 445
```

```
Phe Thr Asn Arg Tyr Trp Gln Pro Thr Asp Glu Ser Leu Asp Asp Ser
    450                 455                 460

Gln
465

<210> SEQ ID NO 36
<211> LENGTH: 468
<212> TYPE: PRT
<213> ORGANISM: Nicotiana tabacum

<400> SEQUENCE: 36

Met Gly Met Lys Arg Val Tyr Thr Gly Phe Leu Cys Leu Leu Thr Val
1               5                   10                  15

Leu Ile Leu Ser Ser Arg Ala Gln Leu Ser Asp Gly Gly Ile Thr Ser
            20                  25                  30

Asn Tyr Val Arg Lys Tyr Asn Ser Asn Val Asp Met Pro Leu Asn Ser
        35                  40                  45

Asp Val Phe Arg Val Pro Pro Gly Tyr Asn Ala Pro Gln Gln Val Tyr
    50                  55                  60

Ile Thr Gln Gly Asp His Glu Gly Lys Gly Val Ile Ala Ser Trp Thr
65                  70                  75                  80

Thr Pro Asp Glu Pro Gly Ser Asn Ser Val Leu Tyr Trp Ala Glu Asn
                85                  90                  95

Ser Asn Val Lys Ser Ser Ala Glu Gly Phe Val Ser Tyr Arg Tyr
            100                 105                 110

Tyr Asn Tyr Thr Ser Gly Tyr Ile His His Cys Thr Ile Lys Asp Leu
        115                 120                 125

Glu Phe Asp Thr Lys Tyr Tyr Tyr Glu Val Gly Leu Glu Asn Thr Thr
    130                 135                 140

Arg Lys Phe Trp Phe Val Thr Pro Pro Lys Pro Gly Pro Asp Val Pro
145                 150                 155                 160

Tyr Thr Phe Gly Leu Ile Gly Asp Leu Gly Gln Thr Tyr Asp Ser Asn
                165                 170                 175

Ser Thr Leu Thr His Tyr Glu Leu Asn Pro Leu Lys Gly Gln Thr Met
            180                 185                 190

Leu Phe Val Gly Asp Leu Ser Tyr Ala Asp Asn Tyr Pro Phe His Asn
        195                 200                 205

Asn Ile Arg Trp Asp Thr Trp Gly Arg Phe Ile Glu Arg Ser Ala Ala
    210                 215                 220

Tyr Gln Pro Trp Ile Trp Thr Ala Gly Asn His Glu Leu Asp Phe Val
225                 230                 235                 240

Pro Glu Ile Gly Glu Ser Lys Pro Phe Leu Pro Tyr Lys His Arg Phe
                245                 250                 255

Ser Thr Pro Tyr Arg Val Ser Asp Ser Thr Ser Pro Leu Trp Tyr Ser
            260                 265                 270

Ile Lys Arg Ala Ser Ala Tyr Ile Ile Val Met Ser Ser Tyr Ser Ala
        275                 280                 285

Phe Gly Thr Tyr Thr Pro Gln Trp Lys Trp Leu Lys Asn Glu Leu Pro
    290                 295                 300

Lys Val Asn Arg Ser Glu Thr Pro Trp Leu Ile Val Leu Met His Cys
305                 310                 315                 320

Pro Met Tyr Ser Ser Tyr Val His His Tyr Met Glu Gly Glu Thr Met
                325                 330                 335

Arg Val Met Tyr Glu Pro Trp Phe Val Asn Tyr Lys Val Asp Val Val
            340                 345                 350
```

```
Phe Ala Gly His Val His Ala Tyr Glu Arg Ser Glu Arg Ile Ser Asn
            355                 360                 365

Val Ala Tyr Asn Ile Ile Asn Arg Lys Cys Ser Pro Val Arg Asp Glu
        370                 375                 380

Ser Ala Pro Val Tyr Ile Thr Ile Gly Asp Gly Asn Gln Glu Gly
385                 390                 395                 400

Leu Ala Thr Glu Met Thr Gln Pro Gln Pro Arg Tyr Ser Ala Tyr Arg
                405                 410                 415

Glu Ala Ser Phe Gly His Gly Ile Leu Asp Ile Lys Asn Arg Thr His
                420                 425                 430

Ala Tyr Phe Gly Trp His Arg Asn Asn Asp Gly Tyr Ala Val Glu Ala
            435                 440                 445

Asp Ser Leu Trp Leu Phe Asn Arg Tyr Trp Lys Leu Asp Gly Pro Ser
450                 455                 460

Val Ser Met Ser
465

<210> SEQ ID NO 37
<211> LENGTH: 427
<212> TYPE: PRT
<213> ORGANISM: Ipomoea batatas

<400> SEQUENCE: 37

Asp Met Pro Leu Asp Ser Asp Val Phe Arg Val Pro Pro Gly Tyr Asn
 1               5                  10                  15

Val Pro Gln Gln Val His Ile Thr Gln Gly Asp Tyr Glu Gly Lys Gly
                20                  25                  30

Val Ile Ile Ser Trp Val Thr Pro Glu Pro Gly Ser Lys Thr Val
             35                  40                  45

Val Tyr Trp Ala Glu Asn Ser Ser Val Lys Arg Arg Ala Asp Gly Val
     50                  55                  60

Val Val Thr Tyr Lys Tyr Tyr Asn Tyr Thr Ser Gly Tyr Ile His His
 65                  70                  75                  80

Cys Thr Ile Lys Asp Leu Glu Tyr Asp Thr Lys Tyr Tyr Tyr Glu Leu
                 85                  90                  95

Gly Leu Gly Asp Ala Lys Arg Gln Phe Trp Phe Val Thr Pro Pro Lys
            100                 105                 110

Pro Gly Pro Asp Val Pro Tyr Thr Phe Gly Leu Ile Gly Asp Leu Gly
        115                 120                 125

Gln Thr Tyr Asp Ser Asn Thr Thr Leu Thr His Tyr Glu Leu Asn Pro
    130                 135                 140

Val Lys Gly Gln Ser Leu Leu Phe Val Gly Asp Leu Ser Tyr Ala Asp
145                 150                 155                 160

Arg Tyr Pro Asn His Asp Asn Asn Arg Trp Asp Thr Trp Gly Arg Phe
                165                 170                 175

Val Glu Arg Ser Thr Ala Tyr Gln Pro Trp Ile Trp Thr Ala Gly Asn
            180                 185                 190

His Glu Ile Asp Phe Val Pro Asp Ile Gly Glu Thr Val Pro Phe Lys
        195                 200                 205

Pro Phe Thr His Arg Phe Phe Met Pro Phe Glu Ser Ser Gly Ser Thr
    210                 215                 220

Ser Pro Leu Trp Tyr Ser Ile Lys Arg Ala Ser Ala His Ile Ile Val
225                 230                 235                 240

Met Ser Ser Tyr Ser Ala Tyr Gly Thr Tyr Thr Pro Gln Trp Lys Trp
```

-continued

```
                245                 250                 255

Leu Gln Gly Glu Leu Pro Lys Val Asn Arg Ser Glu Thr Pro Trp Leu
            260                 265                 270

Ile Val Leu Met His Cys Pro Met Tyr Ser Ser Tyr Val His His Tyr
        275                 280                 285

Met Glu Gly Glu Thr Met Arg Val Leu Tyr Glu Pro Trp Phe Val Glu
    290                 295                 300

Tyr Lys Val Asp Val Val Phe Ala Gly His Val His Ser Tyr Glu Arg
305                 310                 315                 320

Thr Glu Arg Val Ser Asn Val Ala Tyr Asn Ile Val Asn Gly Leu Cys
                325                 330                 335

Ser Pro Lys Asn Asp Ser Ser Ala Pro Val Tyr Ile Thr Ile Gly Asp
            340                 345                 350

Gly Gly Asn Ser Glu Gly Leu Ala Thr Glu Met Thr Gln Pro Gln Pro
        355                 360                 365

Ser Tyr Ser Ala Tyr Arg Glu Ala Ser Phe Gly His Gly Ile Phe Asp
    370                 375                 380

Ile Lys Asn Arg Thr His Ala His Phe Gly Trp His Arg Asn Gln Asp
385                 390                 395                 400

Gly Leu Ala Val Glu Gly Asp Ser Leu Trp Phe Ile Asn Arg Tyr Trp
                405                 410                 415

Met Ser Lys Glu Glu Ala Ser Val Ser Ala Val
            420                 425

<210> SEQ ID NO 38
<211> LENGTH: 431
<212> TYPE: PRT
<213> ORGANISM: Ipomoea batatas
<220> FEATURE:
<221> NAME/KEY: modified_res
<222> LOCATION: (4)
<223> OTHER INFORMATION: x = can be any natural occurring amino acid

<400> SEQUENCE: 38

Ser Asp Ile Xaa Asp Met Pro Leu Asp Ser Asp Val Phe Arg Val Pro
1               5                   10                  15

Pro Gly Tyr Asn Val Pro Gln Gln Val His Ile Thr Gln Gly Asp Tyr
            20                  25                  30

Glu Gly Lys Gly Val Ile Ile Ser Trp Val Thr Pro Glu Glu Pro Gly
        35                  40                  45

Ser Lys Thr Val Val Tyr Trp Ala Glu Asn Ser Ser Val Lys Arg Arg
    50                  55                  60

Ala Asp Gly Val Val Val Thr Tyr Lys Tyr Tyr Asn Tyr Thr Ser Gly
65                  70                  75                  80

Tyr Ile His His Cys Thr Ile Lys Asp Leu Glu Tyr Asp Thr Lys Tyr
                85                  90                  95

Tyr Tyr Glu Leu Gly Leu Gly Asp Ala Lys Arg Gln Phe Trp Phe Val
            100                 105                 110

Thr Pro Pro Lys Pro Gly Pro Asp Val Pro Tyr Thr Phe Gly Leu Ile
        115                 120                 125

Gly Asp Leu Gly Gln Thr Tyr Asp Ser Asn Thr Thr Leu Thr His Tyr
    130                 135                 140

Glu Leu Asn Pro Val Lys Gly Gln Ser Leu Leu Phe Val Gly Asp Leu
145                 150                 155                 160

Ser Tyr Ala Asp Arg Tyr Pro Asn His Asp Asn Asn Arg Trp Asp Thr
                165                 170                 175
```

Trp Gly Arg Phe Val Glu Arg Ser Thr Ala Tyr Gln Pro Trp Ile Trp
                180                 185                 190

Thr Ala Gly Asn His Glu Ile Asp Phe Val Pro Asp Ile Gly Glu Thr
            195                 200                 205

Val Pro Phe Lys Pro Phe Thr His Arg Phe Phe Met Pro Phe Glu Ser
210                 215                 220

Ser Gly Ser Thr Ser Pro Leu Trp Tyr Ser Ile Lys Arg Ala Ser Ala
225                 230                 235                 240

His Ile Ile Val Met Ser Ser Tyr Ser Ala Tyr Gly Thr Tyr Thr Pro
                245                 250                 255

Gln Trp Lys Trp Leu Gln Gly Glu Leu Pro Lys Val Asn Arg Ser Glu
            260                 265                 270

Thr Pro Trp Leu Ile Val Leu Met His Cys Pro Met Tyr Ser Ser Tyr
                275                 280                 285

Val His His Tyr Met Glu Gly Glu Thr Met Arg Val Leu Tyr Glu Pro
290                 295                 300

Trp Phe Val Glu Tyr Lys Val Asp Val Val Phe Ala Gly His Val His
305                 310                 315                 320

Ser Tyr Glu Arg Thr Glu Arg Val Ser Asn Val Ala Tyr Asn Ile Val
                325                 330                 335

Asn Gly Leu Cys Ser Pro Lys Asn Asp Ser Ser Ala Pro Val Tyr Ile
            340                 345                 350

Thr Ile Gly Asp Gly Gly Asn Ser Glu Gly Leu Ala Thr Glu Met Thr
            355                 360                 365

Gln Pro Gln Pro Ser Tyr Ser Ala Tyr Arg Glu Ala Ser Phe Gly His
            370                 375                 380

Gly Ile Phe Asp Ile Lys Asn Arg Thr His Ala His Phe Gly Trp His
385                 390                 395                 400

Arg Asn Gln Asp Gly Leu Ala Val Glu Gly Asp Ser Leu Trp Phe Ile
                405                 410                 415

Asn Arg Tyr Trp Met Ser Lys Glu Glu Ala Ser Val Ser Ala Val
            420                 425                 430

<210> SEQ ID NO 39
<211> LENGTH: 469
<212> TYPE: PRT
<213> ORGANISM: Arabidopsis thaliana

<400> SEQUENCE: 39

Met Ser Ser Arg Ser Asp Leu Lys Ile Lys Arg Val Ser Leu Ile Ile
1               5                   10                  15

Phe Leu Leu Ser Val Leu Val Glu Phe Cys Tyr Gly Gly Phe Thr Ser
                20                  25                  30

Glu Tyr Val Arg Gly Ser Asp Leu Pro Asp Asp Met Pro Leu Asp Ser
            35                  40                  45

Asp Val Phe Glu Val Pro Pro Gly Pro Asn Ser Pro Gln Gln Val His
    50                  55                  60

Val Thr Gln Gly Asn His Glu Gly Asn Gly Val Ile Ile Ser Trp Val
65                  70                  75                  80

Thr Pro Val Lys Pro Gly Ser Lys Thr Val Arg Tyr Trp Cys Glu Asn
                85                  90                  95

Lys Lys Ser Arg Lys Gln Ala Glu Ala Thr Val Asn Thr Tyr Arg Phe
            100                 105                 110

Phe Asn Tyr Thr Ser Gly Tyr Ile His His Cys Leu Ile Asp Asp Leu

-continued

```
            115                 120                 125
Glu Phe Asp Thr Lys Tyr Tyr Glu Ile Gly Ser Gly Lys Trp Ser
        130                 135                 140

Arg Arg Phe Trp Phe Phe Thr Pro Pro Lys Ser Gly Pro Asp Val Pro
145                 150                 155                 160

Tyr Thr Phe Gly Leu Ile Gly Asp Leu Gly Gln Thr Tyr Asp Ser Asn
                165                 170                 175

Ser Thr Leu Ser His Tyr Glu Met Asn Pro Gly Lys Gly Gln Ala Val
            180                 185                 190

Leu Phe Val Gly Asp Leu Ser Tyr Ala Asp Arg Tyr Pro Asn His Asp
        195                 200                 205

Asn Asn Arg Trp Asp Thr Trp Gly Arg Phe Val Glu Arg Ser Val Ala
210                 215                 220

Tyr Gln Pro Trp Ile Trp Thr Ala Gly Asn His Glu Ile Asp Phe Val
225                 230                 235                 240

Pro Asp Ile Gly Glu Ile Glu Pro Phe Lys Pro Phe Met Asn Arg Tyr
                245                 250                 255

His Thr Pro His Lys Ala Ser Gly Ser Ile Ser Pro Leu Trp Tyr Ser
            260                 265                 270

Ile Lys Arg Ala Ser Ala Tyr Ile Ile Val Met Ser Cys Tyr Ser Ser
        275                 280                 285

Tyr Gly Ile Tyr Thr Pro Gln Tyr Lys Trp Leu Glu Lys Glu Leu Gln
        290                 295                 300

Gly Val Asn Arg Thr Glu Thr Pro Trp Leu Ile Val Leu Val His Ser
305                 310                 315                 320

Pro Phe Tyr Ser Ser Tyr Val His His Tyr Met Glu Gly Glu Thr Leu
                325                 330                 335

Arg Val Met Tyr Glu Gln Trp Phe Val Lys Tyr Lys Val Asp Val Val
            340                 345                 350

Phe Ala Gly His Val His Ala Tyr Glu Arg Ser Glu Arg Val Ser Asn
        355                 360                 365

Ile Ala Tyr Asn Ile Val Asn Gly Leu Cys Glu Pro Ile Ser Asp Glu
        370                 375                 380

Ser Ala Pro Ile Tyr Ile Thr Ile Gly Asp Gly Gly Asn Ser Glu Gly
385                 390                 395                 400

Leu Leu Thr Asp Met Met Gln Pro Gln Pro Lys Tyr Ser Ala Phe Arg
                405                 410                 415

Glu Ala Ser Phe Gly His Gly Leu Leu Glu Ile Lys Asn Arg Thr His
            420                 425                 430

Ala Tyr Phe Ser Trp Asn Arg Asn Gln Asp Gly Asn Ala Val Ala Ala
        435                 440                 445

Asp Ser Val Trp Leu Leu Asn Arg Phe Trp Arg Ala Gln Lys Lys Thr
    450                 455                 460

Trp Leu Asp Ala Phe
465

<210> SEQ ID NO 40
<211> LENGTH: 469
<212> TYPE: PRT
<213> ORGANISM: Arabidopsis thaliana

<400> SEQUENCE: 40

Met Ser Ser Arg Ser Asp Leu Lys Ile Lys Arg Val Ser Leu Ile Ile
1               5                   10                  15
```

```
Phe Leu Leu Ser Val Leu Val Glu Phe Cys Tyr Gly Gly Phe Thr Ser
             20                  25                  30
Glu Tyr Val Arg Gly Ser Asp Leu Pro Asp Asp Met Pro Leu Asp Ser
         35                  40                  45
Asp Val Phe Glu Val Pro Pro Gly His Asn Ser Pro Gln Gln Val His
     50                  55                  60
Val Thr Gln Gly Asn His Glu Gly Asn Gly Val Ile Ile Ser Trp Val
 65                  70                  75                  80
Thr Pro Val Lys Pro Gly Ser Lys Thr Val Gln Tyr Trp Cys Glu Asn
                 85                  90                  95
Glu Lys Ser Arg Lys Gln Ala Glu Ala Thr Val Asn Thr Tyr Arg Phe
            100                 105                 110
Phe Asn Tyr Thr Ser Gly Tyr Ile His His Cys Leu Ile Asp Asp Leu
        115                 120                 125
Glu Phe Asp Thr Lys Tyr Tyr Tyr Glu Ile Gly Ser Gly Lys Trp Ser
    130                 135                 140
Arg Arg Phe Trp Phe Phe Ile Pro Pro Lys Ser Gly Pro Asp Val Pro
145                 150                 155                 160
Tyr Thr Phe Gly Leu Ile Gly Asp Leu Gly Gln Thr Tyr Asp Ser Asn
                165                 170                 175
Ser Thr Leu Ser His Tyr Glu Met Asn Pro Gly Lys Gly Gln Ala Val
            180                 185                 190
Leu Phe Val Gly Asp Leu Ser Tyr Ala Asp Arg Tyr Pro Asn His Asp
        195                 200                 205
Asn Asn Arg Trp Asp Thr Trp Gly Arg Phe Val Glu Arg Ser Val Ala
210                 215                 220
Tyr Gln Pro Trp Ile Trp Thr Ala Gly Asn His Glu Ile Asp Phe Val
225                 230                 235                 240
Pro Asp Ile Gly Glu Ile Glu Pro Phe Lys Pro Phe Met Asn Arg Tyr
                245                 250                 255
His Thr Pro His Lys Ala Ser Gly Ser Ile Ser Pro Leu Trp Tyr Ser
            260                 265                 270
Ile Lys Arg Ala Ser Ala Tyr Ile Ile Val Met Ser Cys Tyr Ser Ser
        275                 280                 285
Tyr Gly Ile Tyr Thr Pro Gln Tyr Lys Trp Leu Glu Lys Glu Leu Gln
    290                 295                 300
Gly Val Asn Arg Thr Glu Thr Pro Trp Leu Ile Val Leu Val His Ser
305                 310                 315                 320
Pro Phe Tyr Ser Ser Tyr Val His His Tyr Met Glu Gly Glu Thr Leu
                325                 330                 335
Arg Val Met Tyr Glu Gln Trp Phe Val Lys Tyr Lys Val Asp Val Val
            340                 345                 350
Phe Ala Gly His Val His Ala Tyr Glu Arg Ser Glu Arg Val Ser Asn
        355                 360                 365
Ile Ala Tyr Asn Ile Val Asn Gly Leu Cys Glu Pro Ile Ser Asp Glu
    370                 375                 380
Ser Ala Pro Ile Tyr Ile Thr Ile Gly Asp Gly Gly Asn Ser Glu Gly
385                 390                 395                 400
Leu Leu Thr Asp Met Met Gln Pro Gln Pro Lys Tyr Ser Ala Phe Arg
                405                 410                 415
Glu Ala Ser Phe Gly His Gly Leu Leu Glu Ile Lys Asn Arg Thr His
            420                 425                 430
Ala Tyr Phe Ser Trp Asn Arg Asn Gln Asp Gly Asn Ala Val Ala Ala
```

```
                435                 440                 445
Asp Ser Val Trp Leu Leu Asn Arg Phe Trp Arg Ala Gln Lys Lys Thr
        450                 455                 460

Trp Leu Asp Ala Phe
465

<210> SEQ ID NO 41
<211> LENGTH: 469
<212> TYPE: PRT
<213> ORGANISM: Arabidopsis thaliana

<400> SEQUENCE: 41

Met Ser Ser Arg Ser Asp Leu Lys Ile Lys Arg Val Ser Leu Ile Ile
1               5                   10                  15

Phe Leu Leu Ser Val Leu Val Glu Phe Cys Tyr Gly Gly Phe Thr Ser
            20                  25                  30

Glu Tyr Val Arg Gly Ser Asp Leu Pro Asp Asp Met Pro Leu Asp Ser
        35                  40                  45

Asp Val Phe Glu Val Pro Pro Gly Pro Asn Ser Pro Gln Gln Val His
    50                  55                  60

Val Thr Gln Gly Asn His Glu Gly Asn Gly Val Ile Ile Ser Trp Val
65                  70                  75                  80

Thr Pro Val Lys Pro Gly Ser Lys Thr Val Gln Tyr Trp Cys Glu Asn
                85                  90                  95

Glu Lys Ser Arg Lys Gln Ala Glu Ala Thr Val Asn Thr Tyr Arg Phe
            100                 105                 110

Phe Asn Tyr Thr Ser Gly Tyr Ile His His Cys Leu Ile Asp Asp Leu
        115                 120                 125

Glu Phe Asp Thr Lys Tyr Tyr Tyr Glu Ile Gly Ser Gly Lys Trp Ser
    130                 135                 140

Arg Arg Phe Trp Phe Phe Ile Pro Pro Lys Ser Gly Pro Asp Val Pro
145                 150                 155                 160

Tyr Thr Phe Gly Leu Ile Gly Asp Leu Gly Gln Thr Tyr Asp Ser Asn
                165                 170                 175

Ser Thr Leu Ser His Tyr Glu Met Asn Pro Gly Lys Gly Gln Ala Val
            180                 185                 190

Leu Phe Val Gly Asp Leu Ser Tyr Ala Asp Arg Tyr Pro Asn His Asp
        195                 200                 205

Asn Asn Arg Trp Asp Thr Trp Gly Arg Phe Val Glu Arg Ser Val Ala
    210                 215                 220

Tyr Gln Pro Trp Ile Trp Thr Ala Gly Asn His Glu Ile Asp Phe Val
225                 230                 235                 240

Pro Asp Ile Gly Glu Ile Glu Pro Phe Lys Pro Phe Met Asn Arg Tyr
                245                 250                 255

His Thr Pro His Lys Ala Ser Gly Ser Ile Ser Pro Leu Trp Tyr Ser
            260                 265                 270

Ile Lys Arg Ala Ser Ala Tyr Ile Ile Val Met Ser Cys Tyr Ser Ser
        275                 280                 285

Tyr Gly Ile Tyr Thr Pro Gln Tyr Lys Trp Leu Glu Lys Glu Leu Gln
    290                 295                 300

Gly Val Asn Arg Thr Glu Thr Pro Trp Leu Ile Val Leu Val His Ser
305                 310                 315                 320

Pro Phe Tyr Ser Ser Tyr Val His His Tyr Met Glu Gly Glu Thr Leu
                325                 330                 335
```

-continued

```
Arg Val Met Tyr Glu Gln Trp Phe Val Lys Tyr Lys Val Asp Val Val
            340                 345                 350

Phe Ala Gly His Val His Ala Tyr Glu Arg Ser Glu Arg Val Ser Asn
        355                 360                 365

Ile Ala Tyr Asn Ile Val Asn Gly Leu Cys Glu Pro Ile Ser Asp Glu
    370                 375                 380

Ser Ala Pro Ile Tyr Ile Thr Ile Gly Asp Gly Gly Asn Ser Glu Gly
385                 390                 395                 400

Leu Leu Thr Asp Met Met Gln Pro Gln Pro Lys Tyr Ser Ala Phe Arg
                405                 410                 415

Glu Ala Ser Phe Gly His Gly Leu Leu Glu Ile Lys Asn Arg Thr His
            420                 425                 430

Ala Tyr Phe Ser Trp Asn Arg Asn Gln Asp Gly Asn Ala Val Ala Ala
        435                 440                 445

Asp Ser Val Trp Leu Leu Asn Arg Phe Trp Arg Ala Gln Lys Lys Thr
    450                 455                 460

Trp Leu Asp Ala Phe
465

<210> SEQ ID NO 42
<211> LENGTH: 466
<212> TYPE: PRT
<213> ORGANISM: Tagetes patula

<400> SEQUENCE: 42

Met Ala Met Gly Leu Gly Leu Gly Ser Val Tyr Leu Leu Leu Leu Cys
1               5                   10                  15

Phe Val Leu Thr Ser Cys Cys Asn Gly Gly Ile Ser Ser Ser Tyr Ser
            20                  25                  30

Arg Thr Asn Asp Ile Ser Ala Asp Met Pro Leu Asn Ser Asp Val Phe
        35                  40                  45

Ala Leu Pro His Gly Phe Asn Ala Pro Gln Gln Val His Ile Thr Gln
    50                  55                  60

Gly Asp His Glu Gly Arg Gly Val Ile Val Ser Trp Val Thr Pro Asn
65                  70                  75                  80

Glu Pro Gly Ser Ser Lys Val Ile Tyr Trp Ala Glu Asn Ser Asn Val
                85                  90                  95

Lys Gln His Ala Val Gly Ser Phe Val Thr Tyr Lys Tyr Tyr Asn Tyr
            100                 105                 110

Ser Ser Pro Tyr Ile His Cys Thr Ile Lys Asn Leu Glu Tyr Asn
        115                 120                 125

Thr Lys Tyr Phe Tyr Glu Leu Gly Thr Gly Asn Val Thr Arg Gln Phe
    130                 135                 140

Trp Phe Thr Thr Pro Pro Glu Val Gly Pro Asp Val Pro Tyr Thr Phe
145                 150                 155                 160

Gly Leu Ile Gly Asp Leu Gly Gln Thr Phe Asp Ser Asn Arg Thr Leu
                165                 170                 175

Thr His Tyr Glu Ser Asn Pro Ala Lys Gly Gln Ala Val Leu Phe Val
            180                 185                 190

Gly Asp Leu Ser Tyr Ala Asp Ala Tyr Pro Leu His Asp Asn Asn Arg
        195                 200                 205

Trp Asp Ser Trp Ala Arg Phe Val Glu Arg Ser Val Ala Tyr Gln Pro
    210                 215                 220

Trp Ile Trp Ser Ala Gly Asn His Glu Ile Asp Tyr Leu Pro Glu Tyr
225                 230                 235                 240
```

```
Gly Glu Gly Glu Pro Phe Lys Pro Tyr Thr His Arg Tyr Tyr Val Pro
            245                 250                 255

Tyr Glu Ala Pro Gly Val His Leu Arg Phe Gly Tyr Ser Ile Lys Arg
        260                 265                 270

Ala Ser Ala Tyr Ile Ile Val Met Ser Ser Tyr Ser Ala Tyr Gly Met
    275                 280                 285

Tyr Thr Pro Gln Tyr Lys Trp Leu Met Asn Glu Leu Pro Lys Val Asn
290                 295                 300

Arg Ser Glu Thr Pro Trp Leu Ile Val Val Met His Cys Pro Leu Tyr
305                 310                 315                 320

Ser Thr Tyr Leu His His Tyr Met Glu Gly Glu Thr Met Arg Val Met
                325                 330                 335

Tyr Glu Gln Tyr Phe Val Lys Tyr Lys Val Asp Val Val Phe Ser Gly
            340                 345                 350

His Val His Ala Tyr Glu Arg Thr Glu Arg Ile Ser Asn Val Ala Tyr
        355                 360                 365

Asn Ile Glu Asn Gly Leu Cys Thr Pro Arg Asn Asp Glu Tyr Ala Pro
370                 375                 380

Val Tyr Ile Thr Ile Gly Asp Gly Gly Asn Gln Glu Gly Leu Leu Tyr
385                 390                 395                 400

Glu Met Val Asp Pro Gln Pro Lys Tyr Ser Ala Phe Arg Glu Pro Ser
                405                 410                 415

Tyr Gly His Ala Thr Phe Glu Ile Lys Asn Arg Thr Thr Ala Tyr Tyr
            420                 425                 430

Ala Trp His Arg Asn Gln Asp Gly Tyr Ser Val Glu Ala Asp Ser Val
        435                 440                 445

Trp Phe His Asn Leu Tyr Trp Lys Ser Leu Ser Asp Ser Ser Ala Ala
    450                 455                 460

Ser Leu
465

<210> SEQ ID NO 43
<211> LENGTH: 473
<212> TYPE: PRT
<213> ORGANISM: Ipomoea batatas

<400> SEQUENCE: 43

Met Arg Leu Val Val Val Gly Leu Trp Cys Leu Ile Leu Gly Leu Ile
1               5                   10                  15

Leu Asn Pro Thr Lys Phe Cys Asp Ala Gly Val Thr Ser Ser Tyr Val
            20                  25                  30

Arg Lys Ser Leu Ser Ala Leu Pro Asn Ala Glu Asp Val Asp Met Pro
        35                  40                  45

Trp Asp Ser Asp Val Phe Ala Val Pro Ser Gly Tyr Asn Ala Pro Gln
    50                  55                  60

Gln Val His Ile Thr Gln Gly Asp Tyr Glu Gly Arg Gly Val Ile Ile
65                  70                  75                  80

Ser Trp Thr Thr Pro Tyr Asp Lys Ala Gly Ala Asn Lys Val Val Tyr
                85                  90                  95

Trp Ser Glu Asn Ser Lys Ser Gln Lys Arg Ala Met Gly Thr Val Val
            100                 105                 110

Thr Tyr Lys Tyr Tyr Asn Tyr Thr Ser Ala Phe Ile His His Cys Thr
        115                 120                 125

Ile Lys Asp Leu Glu Tyr Asp Thr Lys Tyr Tyr Tyr Arg Leu Gly Phe
```

```
            130                 135                 140
Gly Asp Ala Lys Arg Gln Phe Trp Phe Val Thr Pro Pro Lys Pro Gly
145                 150                 155                 160

Pro Asp Val Pro Tyr Val Phe Gly Leu Ile Gly Asp Ile Gly Gln Thr
                165                 170                 175

His Asp Ser Asn Thr Thr Leu Thr His Tyr Glu Gln Asn Ser Ala Lys
            180                 185                 190

Gly Gln Ala Val Leu Phe Met Gly Asp Leu Ser Tyr Ser Asn Arg Trp
        195                 200                 205

Pro Asn His Asp Asn Asn Arg Trp Asp Thr Trp Gly Arg Phe Ser Glu
210                 215                 220

Arg Ser Val Ala Tyr Gln Pro Trp Ile Trp Thr Ala Gly Asn His Glu
225                 230                 235                 240

Ile Asp Tyr Ala Pro Asp Ile Gly Glu Tyr Gln Pro Phe Val Pro Phe
                245                 250                 255

Thr Asn Arg Tyr Pro Thr Pro His Glu Ala Ser Gly Ser Gly Asp Pro
            260                 265                 270

Leu Trp Tyr Ala Ile Lys Arg Ala Ser Ala His Ile Ile Val Leu Ser
        275                 280                 285

Ser Tyr Ser Gly Phe Val Lys Tyr Ser Pro Gln Tyr Lys Trp Phe Thr
290                 295                 300

Ser Glu Leu Glu Lys Val Asn Arg Ser Glu Thr Pro Trp Leu Ile Val
305                 310                 315                 320

Leu Val His Ala Pro Leu Tyr Asn Ser Tyr Glu Ala His Tyr Met Glu
                325                 330                 335

Gly Glu Ala Met Arg Ala Ile Phe Glu Pro Tyr Phe Val Tyr Tyr Lys
            340                 345                 350

Val Asp Ile Val Phe Ser Gly His Val His Ser Tyr Glu Arg Ser Glu
        355                 360                 365

Arg Val Ser Asn Val Ala Tyr Asn Ile Val Asn Ala Lys Cys Thr Pro
370                 375                 380

Val Ser Asp Glu Ser Ala Pro Val Tyr Ile Thr Ile Gly Asp Gly Gly
385                 390                 395                 400

Asn Ser Glu Gly Leu Ala Ser Glu Met Thr Gln Pro Gln Pro Ser Tyr
                405                 410                 415

Ser Ala Phe Arg Glu Ala Ser Phe Gly His Gly Ile Phe Asp Ile Lys
            420                 425                 430

Asn Arg Thr His Ala His Phe Ser Trp His Arg Asn Gln Asp Gly Ala
        435                 440                 445

Ser Val Glu Ala Asp Ser Leu Trp Leu Leu Asn Arg Tyr Trp Ala Ser
450                 455                 460

Glu Asp Ala Ser Ser Met Ser Ala Met
465                 470

<210> SEQ ID NO 44
<211> LENGTH: 459
<212> TYPE: PRT
<213> ORGANISM: Phaseolus vulgaris

<400> SEQUENCE: 44

Met Gly Val Val Lys Gly Leu Leu Ala Leu Ala Leu Val Leu Asn Val
 1               5                  10                  15

Val Val Val Ser Asn Gly Gly Lys Ser Ser Asn Phe Val Arg Lys Thr
            20                  25                  30
```

-continued

```
Asn Lys Asn Arg Asp Met Pro Leu Asp Ser Asp Val Phe Arg Val Pro
     35                  40                  45

Pro Gly Tyr Asn Ala Pro Gln Gln Val His Ile Thr Gln Gly Asp Leu
 50                  55                  60

Val Gly Arg Ala Met Ile Ile Ser Trp Val Thr Met Asp Glu Pro Gly
 65                  70                  75                  80

Ser Ser Ala Val Arg Tyr Trp Ser Glu Lys Asn Gly Arg Lys Arg Ile
                 85                  90                  95

Ala Lys Gly Lys Met Ser Thr Tyr Arg Phe Phe Asn Tyr Ser Ser Gly
            100                 105                 110

Phe Ile His His Thr Thr Ile Arg Lys Leu Lys Tyr Asn Thr Lys Tyr
            115                 120                 125

Tyr Tyr Glu Val Gly Leu Arg Asn Thr Thr Arg Phe Ser Phe Ile
            130                 135                 140

Thr Pro Pro Gln Thr Gly Leu Asp Val Pro Tyr Thr Phe Gly Leu Ile
145                 150                 155                 160

Gly Asp Leu Gly Gln Ser Phe Asp Ser Asn Thr Thr Leu Ser His Tyr
                165                 170                 175

Glu Leu Ser Pro Lys Lys Gly Gln Thr Val Leu Phe Val Gly Asp Leu
            180                 185                 190

Ser Tyr Ala Asp Arg Tyr Pro Asn His Asp Asn Val Arg Trp Asp Thr
            195                 200                 205

Trp Gly Arg Phe Thr Glu Arg Ser Val Ala Tyr Gln Pro Trp Ile Trp
            210                 215                 220

Thr Ala Gly Asn His Glu Ile Glu Phe Ala Pro Glu Ile Asn Glu Thr
225                 230                 235                 240

Glu Pro Phe Lys Pro Phe Ser Tyr Arg Tyr His Val Pro Tyr Glu Ala
                245                 250                 255

Ser Gln Ser Thr Ser Pro Phe Trp Tyr Ser Ile Lys Arg Ala Ser Ala
            260                 265                 270

His Ile Ile Val Leu Ser Ser Tyr Ser Ala Tyr Gly Arg Gly Thr Pro
            275                 280                 285

Gln Tyr Thr Trp Leu Lys Lys Glu Leu Arg Lys Val Lys Arg Ser Glu
            290                 295                 300

Thr Pro Trp Leu Ile Val Leu Met His Ser Pro Leu Tyr Asn Ser Tyr
305                 310                 315                 320

Asn His His Phe Met Glu Gly Glu Ala Met Arg Thr Lys Phe Glu Ala
                325                 330                 335

Trp Phe Val Lys Tyr Lys Val Asp Val Val Phe Ala Gly His Val His
            340                 345                 350

Ala Tyr Glu Arg Ser Glu Arg Val Ser Asn Ile Ala Tyr Lys Ile Thr
            355                 360                 365

Asn Gly Leu Cys Thr Pro Val Lys Asp Gln Ser Ala Pro Val Tyr Ile
            370                 375                 380

Thr Ile Gly Asp Ala Gly Asn Tyr Gly Val Ile Asp Ser Asn Met Ile
385                 390                 395                 400

Gln Pro Gln Pro Glu Tyr Ser Ala Phe Arg Glu Ala Ser Phe Gly His
                405                 410                 415

Gly Met Phe Asp Ile Lys Asn Arg Thr His Ala His Phe Ser Trp Asn
            420                 425                 430

Arg Asn Gln Asp Gly Val Ala Val Glu Ala Asp Ser Val Trp Phe Phe
            435                 440                 445

Asn Arg His Trp Tyr Pro Val Asp Asp Ser Thr
```

<210> SEQ ID NO 45
<211> LENGTH: 432
<212> TYPE: PRT
<213> ORGANISM: Phaseolus vulgaris

<400> SEQUENCE: 45

```
Phe Val Arg Lys Thr Asn Lys Asn Arg Asp Met Pro Leu Asp Ser Asp
  1               5                  10                  15
Val Phe Arg Val Pro Pro Gly Tyr Asn Ala Pro Gln Gln Val His Ile
                 20                  25                  30
Thr Gln Gly Asp Leu Val Gly Arg Ala Met Ile Ile Ser Trp Val Thr
             35                  40                  45
Met Asp Glu Pro Gly Ser Ser Ala Val Arg Tyr Trp Ser Glu Lys Asn
         50                  55                  60
Gly Arg Lys Arg Ile Ala Lys Gly Lys Met Ser Thr Tyr Arg Phe Phe
 65                  70                  75                  80
Asn Tyr Ser Ser Gly Phe Ile His His Thr Thr Ile Arg Lys Leu Lys
                 85                  90                  95
Tyr Asn Thr Lys Tyr Tyr Tyr Glu Val Gly Leu Arg Asn Thr Thr Arg
            100                 105                 110
Arg Phe Ser Phe Ile Thr Pro Pro Gln Thr Gly Leu Asp Val Pro Tyr
        115                 120                 125
Thr Phe Gly Leu Ile Gly Asp Leu Gly Gln Ser Phe Asp Ser Asn Thr
    130                 135                 140
Thr Leu Ser His Tyr Glu Leu Ser Pro Lys Lys Gly Gln Thr Val Leu
145                 150                 155                 160
Phe Val Gly Asp Leu Ser Tyr Ala Asp Arg Tyr Pro Asn His Asp Asn
                165                 170                 175
Val Arg Trp Asp Thr Trp Gly Arg Phe Thr Glu Arg Ser Val Ala Tyr
            180                 185                 190
Gln Pro Trp Ile Trp Thr Ala Gly Asn His Glu Ile Glu Phe Ala Pro
        195                 200                 205
Glu Ile Asn Glu Thr Glu Pro Phe Lys Pro Phe Ser Tyr Arg Tyr His
    210                 215                 220
Val Pro Tyr Glu Ala Ser Gln Ser Thr Ser Pro Phe Trp Tyr Ser Ile
225                 230                 235                 240
Lys Arg Ala Ser Ala His Ile Ile Val Leu Ser Ser His Ile Ala Tyr
                245                 250                 255
Gly Arg Gly Thr Pro Gln Tyr Thr Trp Leu Lys Lys Glu Leu Arg Lys
            260                 265                 270
Val Lys Arg Ser Glu Thr Pro Trp Leu Ile Val Leu Met His Ser Pro
        275                 280                 285
Leu Tyr Asn Ser Tyr Asn His His Phe Met Glu Gly Glu Ala Met Arg
    290                 295                 300
Thr Lys Phe Glu Ala Trp Phe Val Lys Tyr Lys Val Asp Val Val Phe
305                 310                 315                 320
Ala Gly His Val His Ala Tyr Glu Arg Ser Glu Arg Val Ser Asn Ile
                325                 330                 335
Ala Tyr Lys Ile Thr Asp Gly Leu Cys Thr Pro Val Lys Asp Gln Ser
            340                 345                 350
Ala Pro Val Tyr Ile Thr Ile Gly Asp Ala Gly Asn Tyr Gly Val Ile
        355                 360                 365
```

```
Asp Ser Asn Met Ile Gln Pro Gln Pro Glu Tyr Ser Ala Phe Arg Glu
    370                 375                 380

Ala Ser Phe Gly His Gly Met Phe Asp Ile Lys Asn Arg Thr His Ala
385                 390                 395                 400

His Phe Ser Trp Asn Arg Asn Gln Asp Gly Val Ala Val Glu Ala Asp
                405                 410                 415

Ser Val Trp Phe Phe Asn Arg His Trp Tyr Pro Val Asp Asp Ser Thr
                420                 425                 430

<210> SEQ ID NO 46
<211> LENGTH: 463
<212> TYPE: PRT
<213> ORGANISM: Lupinus luteus

<400> SEQUENCE: 46

Met Lys Met Gly Asn Ser Ser Phe Val Ala Ile Ala Leu Leu Met Ser
  1               5                  10                  15

Val Val Val Leu Cys Asn Gly Gly Lys Thr Ser Ser Tyr Val Arg Lys
                 20                  25                  30

Leu Ile Gln Asn Pro Val Asp Met Pro Leu Asp Ser Asp Ala Phe Ala
             35                  40                  45

Ile Pro Pro Gly Tyr Asn Ala Pro Gln Gln Val His Ile Thr Gln Gly
         50                  55                  60

Asp His Val Gly Gln Ala Met Ile Ile Ser Trp Val Thr Val Asp Glu
 65                  70                  75                  80

Pro Gly Ser Asn Glu Val Ile Tyr Trp Ser Asn Ser Ser Leu Gln Asn
                 85                  90                  95

Phe Thr Ala Glu Gly Glu Val Phe Thr Tyr Thr Tyr Asn Tyr Thr
                100                 105                 110

Ser Gly Phe Ile His His Thr Asn Ile Thr Asn Leu Glu Phe Asn Thr
            115                 120                 125

Thr Tyr Phe Tyr Val Val Gly Ile Gly Asn Thr Thr Arg Gln Phe Trp
130                 135                 140

Phe Ile Thr Pro Pro Glu Val Gly Ile Asn Val Pro Tyr Thr Phe Gly
145                 150                 155                 160

Ile Ile Gly Asp Leu Gly Gln Thr Phe Asp Ser Asn Thr Thr Leu Thr
                165                 170                 175

His Tyr Gln Asn Ser Lys Gly Asn Thr Leu Leu Tyr Val Gly Asp Leu
            180                 185                 190

Ser Tyr Ala Asp Asn Tyr Pro Asn His Asp Asn Val Arg Trp Asp Thr
        195                 200                 205

Trp Gly Arg Phe Ile Glu Arg Ser Ala Ala Tyr Gln Pro Trp Ile Trp
210                 215                 220

Thr Ala Gly Asn His Glu Ile Asp Phe Asp Pro Gln Ile Gly Glu Thr
225                 230                 235                 240

Gln Pro Phe Lys Pro Phe Ser Asn Arg Tyr His Thr Pro Tyr Val Ala
                245                 250                 255

Ser Gln Ser Thr Glu Pro Tyr Tyr Ser Ile Lys Arg Gly Pro Ala
            260                 265                 270

His Ile Ile Val Leu Ala Ser Tyr Ser Ala Tyr Gly Thr Ser Ser Leu
        275                 280                 285

Gln Tyr Lys Trp Leu Thr Ser Glu Leu Pro Lys Val Asp Arg Thr Lys
    290                 295                 300

Thr Ser Trp Leu Ile Val Leu Met His Ala Pro Trp Tyr Asn Ser Tyr
305                 310                 315                 320
```

```
Tyr Ser His Tyr Met Glu Gly Glu Pro Met Arg Val Val Phe Glu Ser
            325                 330                 335
Leu Phe Val Lys Tyr Lys Gly Asp Val Val Phe Ala Gly His Val His
            340                 345                 350
Ala Tyr Glu Arg Pro Glu Arg Val Ser Asn Asp Lys Tyr Asn Ile Thr
            355                 360                 365
Asn Gly Ile Cys Thr Pro Val Lys Asp Ile Ser Ala Pro Val Tyr Ile
            370                 375                 380
Thr Asn Gly Asp Gly Gly Asn Gln Glu Gly Leu Ser Ile Asn Met Thr
385                 390                 395                 400
Gln Pro Gln Pro Ser Tyr Ser Ala Tyr Arg Glu Ala Ser Phe Gly His
            405                 410                 415
Gly Thr Leu Glu Ile Lys Asn Arg Thr His Ala His Tyr Ser Trp Asn
            420                 425                 430
Arg Asn Gln Asp Gly Tyr Ala Val Glu Ala Asp Lys Leu Trp Leu Phe
            435                 440                 445
Asn Arg Tyr Trp Asn Pro Arg Asp Asp Ser Thr Ile His Ile Pro
            450                 455                 460

<210> SEQ ID NO 47
<211> LENGTH: 462
<212> TYPE: PRT
<213> ORGANISM: Lupinus albus

<400> SEQUENCE: 47

Met Lys Met Gly Tyr Ser Ser Phe Val Ala Ile Ala Leu Leu Met Ser
  1               5                  10                  15
Val Val Val Cys Asn Gly Gly Lys Thr Ser Thr Tyr Val Arg Asn
                 20                  25                  30
Leu Ile Glu Lys Pro Val Asp Met Pro Leu Asp Ser Asp Ala Phe Ala
             35                  40                  45
Ile Pro Pro Gly Tyr Asn Ala Pro Gln Gln Val His Ile Thr Gln Gly
         50                  55                  60
Asp Leu Val Gly Gln Ala Met Ile Ile Ser Trp Val Thr Val Asp Glu
 65                  70                  75                  80
Pro Gly Ser Asn Gln Val Ile Tyr Trp Ser Asp Ser Ser Leu Gln Asn
                 85                  90                  95
Phe Thr Ala Glu Gly Glu Val Phe Thr Tyr Thr Tyr Asn Tyr Thr
            100                 105                 110
Ser Gly Phe Ile His His Thr Thr Ile Thr Asn Leu Glu Phe Asp Thr
            115                 120                 125
Thr Tyr Tyr Tyr Glu Val Gly Ile Gly Asn Thr Thr Arg Gln Phe Trp
            130                 135                 140
Phe Ile Thr Pro Pro Glu Val Gly Leu Asp Val Pro Tyr Thr Phe Gly
145                 150                 155                 160
Ile Ile Gly Asp Leu Gly Gln Thr Phe Asp Ser Asn Thr Thr Leu Thr
                165                 170                 175
His Tyr Gln Asn Ser Asn Gly Thr Ala Leu Leu Tyr Val Gly Asp Leu
            180                 185                 190
Ser Tyr Ala Asp Tyr Pro Tyr His Asp Asn Val Arg Trp Asp Thr
            195                 200                 205
Trp Gly Arg Phe Thr Glu Arg Ser Ala Ala Tyr Gln Pro Trp Ile Trp
            210                 215                 220
Thr Ala Gly Asn His Glu Ile Asp Phe Asp Leu Gln Ile Gly Glu Thr
```

-continued

```
                225                 230                 235                 240
Gln Pro Phe Lys Pro Phe Ser Thr Arg Tyr His Thr Pro Tyr Glu Ala
                245                 250                 255
Ser Gln Ser Thr Glu Pro Phe Tyr Tyr Ser Ile Lys Arg Gly Pro Ala
                260                 265                 270
His Val Ile Val Leu Ala Thr Tyr Ser Ala Phe Gly Tyr Ser Thr Leu
                275                 280                 285
Gln Tyr Lys Trp Leu Thr Ala Glu Leu Pro Lys Val Asn Arg Ser Glu
                290                 295                 300
Thr Ser Trp Leu Ile Val Leu Met His Ala Pro Trp Tyr Asn Ser Tyr
305                 310                 315                 320
Asn Asn His Tyr Met Glu Gly Glu Pro Met Arg Val Ile Tyr Glu Ser
                325                 330                 335
Leu Phe Leu Lys Tyr Lys Val Asp Val Phe Ala Gly His Val His
                340                 345                 350
Ala Tyr Glu Arg Ser Glu Arg Val Ser Asn Asn Lys Tyr Asn Ile Thr
                355                 360                 365
Asn Gly Ile Cys Thr Pro Val Lys Asp Ile Thr Ala Pro Ile Tyr Ile
370                 375                 380
Thr Asn Gly Asp Gly Gly Asn Leu Glu Gly Leu Ala Thr Met Lys Gln
385                 390                 395                 400
Pro Gln Pro Ser Tyr Ser Ala Tyr Arg Glu Ala Ser Phe Gly His Gly
                405                 410                 415
Ile Phe Ala Ile Lys Asn Arg Thr His Ala His Tyr Ser Trp Asn Arg
                420                 425                 430
Asn Gln Asp Gly Tyr Ala Val Glu Ala Asp Lys Leu Trp Leu Phe Asn
                435                 440                 445
Arg Tyr Trp Asn Pro Leu Asn Asp Ser Thr Ile His Ile Pro
450                 455                 460

<210> SEQ ID NO 48
<211> LENGTH: 460
<212> TYPE: PRT
<213> ORGANISM: Lupinus albus

<400> SEQUENCE: 48

Met Gly Tyr Ser Ser Phe Val Ala Ile Ala Leu Leu Met Ser Val Val
  1               5                  10                  15
Val Val Cys Asn Gly Gly Lys Thr Ser Thr Tyr Val Arg Asn Leu Ile
                 20                  25                  30
Glu Lys Pro Val Asp Met Pro Leu Asp Ser Asp Ala Phe Ala Ile Pro
                 35                  40                  45
Pro Gly Tyr Asn Ala Pro Gln Gln Val His Ile Thr Gln Gly Asp Leu
             50                  55                  60
Val Gly Gln Ala Met Ile Ile Ser Trp Val Thr Val Asp Glu Pro Gly
 65                  70                  75                  80
Ser Asn Gln Val Ile Tyr Trp Ser Asp Ser Ser Leu Gln Asn Phe Thr
                 85                  90                  95
Ala Glu Gly Glu Val Phe Thr Tyr Thr Tyr Asn Tyr Thr Ser Gly
                100                 105                 110
Phe Ile His His Thr Thr Ile Thr Asn Leu Glu Phe Asp Thr Thr Tyr
             115                 120                 125
Tyr Tyr Glu Val Gly Ile Gly Asn Thr Thr Arg Gln Phe Trp Phe Ile
         130                 135                 140
```

```
Thr Pro Pro Glu Val Gly Leu Asp Val Pro Tyr Thr Phe Gly Ile Ile
145                 150                 155                 160

Gly Asp Leu Gly Gln Thr Phe Asp Ser Asn Thr Thr Leu Thr His Tyr
            165                 170                 175

Gln Asn Ser Asn Gly Thr Ala Leu Leu Tyr Val Gly Asp Leu Ser Tyr
        180                 185                 190

Ala Asp Asp Tyr Pro Tyr His Asp Asn Val Arg Trp Asp Thr Trp Gly
        195                 200                 205

Arg Phe Thr Glu Arg Ser Ala Ala Tyr Gln Pro Trp Ile Trp Thr Ala
210                 215                 220

Gly Asn His Glu Ile Asp Phe Asp Leu Gln Ile Gly Glu Thr Gln Pro
225                 230                 235                 240

Phe Lys Pro Phe Ser Thr Arg Tyr His Thr Pro Tyr Glu Ala Ser Gln
                245                 250                 255

Ser Thr Glu Pro Phe Tyr Tyr Ser Ile Lys Arg Gly Pro Ala His Val
            260                 265                 270

Ile Val Leu Ala Thr Tyr Ser Ala Phe Gly Tyr Ser Thr Leu Gln Tyr
        275                 280                 285

Lys Trp Leu Thr Ala Glu Leu Pro Lys Val Asn Arg Ser Glu Thr Ser
290                 295                 300

Trp Leu Ile Val Leu Met His Ala Pro Trp Tyr Asn Ser Ser Asn Asn
305                 310                 315                 320

His Tyr Met Glu Gly Glu Pro Met Arg Val Ile Tyr Glu Ser Leu Phe
                325                 330                 335

Leu Lys Tyr Lys Val Asp Val Val Phe Ala Gly His Val His Ala Tyr
            340                 345                 350

Glu Arg Ser Glu Arg Val Ser Asn Asn Lys Tyr Asn Ile Thr Asn Gly
        355                 360                 365

Ile Cys Thr Pro Val Glu Asp Ile Thr Ala Pro Ile Tyr Ile Thr Asn
370                 375                 380

Gly Asp Gly Gly Asn Leu Glu Gly Leu Ala Thr Met Lys Gln Pro Gln
385                 390                 395                 400

Pro Ser Tyr Ser Ala Tyr Arg Lys Ala Ser Phe Gly His Gly Ile Phe
                405                 410                 415

Ala Ile Lys Asn Arg Thr His Ala His Tyr Ser Trp Asn Arg Asn Gln
            420                 425                 430

Asp Gly Tyr Ala Val Glu Ala Asp Lys Leu Trp Leu Phe Asn Arg Tyr
        435                 440                 445

Trp Asn Pro Leu Asn Asp Ser Thr Ile His Ile Pro
450                 455                 460

<210> SEQ ID NO 49
<211> LENGTH: 638
<212> TYPE: PRT
<213> ORGANISM: Lupinus albus

<400> SEQUENCE: 49

Met Gly Tyr Tyr Ser Ile Tyr Cys Leu Ile Val Leu Val Asn Val Leu
1               5                   10                  15

Val Phe Cys Asp Gly Gly Lys Thr Ser Ser Phe Val Arg Glu Ser Glu
            20                  25                  30

Arg Ala Ile Asp Met Ala Leu Asp Ser Asp Val Phe His Val Pro Arg
        35                  40                  45

Gly Tyr Asn Ala Pro Gln Gln Val His Ile Thr Gln Gly Asp Leu Val
    50                  55                  60
```

```
Gly Lys Ala Val Ile Val Ser Trp Val Thr Val Asp Glu Pro Gly Ser
 65                  70                  75                  80

Thr Lys Val Ser Tyr Trp Ser Asp Lys His Ser His Asp Lys Lys Ser
                 85                  90                  95

Ala His Gly Lys Ile Val Thr Tyr Arg Phe Phe Asn Tyr Thr Ser Gly
            100                 105                 110

Phe Ile His His Thr Ile Lys His Leu Lys Tyr Thr Thr Lys Tyr His
            115                 120                 125

Tyr Glu Val Gly Ser Trp Asn Thr Thr Arg His Phe Trp Val Tyr Asn
130                 135                 140

Phe Pro Ile Gln Phe Gly Leu Asp Val Pro Cys Thr Phe Gly Leu Ile
145                 150                 155                 160

Gly Asp Leu Gly Gln Thr Phe Asp Ser Asn Gln Thr Leu Thr His Tyr
                165                 170                 175

Gln His Asn Pro Arg Lys Gly Gln Ala Val Leu Tyr Val Gly Asp Leu
            180                 185                 190

Ser Tyr Ala Asp Asn Tyr Pro Asn His Asp Asn Val Arg Trp Asp Thr
            195                 200                 205

Trp Gly Arg Phe Thr Glu Arg Val Ala Tyr Gln Pro Trp Ile Trp
210                 215                 220

Thr Ala Gly Asn His Glu Leu Asp Phe Val Pro Glu Ile Gly Glu Thr
225                 230                 235                 240

Lys Pro Phe Lys Pro Phe Thr His Arg Tyr Pro Val Pro Phe Lys Pro
                245                 250                 255

Ser Glu Ser Thr Glu Pro Phe Trp Tyr Ser Ile Lys Arg Gly Pro Ala
            260                 265                 270

His Val Ile Val Leu Ala Ser Tyr Lys Ala Tyr Gly Lys Tyr Thr Pro
            275                 280                 285

Gln Tyr Gln Trp Leu Glu Ala Glu Leu Pro Lys Pro Lys Val Asn Arg
290                 295                 300

Lys Glu Thr Pro Trp Leu Ile Val Leu Val His Ser Pro Trp Tyr Asn
305                 310                 315                 320

Ser Tyr Asn Tyr His Phe Met Glu Gly Glu Thr Met Arg Val Met Phe
                325                 330                 335

Glu Ser Trp Leu Val Gln Tyr Lys Val Asp Val Phe Ala Gly His
            340                 345                 350

Val His Ala Tyr Glu Arg Ser Glu Cys Val Ser Asn Val Glu Val Arg
            355                 360                 365

His Cys Lys Trp Gln Val Tyr Pro Cys Lys Asp Gln Ser Ala Pro Val
370                 375                 380

Tyr Ile Thr Ile Gly Asp Gly Gly Asn Ile Glu Gly Leu Ala Asn Asn
385                 390                 395                 400

Met Thr Glu Pro Gln Pro Lys Tyr Ser Ala Tyr Arg Glu Ala Ser Phe
                405                 410                 415

Gly His Ala Ile Phe Asp Ile Lys Asn Arg Thr Val Leu Gly Leu Phe
            420                 425                 430

Ser Glu Asn Tyr Arg Leu His Thr Lys Gln Glu Glu Asp Glu Lys Asn
            435                 440                 445

Leu Ala Ser Lys Gly Ala Met Val Lys Gly Val Ile Leu Gln Gln Val
            450                 455                 460

Val Gln Ala Val Val Ala Thr Leu Leu Phe Ala Val Thr Gly Asn Asp
465                 470                 475                 480
```

```
Ser Gln Asp Thr Asn Gln Asn Ala Ser Leu Leu Val Ser Ala Arg Gln
                485                 490                 495

Phe Val Ile Ala Met Leu Val Ile Asp Thr Trp Gln Tyr Phe Met His
            500                 505                 510

Arg Tyr Met His His Asn Lys Phe Leu Tyr Lys His Ile His Ser Gln
            515                 520                 525

His His Arg Leu Ile Val Pro Tyr Ser Phe Gly Ala Leu Tyr Asn His
            530                 535                 540

Pro Leu Val Gly Leu Ile Leu Asp Thr Ile Gly Gly Ala Leu Ser Phe
545                 550                 555                 560

Leu Ile Ser Gly Met Ser Pro Arg Ile Ser Ile Phe Phe Ser Phe
                565                 570                 575

Ala Thr Ile Lys Thr Val Asp Asp His Cys Gly Leu Trp Leu Pro Gly
            580                 585                 590

Asn Leu Phe His Ile Phe Ser Thr Thr Ile Leu Leu Thr Met Met Phe
            595                 600                 605

Thr Ile Ser Phe Ser Ala Thr Ser Thr Thr Thr His Ser His Ser Leu
            610                 615                 620

Leu Cys Gly Ile Lys Ser Trp Val Pro Thr Cys Leu Thr His
625                 630                 635

<210> SEQ ID NO 50
<211> LENGTH: 348
<212> TYPE: PRT
<213> ORGANISM: Arabidopsis thaliana

<400> SEQUENCE: 50

Met Leu Trp Phe Phe Leu Leu Gln Tyr Asp Thr Lys Tyr Tyr Val
1               5                   10                  15

Leu Gly Val Gly Gln Thr Glu Arg Lys Phe Trp Phe Thr Pro Pro
            20                  25                  30

Glu Ile Gly Pro Asp Val Pro Tyr Thr Phe Gly Leu Ile Gly Asp Leu
            35                  40                  45

Gly Gln Ser Tyr Asp Ser Asn Ile Thr Leu Thr His Tyr Glu Asn Asn
        50                  55                  60

Pro Thr Lys Gly Gln Ala Val Leu Phe Val Gly Asp Ile Ser Tyr Ala
65                  70                  75                  80

Asp Thr Tyr Pro Asp His Asp Asn Arg Arg Trp Asp Ser Trp Gly Arg
                85                  90                  95

Phe Ala Glu Arg Ser Thr Ala Tyr Gln Pro Trp Ile Trp Thr Thr Gly
            100                 105                 110

Asn His Glu Leu Asp Phe Ala Pro Glu Ile Gly Glu Asn Arg Pro Phe
            115                 120                 125

Lys Pro Phe Thr His Arg Tyr Arg Thr Pro Tyr Arg Ser Ser Gly Ser
130                 135                 140

Thr Glu Pro Phe Trp Tyr Ser Ile Lys Arg Gly Pro Ala Tyr Ile Ile
145                 150                 155                 160

Val Leu Ala Ser Tyr Ser Ala Tyr Gly Lys Tyr Thr Pro Gln Tyr Gln
                165                 170                 175

Trp Leu Glu Glu Glu Phe Pro Lys Val Asn Arg Thr Glu Thr Pro Trp
            180                 185                 190

Leu Ile Val Leu Met His Ser Pro Trp Tyr Asn Ser Tyr Asp Tyr His
            195                 200                 205

Tyr Met Glu Gly Glu Thr Met Arg Val Met Tyr Glu Ala Trp Phe Val
        210                 215                 220
```

Lys Tyr Lys Val Asp Val Val Phe Ala Gly His Val His Ala Tyr Glu
225                 230                 235                 240

Arg Ser Glu Arg Val Ser Asn Ile Ala Tyr Asn Val Val Asn Gly Ile
            245                 250                 255

Cys Thr Pro Val Lys Asp Gln Ser Ala Pro Val Tyr Ile Thr Ile Gly
            260                 265                 270

Asp Gly Gly Asn Ile Glu Gly Leu Ala Thr Lys Met Thr Glu Pro Gln
            275                 280                 285

Pro Lys Tyr Ser Ala Phe Arg Glu Ala Ser Phe Gly His Ala Ile Phe
            290                 295                 300

Ser Ile Lys Asn Arg Thr His Ala His Tyr Gly Trp His Arg Asn His
305                 310                 315                 320

Asp Gly Tyr Ala Val Glu Gly Asp Arg Met Trp Phe Tyr Asn Arg Phe
                325                 330                 335

Trp His Pro Val Asp Asp Ser Pro Ser Cys Asn Ser
            340                 345

<210> SEQ ID NO 51
<211> LENGTH: 348
<212> TYPE: PRT
<213> ORGANISM: Arabidopsis thaliana

<400> SEQUENCE: 51

Met Leu Trp Phe Phe Leu Leu Gln Tyr Asp Thr Lys Tyr Tyr Tyr Val
1               5                   10                  15

Leu Gly Val Gly Gln Thr Glu Arg Lys Phe Trp Phe Thr Pro Pro
            20                  25                  30

Glu Ile Gly Pro Asp Val Pro Tyr Thr Phe Gly Leu Ile Gly Asn Leu
        35                  40                  45

Gly Gln Ser Tyr Asp Ser Asn Ile Thr Leu Thr His Tyr Glu Asn Asn
    50                  55                  60

Pro Thr Lys Gly Gln Ala Val Leu Phe Val Gly Asp Ile Ser Tyr Ala
65                  70                  75                  80

Asp Thr Tyr Pro Asp His Asp Asn Arg Arg Trp Asp Ser Trp Gly Arg
                85                  90                  95

Phe Ala Glu Arg Ser Thr Ala Tyr Gln Pro Trp Ile Trp Thr Thr Gly
            100                 105                 110

Asn His Glu Leu Asp Phe Ala Pro Glu Ile Gly Glu Asn Arg Pro Phe
        115                 120                 125

Lys Pro Phe Thr His Arg Tyr Arg Thr Pro Tyr Arg Ser Ser Gly Ser
    130                 135                 140

Thr Glu Pro Phe Trp Tyr Ser Ile Lys Arg Gly Pro Ala Tyr Ile Val
145                 150                 155                 160

Val Leu Ala Ser Tyr Ser Ala Tyr Gly Lys Tyr Thr Pro Gln Tyr Gln
                165                 170                 175

Trp Leu Glu Glu Glu Phe Pro Lys Val Asn Arg Thr Glu Thr Pro Trp
            180                 185                 190

Leu Ile Val Leu Met His Ser Pro Trp Tyr Asn Ser Tyr Asp Tyr His
        195                 200                 205

Tyr Met Glu Gly Glu Thr Met Arg Val Met Tyr Glu Ala Trp Phe Val
    210                 215                 220

Lys Tyr Lys Val Asp Val Val Phe Ala Gly His Val His Ala Tyr Glu
225                 230                 235                 240

Arg Ser Glu Arg Val Ser Asn Ile Ala Tyr Asn Val Val Asn Gly Ile
                245                 250                 255

-continued

```
                        245                     250                     255
Cys Thr Pro Val Lys Asp Gln Ser Ala Pro Val Tyr Ile Thr Ile Gly
            260                     265                     270

Asp Gly Gly Asn Ile Glu Gly Leu Ala Thr Lys Met Thr Glu Pro Gln
            275                     280                     285

Pro Lys Tyr Ser Ala Phe Arg Glu Ala Ser Phe Gly His Ala Ile Phe
    290                     295                     300

Ser Ile Lys Asn Arg Thr His Ala His Tyr Gly Trp His Arg Asn His
305                     310                     315                     320

Gly Gly Tyr Ala Val Glu Gly Asp Arg Met Trp Phe Tyr Asn Arg Phe
            325                     330                     335

Trp His Pro Val Asp Asp Ser Pro Ser Cys Asn Ser
            340                     345
```

US 7,417,181 B2

PLANTS WITH INCREASED PHOSPHOROUS UPTAKE

This application claims the priority of U.S. Provisional Appl. Ser. No. 60/669,242 filed Apr. 7, 2005 and U.S. Provisional Appl. Ser. No. 60/669,275, filed Apr. 7, 2005, the entire disclosures of which are incorporated herein by reference.

BACKGROUND OF THE INVENTION

1. Field of the Invention

The present invention relates generally to the field of molecular biology. More specifically, the invention relates to plant genes involved in phosphorous uptake and methods of use thereof.

2. Description of the Related Art

Phosphate (Pi) is one of the key substrates in energy metabolism and biosynthesis of nucleic acids and membranes. It also plays an important role in photosynthesis, respiration and regulation of a number of enzymes (Raghothama, 1999). While it is a critical macronutrient for plant growth and development, most of the total soil phosphorus (P) is not available for uptake due to its rapid immobilization by soil organic and inorganic components (Von Uexküll and Mutert, 1995; Whitelaw, 2000). Phosphorus is limiting for crop yield on over 30% of the world's arable land, and by some estimates, world resources of inexpensive rock phosphate may be depleted by 2050 (Vance et al., 2003). The lack of inexpensive P has been recognized as a potential future crisis in agriculture (Abelson, 1999). In consideration of the trend toward sustainability and environmental stewardship, P has been a key nutrient in maintaining long-term productivity of agricultural systems (Iyamuremye and Dick, 1996).

Organic phosphorus plays a vital role in the P cycle of agricultural soils (Dalal, 1977). Anywhere from 30% to 80% of soil P occurs in organic form, which, after mineralization, can contribute considerably to the P nutrition of plants (Bieleski, 1973; Dalal, 1977). Natural efficient acquisition and utilization of organic phosphorus requires a class of endogenous enzymes known as phosphatases (Duff et al., 1994). Acid phosphatase are one form of phosphatase capable of hydrolysing P from orthophosphate monoesters (Duff et al., 1994). One of the adaptive changes of plants under low-Pi conditions is the increased synthesis and secretion of APases (Goldstein et al., 1988; Goldstein et al., 1988; Wasaki et al., 1999; Haran et al., 2000; Wasaki et al., 2000). Plant APases are involved in many biological processes such as providing P during seed germination from stored phytate, internal remobilization of P, release of P from soil organic P-esters and the synthesis of glycolate from P-glycolate (Vance et al., 2003). However, the relative importance of these enzymes for plant P nutrition has yet to be determined (Tomscha et al., 2004).

Although many acid phosphatase genes have been identified in plants based on sequence analysis (Schenk et al., 2000; Li et al., 2002), only a limited number of APase genes have been characterized in any detail (del Pozo et al., 1999; Wasaki et al., 1999; Haran et al., 2000; Baldwin et al., 2001; Miller et al., 2001). The type 5 APase gene (AtACP5) from *Arabidopsis* (del Pozo et al., 1999) and a Pi starvation-induced APase gene (LePS2) from tomato (Baldwin et al., 2001) were implicated in internal P remobilization. The two genes were highly inducible in roots and shoots under Pi-deficient conditions, while no accumulation of transcripts was detected in either roots or shoots under Pi-sufficient conditions (del Pozo et al., 1999; Baldwin et al., 2001). The transcript of the membrane-bound form of APases (LASAP1) from white lupin (Wasaki et al., 1999) was detected at its highest levels in roots and shoots under Pi-deficient conditions, although much lower levels of transcript were also detectable in roots and shoots under Pi-sufficient conditions (Wasaki et al., 1999; Miller et al., 2001). The mRNAs of the secretory forms of APase from white lupin were only detectable in roots under Pi-deficient conditions, while no transcript was detected in roots and shoots under Pi-sufficient conditions (Wasaki et al., 2000; Miller et al., 2001; Wasaki et al., 2003).

Due to the general phenomenon of APase secretion under P stress and the positive correlation between APase activity and P uptake reported in some studies (Goldstein et al., 1988; Helal, 1990; Asmar et al., 1995; Haran et al., 2000; Wasaki et al., 2000), the role of increased secretion of APase to liberate P from organic sources in the soil has been discussed (Tarafdar and Claassen, 1988; Duff et al., 1994). However, some comparative studies between genotypes or recombinant lines have produced results showing a negative or no relationship between root APase activity and P uptake under Pi stress (McLachlan, 1980; Hunter and McManus, 1999; Yan et al., 2001). For example, it has been shown that a major gene contributing to APase activity in common bean was not associated with P acquisition efficiency and P use efficiency (Yan et al., 2001).

The conflicting results may be due to substantial heterogeneity among APases with regards to their kinetic properties and subcellular locations, and various APases may have distinct metabolic functions. As pointed out by Duff et al. (1994), the diversity and ubiquity of plant APases make a consensus on their precise physiological and biochemical roles difficult to achieve. Perhaps because of this, there has not been any report on improving P uptake by overexpression of plant APase.

While the studies to date have furthered understanding of phosphorous utilization, methods for increasing soil phosphorous uptake have been lacking. There is a great need for the identification of such methods due to the depletion of natural phosphorous sources and because of the significant deleterious effects of phosphorous depletion on agricultural productivity. Applications of phosphorous-rich fertilizers can also create run off polluting water sources. The identification of methods of increasing phosphorous uptake would therefore represent a significant benefit to agriculture and the environment alike.

SUMMARY OF THE INVENTION

In one aspect, the invention provides an isolated nucleic acid sequence encoding a plant acid phosphatase conferring increased phosphorous uptake. In certain embodiments, the nucleic acid sequence may be further defined as selected from the group consisting of: (a) a nucleic acid sequence encoding the polypeptide of SEQ ID NO:2; (b) a nucleic acid sequence comprising the sequence of SEQ ID NO:1; (c) a nucleic acid sequence hybridizing to SEQ ID NO:1 under conditions of 0.15 M NaCl and 70° C.; (d) a nucleic acid sequence comprising at least 85% sequence identity, including at least 90%, 95% and 98% identity, over the full length the nucleic acid sequence of SEQ ID NO:1; and (e) a nucleic acid sequence complementary to the nucleic acid sequence of polynucleotide sequence of (a), (b), (c) or (d).

In yet another aspect, the invention provides a recombinant vector comprising an isolated polynucleotide of the invention. The nucleic acid sequence may be in sense orientation. In certain embodiments, the recombinant vector may further comprise at least one additional sequence chosen from the group consisting of: a regulatory sequence, a selectable marker, a leader sequence and a terminator. In further embodiments, the additional sequence is a heterologous sequence and the promoter may be constitutive, developmentally-regulated, organelle-specific, inducible, inducible, tissue-specific, constitutive, cell-specific, seed specific, or germination-specific promoter. The recombinant vector may or may not be an isolated expression cassette.

In still yet another aspect, the invention provides an isolated polypeptide comprising the amino acid sequence of SEQ ID NO:2, or a fragment thereof having acid phosphatase activity, and including sequences with at least 85% sequence identity, including at least 90%, 95% and 98% identity, to this sequence.

In still yet another aspect, the invention provides a transgenic plant transformed with a selected DNA comprising a nucleic acid sequence of the invention encoding acid phosphatase activity and conferring increased phosphorous uptake. The transgenic plant may be a monocotyledonous or dicotyledonous plant and may be a legume. The plant may also be an $R_0$ transgenic plant and/or a progeny plant of any generation of an $R_0$ transgenic plant, wherein the transgenic plant has inherited the selected DNA from the $R_0$ transgenic plant.

In still yet another aspect, the invention provides a seed of a transgenic plant of the invention, wherein the seed comprises the selected DNA. The invention also provides a host cell transformed with such a selected DNA. The host cell may express a protein encoded by the selected DNA. The cell may have inherited the selected DNA from a progenitor of the cell and may have been transformed with the selected DNA. The cell may be a plant cell.

In still yet another aspect, the invention provides a method of increasing plant phosphorous utilization comprising introducing into the plant a nucleic acid encoding acid phosphatase. In a method of the invention, up-regulating acid phosphatase may be carried out by introducing a recombinant vector of the invention into a plant. The vector may be introduced by plant breeding and/or direct genetic transformation.

In still yet another aspect, the invention provides a method of making food for human or animal consumption comprising: (a) obtaining the plant of the invention; (b) growing the plant under plant growth conditions to produce plant tissue from the plant; and (c) preparing food for human or animal consumption from the plant tissue. In the method, preparing food may comprise harvesting plant tissue. In certain embodiments, the food is starch, protein, meal, flour or grain.

In still yet another aspect, the invention provides a method for bioremediation of phosphorous comprising: (a) identifying a soil and/or water sample in need of bioremediation for phosphorous; (b) obtaining a transgenic plant expressing a heterologous nucleic acid sequence encoding acid phosphatase, wherein the transgenic plant expresses the nucleic acid sequence and exhibits increased soil phosphorous uptake relative to a plant of the same genotype lacking the nucleic acid sequence; and (c) growing the roots of the plant in the presence of the soil/and or water to allow the plant to bioremediate the phosphorous.

BRIEF DESCRIPTION OF THE DRAWINGS

The following drawings form part of the present specification and are included to further demonstrate certain aspects of the invention. The invention may be better understood by reference to one or more of these drawings in combination with the detailed description of specific embodiments presented herein:

(FIG. 1A) Northern hybridization analysis of different organs of *M. truncatula* under low (10 µM) and high (2 mM) Pi conditions. The 3' UTR of MtPAP1 cDNA was used as probe. (FIG. 1B) Southern hybridization analysis of *M. truncatula* genomic DNA digested with different restriction enzymes. The 3' UTR of MtPAP1 cDNA was used as probe.

FIG. 3A-C. Subcellular localization of GFP in roots of transgenic *Arabidopsis*. (FIG. 3A) transgenic root carrying the gene construct CaMV35S::sp (native)-MtPAP1-GFP. (FIG. 3B) transgenic root carrying the gene construct CaMV35S::sp' (patatin)-MtPAP1-GFP. (FIG. 3C) transgenic root carrying the gene construct CaMV35S::GFP.

FIG. 4. Schematic illustration of chimeric MtPAP1 gene constructs used for generating transgenic *Arabidopsis* plants. MtPT1 promoter: root-specific promoter from phosphate transporter 1 of *M. truncatula*. sp: native signal peptide sequence form the *M. truncatula* purple acid phosphatase (MtPAP1). sp': patatin signal sequence from potato.

FIG. 5A-F. Transcript levels (FIG. 5A, FIG. 5C, FIG. 5E) and APase activities in root apoplast (FIG. 5B, FIG. 5D, FIG. 5F) of transgenic *Arabidopsis* growing in agar medium with phytate as the sole source of P. (FIG. 5A, FIG. 5B) Transgenic lines carrying the gene construct MtPT1::sp (native)-MtPAP1. (FIG. 5C, FIG. 5D) Transgenic lines carrying the gene construct MtPT1::sp' (patatin)-MtPAP1. (E, F) Transgenic lines carrying the gene construct CaMV35S::sp' (patatin)-MtPAP1. The APase activity (mmol P mg protein-1 h-1) data are presented as the mean±SE of three individual assays per line.

FIG. 6A-C. APase activities in whole root extracts of transgenic *Arabidopsis* lines growing in agar medium with phytate as the sole source of P. (FIG. 6A) Transgenic lines carrying the gene construct MtPT1::sp (native)-MtPAP1. (FIG. 6B) Transgenic lines carrying the gene construct MtPT1::sp' (patatin)-MtPAP1. (FIG. 6C) Transgenic lines carrying the gene construct CaMV35S::sp' (patatin)-MtPAP1. The APase activity (mmol P mg protein-1 h-1) data are presented as the mean±SE of three individual assays per line.

FIG. 7A-D. Staining of acid phosphatase activity in roots of *Arabidopsis* growing in agar medium with phytate as the sole source of P. (FIG. 7A) Empty vector control. (FIG. 7B) Transgenic line carrying the gene construct MtPT1::sp (native)-MtPAP1. (FIG. 7C) Transgenic line carrying the gene construct MtPT1::sp' (patatin)-MtPAP1. (FIG. 7D) Transgenic line carrying the gene construct CaMV35S::sp' (patatin)-MtPAP1. The dark, purple color indicates enzyme activity in roots and root exudates.

FIG. 8A-D. Transgenic *Arabidopsis* plants growing in MS agar medium with phytate as the sole source of P. The plants from different lines were firstly grown in normal MS agar medium for 8 days and then transferred to the MS-phytate medium for two weeks. (FIG. 8A) empty vector control. (FIG. 8B) Line 1'. (FIG. 8C) Line 5'. (FIG. 8D) Line 6'.

FIG. 9A-B. Intermediates of phytate degradation by root exudates of *Arabidopsis* plants in liquid culture medium with phytate as the sole source of P. (FIG. 9A) Empty vector control. (FIG. 9B) A transgenic line. Data are presented as the means±SE of three individual assays.

FIG. 10A-F. Fresh weight (FIG. 10A, FIG. 10C, FIG. 10E) and dry weight (FIG. 10B, FIG. 10D, FIG. 10F) of transgenic *Arabidopsis* lines growing in agar medium with phytate as the sole source of P. (FIG. 10A, FIG. 10B) Transgenic lines carrying the gene construct MtPT1::sp (native)-MtPAP1. (FIG. 10C, FIG. 10D) Transgenic lines carrying the gene construct MtPT1::sp' (patatin)-MtPAP1. (FIG. 10E, FIG. 10F) Transgenic lines carrying the gene construct CaMV35S::sp' (patatin)-MtPAP1. Data are presented as the mean±SE of six replicates per line.

FIG. 11A-C. Total P content of transgenic *Arabidopsis* lines growing in agar medium with phytate as the sole source of P. (FIG. 11A) Transgenic lines carrying the gene construct MtPT1::sp (native)-MtPAP1. (FIG. 11B) Transgenic lines carrying the gene construct MtPT1::sp' (patatin)-MtPAP1. (FIG. 11C) Transgenic lines carrying the gene construct CaMV35S::sp' (patatin)-MtPAP1. Data are presented as the mean±SE of six individual assays per line.

DETAILED DESCRIPTION OF THE INVENTION

Figure 1:
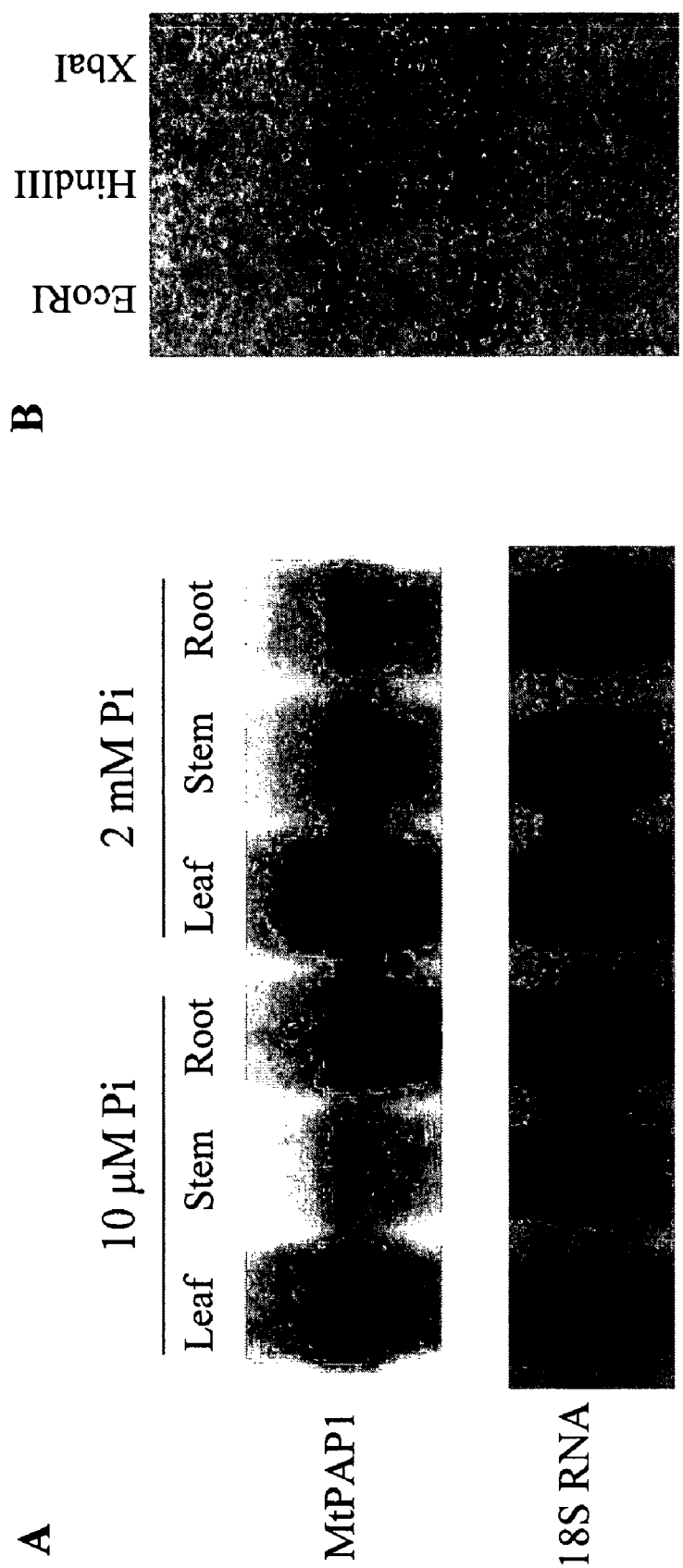
FIG. 1A-B.

The invention overcomes the limitations of the prior art by providing plant genes that, when expressed heterologously, result in increased plant phosphorous (P) uptake. The inventors demonstrate in one embodiment that overexpression of certain plant acid phosphatases (APases) that were identified can be used to enhance the acquisition of phosphate from P sources that are normally largely inaccessible to plants, thus expanding the opportunities for engineering and breeding plants with enhanced phosphate metabolism efficiency. Phosphorus is one of the least-available nutrients in soils, and therefore this represents a significant advance to agriculture and the environment in general. Increased P-utilization may be implemented both to increase crop yields in P-deficient environments and to minimize reliance on fertilizers, which can leach in rainwater runoff and represent a significant environmental problem.

In one example, the inventors have demonstrated the characterization and transgenic expression of a novel purple acid phosphatase gene that was designated MtPAP1 and originally isolated from *Medicago truncatula*. Overexpression of the gene in *Arabidopsis thaliana* was demonstrated to cause drastic increases in apoplast APase activity, biomass production and total phosphorous (P) content in transgenic plants when phytate was supplied as the sole source of P.

Three chimeric gene constructs were made including MtPAP1 either driven by a root-specific promoter or by a constitutive promoter. Constructs included a native signal sequence of MtPAP1 or a patatin signal sequence from potato. Transgenic *Arabidopsis* plants carrying the chimeric MtPAP1 gene constructs showed 4.6- to 9.9-fold higher acid phosphatase activities in the root apoplast relative to the control plants. The increase in enzyme activity correlated closely with the expression levels of the transgenes. The expressed acid phosphatase was secreted into the rhizosphere as shown by enzyme activity staining and HPLC analysis of organic P degradation in liquid culture. Transgenic lines showed a minimum of a twofold increase in biomass production and total phosphorus content when phytate was supplied as the sole source of phosphorus. The results clearly demonstrate overexpression of plant acid phosphatase genes as an effective approach to improve phosphorus acquisition.

The pattern of mRNA accumulation for the MtPAP1 sequence showed a novel expression pattern. Although the accumulation of the MtPAP1 transcript was inducible in *M. truncatula* roots under low-Pi conditions, high levels of transcript were accumulated in leaves under high-Pi conditions, indicating the occurrence of a transition of transcript accumulation from leaves to roots when the Pi level was decreased. Thus, the gene was indicated to involve utilizing endogenous P storage in leaves when Pi was sufficient, but its transcription activated in roots when Pi became limited. The results indicate the existence of a delicate regulation system controlling the expression of the MtPAP1 gene in response to Pi levels.

When MtPAP1 was overexpressed in transgenic *Arabidopsis* plants, APase activities in root apoplast were increased more than fourfold. The increase in enzyme activity was closely correlated with the expression levels of the transgenes. The accumulated APase was further secreted into the rhizosphere and resulted in at least a twofold increase in biomass production and total P contents in the transgenic plants when a major organic P, phytate, was supplied as the sole P source. The results clearly demonstrated that overexpression of plant APases gene(s) may be used to improve P acquisition, and thus plant growth and productivity in soils with limited free P or maintaining productivity while reducing the use of P fertilizers. Because the transgenic plants had higher P concentration and drastically increased total P contents, this approach is also applicable to removing excessive organic P from certain land areas. One example of such a place is land dumped with poultry litter. The runoff of excessive P in such areas has caused environmental concerns of polluting surface or groundwater (Gaston et al., 2003; Pote et al., 2003).

In certain aspects, a plant signal peptide sequence may be used to facilitate the extracellular secretion of active APases in accordance with the invention (Li et al., 1997; Richardson et al., 2001). The inventors, in one embodiment, compared the effectiveness of a native MtPAP1 signal sequence (sp) and the patatin signal sequence (sp') on secretion and activities of APase. The two gene constructs, MtPT1::sp-MtPAP1 and MtPT1::sp'-MtPAP1, differed only in the signal sequence used. Transgenic plants carrying either of the gene constructs showed high levels of APase activity in apoplast, consistent with the localization of MtPAP1-GFP fusion protein. Furthermore, in both cases, active APase was released to the rhizosphere as demonstrated by enzyme activity staining and HPLC analysis of phytate degradation in liquid culture. Although the average values of APase activity and biomass production were slightly lower in transgenic lines carrying the gene construct with native signal sequence, due to large variation in expression levels observed in individual transgenics, it could not be concluded that the patatin signal was more effective than the native signal sequence. Therefore, either signal sequence was shown effective for secretion of APases in transgenic studies and other sequences may be used as is known in the art.

It may be desired in particular embodiments to use a root-specific promoter for transgenic expression of APase genes, such as the MtPT1, MtPT2, or MtPT3 promoters (SEQ ID NOs: 22-24). The MtPT1 promoter and a constitutive promoter (CaMV35S) were tested in conjunction with APase. Because the promoter region was the only difference between the gene constructs MtPT1::sp'-MtPAP1 and CaMV35S::sp'-MtPAP1, plants transformed with these two transgenes were compared. The two sets of transgenic lines did not show significant difference in their APase activity, biomass production or total P content. No obvious negative effects were observed when MtPAP1 was driven by the constitutive CaMV35S promoter. This is probably because the APase was mainly accumulated in apoplast, or it may be related to the expression pattern of the gene and natural occurrence of the enzyme in leaves under high and low P conditions.

In summary, consistent and closely related molecular, biochemical, phenotypic and biomass data demonstrated for the first time that the transgenic expression of a plant purple acid phosphatase gene led to significant improvement in P uptake and plant growth when phytate was supplied as the sole P source. The results demonstrate a valuable approach for improving plant organic P utilization and for bioremediation.

I. Plant Transformatiom Constructs, Nucleic Acids and Polypeptides

Certain embodiments of the current invention concern plant transformation constructs comprising one or more acid phosphatase coding sequence. An exemplary coding sequence for use with the invention encodes the polypeptide of SEQ ID NO:2. In certain embodiments of the invention, transformation constructs comprise the nucleic acid sequence of SEQ ID NO:1 or derivatives thereof.

Coding sequences may be provided operably linked to a heterologous promoter, in either sense or antisense orientation. Expression constructs are also provided comprising these sequences, including antisense oligonucleotides thereof, as are plants and plant cells transformed with the sequences. The construction of vectors which may be employed in conjunction with plant transformation techniques using these or other sequences according to the invention will be known to those of skill of the art in light of the present disclosure (see, for example, Sambrook et al., 1989; Gelvin et al., 1990). The techniques of the current invention are thus not limited to any particular nucleic acid sequences.

Provided herein are also transformation vectors comprising nucleic acids capable of hybridizing to the nucleic acid sequences provided herein, for example, SEQ ID NO:1. As used herein, "hybridization," "hybridizes" or "capable of hybridizing" is understood to mean the forming of a double or triple stranded molecule or a molecule with partial double or triple stranded nature. Such hybridization may take place under relatively high stringency conditions, including low salt and/or high temperature conditions, such as provided by a wash in about 0.02 M to about 0.15 M NaCl at temperatures of about 50° C. to about 70° C. for 10 min. In one embodiment of the invention, the conditions are 0.15 M NaCl and 70° C. Stringent conditions tolerate little mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

The invention provides a polynucleotide sequence identical over its entire length to each coding sequence set forth in the Sequence Listing. The invention also provides the coding sequence for the mature polypeptide or a fragment thereof, as well as the coding sequence for the mature polypeptide or a fragment thereof in a reading frame with other coding sequences, such as those encoding a leader or secretory sequence, a pre-, pro-, or prepro-protein sequence. The polynucleotide can also include non-coding sequences, including for example, but not limited to, non-coding 5' and 3' sequences, such as the transcribed, untranslated sequences, termination signals, ribosome binding sites, sequences that stabilize mRNA, introns, polyadenylation signals, and additional coding sequence that encodes additional amino acids. For example, a marker sequence can be included to facilitate the purification of the fused polypeptide. Polynucleotides of the present invention also include polynucleotides comprising a structural gene and the naturally associated sequences that control gene expression.

Another aspect of the present invention relates to the polypeptide sequence set forth in the SEQ ID NO:2, as well as polypeptides and fragments thereof, particularly those polypeptides which exhibit acid phosphatase activity and also those polypeptides which have at least 85%, more preferably at least 90% identity, and most preferably at least 95% identity to a polypeptide sequence selected from the group of sequences set forth in the Sequence Listing, and also include portions of such polypeptides, wherein such portion of the polypeptide preferably includes at least 30 amino acids and more preferably includes at least 50 amino acids.

In still another aspect of the invention a nucleotide sequence encoding the polypeptide of any of SEQ ID NOs: 25-51 may be operable linked to a heterologous promoter. These sequences may be used to transform a plants and to increase the P utilization. Promoter sequences that may be used include but are not limited to constitutive promoters, inducible promoters, and tissue specific promoters. In certain aspects it is contemplated that a root specific promoter may be used to express nucleotide sequence encoding SEQ ID NOs: 25-51.

"Identity," as is well understood in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences. Methods to determine "identity" are designed to give the largest match between the sequences tested. Moreover, methods to determine identity are codified in publicly available programs. "Identity" can be readily calculated by known methods including, but not limited to, those described in Computational Molecular Biology, Lesk, A. M., ed., Oxford University Press, New York (1988); Biocomputing: Informatics and Genome Projects, Smith, D. W., ed., Academic Press, New York, 1993; Computer Analysis of Sequence Data, Part I, Griffin, A. M. and Griffin, H. G., eds., Humana Press, New Jersey (1994); Sequence Analysis in Molecular Biology, von Heinje, G., Academic Press (1987); Sequence Analysis Primer, Gribskov, M. and Devereux, J., eds., Stockton Press, New York (1991); and Carillo, H., and Lipman, D., SIAM J Applied Math, 48:1073 (1988). Computer programs can be used to determine "identity" between two sequences these programs include but are not limited to, GCG (Devereux, J., et al., Nucleic Acids Research 12(1):387 (1984); suite of five BLAST programs, three designed for nucleotide sequences queries (BLASTN, BLASTX, and TBLASTX) and two designed for protein sequence queries (BLASTP and TBLASTN) (Coulson, Trends in Biotechnology, 12: 76-80 (1994); Birren, et al., Genome Analysis, 1:

543-559 (1997)). The BLAST X program is publicly available from NCBI and other sources (BLAST Manual, Altschul, S., et al., NCBI NLM NIH, Bethesda, Md. 20894; Altschul, S., et al., J. Mol. Biol., 215:403-410 (1990)). The well known Smith Waterman algorithm can also be used to determine identity.

Parameters for polypeptide sequence comparison include the following: Algorithm: Needleman and Wunsch, *J. Mol. Biol*. 48:443-453 (1970); Comparison matrix: BLOSSUM62 from Hentikoff and Hentikoff, *Proc. Natl. Acad. Sci USA* 89:10915-10919 (1992); Gap Penalty: 12; and Gap Length Penalty: 4. A program which can be used with these parameters is publicly available as the "gap" program from Genetics Computer Group, Madison Wis. The above parameters along with no penalty for end gap may serve as default parameters for peptide comparisons.

Parameters for polynucleotide sequence comparison include the following: Algorithm: Needleman and Wunsch, *J. Mol. Biol*. 48:443-453 (1970); Comparison matrix: matches=+10; mismatches=0; Gap Penalty: 50; and Gap Length Penalty: 3. A program which can be used with these parameters is publicly available as the "gap" program from Genetics Computer Group, Madison Wis. The above parameters may serve as the default parameters for nucleic acid comparisons.

One beneficial use of the sequences provided by the invention will be in the alteration of plant phenotypes by genetic transformation with acid phosphatase coding sequences. The acid phosphatase coding sequence may be provided with other sequences. Where an expressible coding region that is not necessarily a marker coding region is employed in combination with a marker coding region, one may employ the separate coding regions on either the same or different DNA segments for transformation. In the latter case, the different vectors are delivered concurrently to recipient cells to maximize cotransformation.

The choice of any additional elements used in conjunction with an acid phosphatase coding sequences will often depend on the purpose of the transformation. One of the major purposes of transformation of crop plants is to add commercially desirable, agronomically important traits to the plant, as described above.

Vectors used for plant transformation may include, for example, plasmids, cosmids, YACs (yeast artificial chromosomes), BACs (bacterial artificial chromosomes) or any other suitable cloning system, as well as fragments of DNA therefrom. Thus when the term "vector" or "expression vector" is used, all of the foregoing types of vectors, as well as nucleic acid sequences isolated therefrom, are included. It is contemplated that utilization of cloning systems with large insert capacities will allow introduction of large DNA sequences comprising more than one selected gene. In accordance with the invention, this could be used to introduce genes corresponding to an entire biosynthetic pathway into a plant.

Particularly useful for transformation are expression cassettes which have been isolated from such vectors. DNA segments used for transforming plant cells will, of course, generally comprise the cDNA, gene or genes which one desires to introduce into and have expressed in the host cells. These DNA segments can further include structures such as promoters, enhancers, polylinkers, or even regulatory genes as desired. The DNA segment or gene chosen for cellular introduction will often encode a protein which will be expressed in the resultant recombinant cells resulting in a screenable or selectable trait and/or which will impart an improved phenotype to the resulting transgenic plant. Preferred components likely to be included with vectors used in the current invention are as follows.

A. Regulatory Elements

Exemplary promoters for expression of a nucleic acid sequence include plant promoters such as the CaMV 35S promoter (Odell et al., 1985), or others such as CaMV 19S (Lawton et al., 1987), nos (Ebert et al., 1987), Adh (Walker et al., 1987), sucrose synthase (Yang and Russell, 1990), a-tubulin, actin (Wang et al., 1992), cab (Sullivan et al., 1989), PEPCase (Hudspeth and Grula, 1989) or those promoters associated with the R gene complex (Chandler et al., 1989). Tissue specific promoters such as root cell promoters (Conkling et al., 1990) and tissue specific enhancers (Fromm et al., 1986) are also contemplated to be useful, as are inducible promoters such as ABA- and turgor-inducible promoters. In one embodiment of the invention, the native promoter of an acid phosphatase coding sequence is used.

The DNA sequence between the transcription initiation site and the start of the coding sequence, i.e., the untranslated leader sequence, can also influence gene expression. One may thus wish to employ a particular leader sequence with a transformation construct of the invention. Preferred leader sequences are contemplated to include those which comprise sequences predicted to direct optimum expression of the attached gene, i.e., to include a preferred consensus leader sequence which may increase or maintain mRNA stability and prevent inappropriate initiation of translation. The choice of such sequences will be known to those of skill in the art in light of the present disclosure. Sequences that are derived from genes that are highly expressed in plants will typically be preferred.

It is envisioned that acid phosphatase coding sequences may be introduced under the control of novel promoters or enhancers, etc., or homologous or tissue specific promoters or control elements. For instance the root specific MtPT1, MtPT2, or MtPT3 promoters may be used (SEQ ID NOs:22-24). Vectors for use in tissue-specific targeting of genes in transgenic plants will typically include tissue-specific promoters and may also include other tissue-specific control elements such as enhancer sequences. Promoters which direct specific or enhanced expression in certain plant tissues will be known to those of skill in the art in light of the present disclosure. These include, for example, the rbcS promoter, specific for green tissue; the ocs, nos and mas promoters which have higher activity in roots.

B. Terminators

Transformation constructs prepared in accordance with the invention will typically include a 3' end DNA sequence that acts as a signal to terminate transcription and allow for the poly-adenylation of the mRNA produced by coding sequences operably linked to a promoter. In one embodiment of the invention, the native terminator of an acid phosphatase coding sequence is used. Alternatively, a heterologous 3' end may enhance the expression of sense or antisense acid phosphatase coding sequences. Examples of terminators that are deemed to be useful in this context include those from the nopaline synthase gene of *Agrobacterium tumefaciens* (nos 3' end) (Bevan et al., 1983), the terminator for the T7 transcript from the octopine synthase gene of *Agrobacterium tumefaciens*, and the 3' end of the protease inhibitor I or II genes from potato or tomato. Regulatory elements such as an Adh intron (Callis et al., 1987), sucrose synthase intron (Vasil et al., 1989) or TMV omega element (Gallie et al., 1989), may further be included where desired.

C. Transit or Signal Peptides

Sequences that are joined to the coding sequence of an expressed gene, which are removed post-translationally from the initial translation product and which facilitate the transport of the protein into or through intracellular or extracellular membranes, are termed transit (usually into vacuoles, vesicles, plastids and other intracellular organelles) and signal sequences (usually to the endoplasmic reticulum, golgi apparatus and outside of the cellular membrane). By facilitating the transport of the protein into compartments inside and outside the cell, these sequences may increase the accumulation of gene product protecting them from proteolytic degradation. These sequences also allow for additional mRNA sequences from highly expressed genes to be attached to the coding sequence of the genes. Since mRNA being translated by ribosomes is more stable than naked mRNA, the presence of translatable mRNA in front of the gene may increase the overall stability of the mRNA transcript from the gene and thereby increase synthesis of the gene product. Since transit and signal sequences are usually post-translationally removed from the initial translation product, the use of these sequences allows for the addition of extra translated sequences that may not appear on the final polypeptide. It further is contemplated that targeting of certain proteins may be desirable in order to enhance the stability of the protein (U.S. Pat. No. 5,545,818, incorporated herein by reference in its entirety).

Additionally, vectors may be constructed and employed in the intracellular targeting of a specific gene product within the cells of a transgenic plant or in directing a protein to the extracellular environment. This generally will be achieved by joining a DNA sequence encoding a transit or signal peptide sequence to the coding sequence of a particular gene. The resultant transit, or signal, peptide will transport the protein to a particular intracellular, or extracellular destination, respectively, and will then be post-translationally removed.

D. Marker Genes

By employing a selectable or screenable marker protein, one can provide or enhance the ability to identify transformants. "Marker genes" are genes that impart a distinct phenotype to cells expressing the marker protein and thus allow such transformed cells to be distinguished from cells that do not have the marker. Such genes may encode either a selectable or screenable marker, depending on whether the marker confers a trait which one can "select" for by chemical means, i.e., through the use of a selective agent (e.g., a herbicide, antibiotic, or the like), or whether it is simply a trait that one can identify through observation or testing, i.e., by "screening" (e.g., the green fluorescent protein). Of course, many examples of suitable marker proteins are known to the art and can be employed in the practice of the invention.

Included within the terms selectable or screenable markers also are genes which encode a "secretable marker" whose secretion can be detected as a means of identifying or selecting for transformed cells. Examples include markers which are secretable antigens that can be identified by antibody interaction, or even secretable enzymes which can be detected by their catalytic activity. Secretable proteins fall into a number of classes, including small, diffusible proteins detectable, e.g., by ELISA; small active enzymes detectable in extracellular solution (e.g., α-amylase, β-lactamase, phosphinothricin acetyltransferase); and proteins that are inserted or trapped in the cell wall (e.g., proteins that include a leader sequence such as that found in the expression unit of extensin or tobacco PR-S).

Many selectable marker coding regions are known and could be used with the present invention including, but not limited to, neo (Potrykus et al., 1985), which provides kanamycin resistance and can be selected for using kanamycin, G418, paromomycin, etc.; bar, which confers bialaphos or phosphinothricin resistance; a mutant EPSP synthase protein (Hinchee et al., 1988) conferring glyphosate resistance; a nitrilase such as bxn from *Klebsiella ozaenae* which confers resistance to bromoxynil (Stalker et al., 1988); a mutant acetolactate synthase (ALS) which confers resistance to imidazolinone, sulfonylurea or other ALS inhibiting chemicals (European Patent Application 154, 204, 1985); a methotrexate resistant DHFR (Thillet et al., 1988), a dalapon dehalogenase that confers resistance to the herbicide dalapon; or a mutated anthranilate synthase that confers resistance to 5-methyl tryptophan.

An illustrative embodiment of selectable marker capable of being used in systems to select transformants are those that encode the enzyme phosphinothricin acetyltransferase, such as the bar gene from *Streptomyces hygroscopicus* or the pat gene from *Streptomyces viridochromogenes*. The enzyme phosphinothricin acetyl transferase (PAT) inactivates the active ingredient in the herbicide bialaphos, phosphinothricin (PPT). PPT inhibits glutamine synthetase, (Murakami et al., 1986; Twell et al., 1989) causing rapid accumulation of ammonia and cell death.

Screenable markers that may be employed include a β-glucuronidase (GUS) or uidA gene which encodes an enzyme for which various chromogenic substrates are known; an R-locus gene, which encodes a product that regulates the production of anthocyanin pigments (red color) in plant tissues (Dellaporta et al., 1988); a β-lactamase gene (Sutcliffe, 1978), which encodes an enzyme for which various chromogenic substrates are known (e.g., PADAC, a chromogenic cephalosporin); a xylE gene (Zukowsky et al., 1983) which encodes a catechol dioxygenase that can convert chromogenic catechols; an α-amylase gene (Ikuta et al., 1990); a tyrosinase gene (Katz et al., 1983) which encodes an enzyme capable of oxidizing tyrosine to DOPA and dopaquinone which in turn condenses to form the easily-detectable compound melanin; a β-galactosidase gene, which encodes an enzyme for which there are chromogenic substrates; a luciferase (lux) gene (Ow et al., 1986), which allows for bioluminescence detection; an aequorin gene (Prasher et al., 1985) which may be employed in calcium-sensitive bioluminescence detection; or a gene encoding for green fluorescent protein (Sheen et al., 1995; Haseloff et al., 1997; Reichel et al., 1996; Tian et al., 1997; WO 97/41228).

Another screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It also is envisioned that this system may be developed for populational screening for bioluminescence, such as on tissue culture plates, or even for whole plant screening. The gene which encodes green fluorescent protein (GFP) is also contemplated as a particularly useful reporter gene (Sheen et al., 1995; Haseloff et al., 1997; Reichel et al., 1996; Tian et al., 1997; WO 97/41228). Expression of green fluorescent protein may be visualized in a cell or plant as fluorescence following illumination by particular wavelengths of light.

II. Genetic Transformation

Suitable methods for transformation of plant or other cells for use with the current invention are believed to include virtually any method by which DNA can be introduced into a cell, such as by direct delivery of DNA such as by PEG-mediated transformation of protoplasts (Omirulleh et al., 1993), by desiccation/inhibition-mediated DNA uptake (Potrykus et al., 1985), by electroporation (U.S. Pat. No. 5,384, 253, specifically incorporated herein by reference in its entirety), by agitation with silicon carbide fibers (Kaeppler et al., 1990; U.S. Pat. No. 5,302,523, specifically incorporated herein by reference in its entirety; and U.S. Pat. No. 5,464,765, specifically incorporated herein by reference in its entirety), by Agrobacterium-mediated transformation (U.S. Pat. No. 5,591,616 and U.S. Pat. No. 5,563,055; both specifically incorporated herein by reference) and by acceleration of DNA coated particles (U.S. Pat. No. 5,550,318; U.S. Pat. No. 5,538,877; and U.S. Pat. No. 5,538,880; each specifically incorporated herein by reference in its entirety), etc. Through the application of techniques such as these, the cells of virtually any plant species may be stably transformed, and these cells developed into transgenic plants.

Agrobacterium-mediated transfer is a widely applicable system for introducing genes into plant cells because the DNA can be introduced into whole plant tissues, thereby bypassing the need for regeneration of an intact plant from a protoplast. The use of Agrobacterium-mediated plant integrating vectors to introduce DNA into plant cells is well known in the art. See, for example, the methods described by Fraley et al., (1985), Rogers et al., (1987) and U.S. Pat. No. 5,563,055, specifically incorporated herein by reference in its entirety.

Agrobacterium-mediated transformation is most efficient in dicotyledonous plants and is the preferable method for transformation of dicots, including Arabidopsis, tobacco, tomato, alfalfa and potato. Indeed, while Agrobacterium-mediated transformation has been routinely used with dicotyledonous plants for a number of years, it has only recently become applicable to monocotyledonous plants. Advances in Agrobacterium-mediated transformation techniques have now made the technique applicable to nearly all monocotyledonous plants. For example, Agrobacterium-mediated transformation techniques have now been applied to rice (Hiei et al., 1997; U.S. Pat. No. 5,591,616, specifically incorporated herein by reference in its entirety), wheat (McCormac et al., 1998), barley (Tingay et al., 1997; McCormac et al., 1998), alfalfa (Thomas et al., 1990) and maize (Ishidia et al., 1996).

Modern Agrobacterium transformation vectors are capable of replication in E. coli as well as Agrobacterium, allowing for convenient manipulations as described (Klee et al., 1985). Moreover, recent technological advances in vectors for Agrobacterium-mediated gene transfer have improved the arrangement of genes and restriction sites in the vectors to facilitate the construction of vectors capable of expressing various polypeptide coding genes. The vectors described (Rogers et al., 1987) have convenient multi-linker regions flanked by a promoter and a polyadenylation site for direct expression of inserted polypeptide coding genes and are suitable for present purposes. In addition, Agrobacterium containing both armed and disarmed Ti genes can be used for the transformations. In those plant strains where Agrobacterium-mediated transformation is efficient, it is the method of choice because of the facile and defined nature of the gene transfer.

One also may employ protoplasts for electroporation transformation of plants (Bates, 1994; Lazzeri, 1995). For example, the generation of transgenic soybean plants by electroporation of cotyledon-derived protoplasts is described by Dhir and Widholm in Intl. Patent Appl. Publ. No. WO 9217598 (specifically incorporated herein by reference). Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

Another method for delivering transforming DNA segments to plant cells in accordance with the invention is microprojectile bombardment (U.S. Pat. No. 5,550,318; U.S. Pat. No. 5,538,880; U.S. Pat. No. 5,610,042; and PCT Application WO 94/09699; each of which is specifically incorporated herein by reference in its entirety). In this method, particles may be coated with nucleic acids and delivered into cells by a propelling force. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. Hence, it is proposed that DNA-coated particles may increase the level of DNA delivery via particle bombardment but are not, in and of themselves, necessary.

An illustrative embodiment of a method for delivering DNA into plant cells by acceleration is the Biolistics Particle Delivery System, which can be used to propel particles coated with DNA or cells through a screen, such as a stainless steel or Nytex screen, onto a filter surface covered with monocot plant cells cultured in suspension. The screen disperses the particles so that they are not delivered to the recipient cells in large aggregates. Microprojectile bombardment techniques are widely applicable, and may be used to transform virtually any plant species. Examples of species for which have been transformed by microprojectile bombardment include monocot species such as maize (PCT Application WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (VanEck et al. 1995), and legumes in general (U.S. Pat. No. 5,563,055, specifically incorporated herein by reference in its entirety).

Application of these systems to different plant strains depends upon the ability to regenerate that particular plant strain from protoplasts. Illustrative methods for the regeneration of cereals from protoplasts have been described (Toriyama et al., 1986; Yamada et al., 1986; Abdullah et al., 1986; Omirulleh et al., 1993 and U.S. Pat. No. 5,508,184; each specifically incorporated herein by reference in its entirety). Examples of the use of direct uptake transformation of cereal protoplasts include transformation of rice (Ghosh-Biswas et al., 1994), sorghum (Battraw and Hall, 1991), barley (Lazerri, 1995), oat (Zheng and Edwards, 1990) and maize (Omirulleh et al., 1993).

To transform plant strains that cannot be successfully regenerated from protoplasts, other ways to introduce DNA into intact cells or tissues can be utilized. For example, regeneration of cereals from immature embryos or explants can be effected as described (Vasil, 1989). Also, silicon carbide fiber-mediated transformation may be used with or without protoplasting (Kaeppler, 1990; Kaeppler et al., 1992; U.S. Pat. No. 5,563,055, specifically incorporated herein by reference in its entirety). Transformation with this technique is accomplished by agitating silicon carbide fibers together with cells in a DNA solution. DNA passively enters as the cells are punctured. This technique has been used successfully with, for example, the monocot cereals maize (PCT Application WO 95/06128, specifically incorporated herein by reference in its entirety; (Thompson, 1995) and rice (Nagatani, 1997).

Tissue cultures may be used in certain transformation techniques for the preparation of cells for transformation and for the regeneration of plants therefrom. Maintenance of tissue cultures requires use of media and controlled environments. "Media" refers to the numerous nutrient mixtures that are used to grow cells in vitro, that is, outside of the intact living organism. The medium usually is a suspension of various categories of ingredients (salts, amino acids, growth regulators, sugars, buffers) that are required for growth of most cell types. However, each specific cell type requires a specific range of ingredient proportions for growth, and an even more specific range of formulas for optimum growth. Rate of cell growth also will vary among cultures initiated with the array of media that permit growth of that cell type.

Tissue that can be grown in a culture includes meristem cells, Type I, Type II, and Type III callus, immature embryos and gametic cells such as microspores, pollen, sperm and egg cells. Type I, Type II, and Type III callus may be initiated from tissue sources including, but not limited to, immature embryos, seedling apical meristems, root, leaf, microspores and the like. Those cells which are capable of proliferating as callus also are recipient cells for genetic transformation.

Somatic cells are of various types. Embryogenic cells are one example of somatic cells which may be induced to regenerate a plant through embryo formation. Non-embryogenic cells are those which typically will not respond in such a fashion. Certain techniques may be used that enrich recipient cells within a cell population. For example, Type II callus development, followed by manual selection and culture of friable, embryogenic tissue, generally results in an enrichment of cells. Manual selection techniques which can be employed to select target cells may include, e.g., assessing cell morphology and differentiation, or may use various physical or biological means. Cryopreservation also is a possible method of selecting for recipient cells.

Where employed, cultured cells may be grown either on solid supports or in the form of liquid suspensions. In either instance, nutrients may be provided to the cells in the form of media, and environmental conditions controlled. There are many types of tissue culture media comprised of various amino acids, salts, sugars, growth regulators and vitamins. Most of the media employed in the practice of the invention will have some similar components, but may differ in the composition and proportions of their ingredients depending on the particular application envisioned. For example, various cell types usually grow in more than one type of media, but will exhibit different growth rates and different morphologies, depending on the growth media. In some media, cells survive but do not divide. Various types of media suitable for culture of plant cells previously have been described. Examples of these media include, but are not limited to, the N6 medium described by Chu et al. (1975) and MS media (Murashige and Skoog, 1962).

III. Production and Characterization of Stably Transformed Plants

After effecting delivery of exogenous DNA to recipient cells, the next steps generally concern identifying the transformed cells for further culturing and plant regeneration. In order to improve the ability to identify transformants, one may desire to employ a selectable or screenable marker gene with a transformation vector prepared in accordance with the invention. In this case, one would then generally assay the potentially transformed cell population by exposing the cells to a selective agent or agents, or one would screen the cells for the desired marker gene trait.

A. Selection

It is believed that DNA is introduced into only a small percentage of target cells in any one study. In order to provide an efficient system for identification of those cells receiving DNA and integrating it into their genomes one may employ a means for selecting those cells that are stably transformed. One exemplary embodiment of such a method is to introduce into the host cell, a marker gene which confers resistance to some normally inhibitory agent, such as an antibiotic or herbicide. Examples of antibiotics which may be used include the aminoglycoside antibiotics neomycin, kanamycin and paromomycin, or the antibiotic hygromycin. Resistance to the aminoglycoside antibiotics is conferred by aminoglycoside phosphostransferase enzymes such as neomycin phosphotransferase II (NPT II) or NPT I, whereas resistance to hygromycin is conferred by hygromycin phosphotransferase.

Potentially transformed cells then are exposed to the selective agent. In the population of surviving cells will be those cells where, generally, the resistance-conferring gene has been integrated and expressed at sufficient levels to permit cell survival. Cells may be tested further to confirm stable integration of the exogenous DNA.

One herbicide which constitutes a desirable selection agent is the broad spectrum herbicide bialaphos. Bialaphos is a tripeptide antibiotic produced by *Streptomyces hygroscopicus* and is composed of phosphinothricin (PPT), an analogue of L-glutamic acid, and two L-alanine residues. Upon removal of the L-alanine residues by intracellular peptidases, the PPT is released and is a potent inhibitor of glutamine synthetase (GS), a pivotal enzyme involved in ammonia assimilation and nitrogen metabolism (Ogawa et al., 1973). Synthetic PPT, the active ingredient in the herbicide Liberty™ also is effective as a selection agent. Inhibition of GS in plants by PPT causes the rapid accumulation of ammonia and death of the plant cells.

The organism producing bialaphos and other species of the genus *Streptomyces* also synthesizes an enzyme phosphinothricin acetyl transferase (PAT) which is encoded by the bar gene in *Streptomyces hygroscopicus* and the pat gene in *Streptomyces* viridochromogenes. The use of the herbicide resistance gene encoding phosphinothricin acetyl transferase (PAT) is referred to in DE 3642 829 A, wherein the gene is isolated from *Streptomyces* viridochromogenes. In the bacterial source organism, this enzyme acetylates the free amino group of PPT preventing auto-toxicity (Thompson et al., 1987). The bar gene has been cloned (Murakami et al., 1986; Thompson et al., 1987) and expressed in transgenic tobacco, tomato, potato (De Block et al, 1987) *Brassica* (De Block et al., 1989) and maize (U.S. Pat. No. 5,550,318). In previous reports, some transgenic plants which expressed the resistance gene were completely resistant to commercial formulations of PPT and bialaphos in greenhouses.

Another example of a herbicide which is useful for selection of transformed cell lines in the practice of the invention is the broad spectrum herbicide glyphosate. Glyphosate inhibits the action of the enzyme EPSPS which is active in the aromatic amino acid biosynthetic pathway. Inhibition of this enzyme leads to starvation for the amino acids phenylalanine, tyrosine, and tryptophan and secondary metabolites derived thereof. U.S. Pat. No. 4,535,060 describes the isolation of EPSPS mutations which confer glyphosate resistance on the *Salmonella typhimurium* gene for EPSPS, aroA. The EPSPS gene was cloned from *Zea mays* and mutations similar to those found in a glyphosate resistant aroA gene were introduced in vitro. Mutant genes encoding glyphosate resistant EPSPS enzymes are described in, for example, International Patent WO 97/4103. The best characterized mutant EPSPS gene conferring glyphosate resistance comprises amino acid changes at residues 102 and 106, although it is anticipated that other mutations will also be useful (PCT/WO97/4103).

To use the bar-bialaphos or the EPSPS-glyphosate selective system, transformed tissue is cultured for 0-28 days on nonselective medium and subsequently transferred to medium containing from 1-3 mg/l bialaphos or 1-3 mM glyphosate as appropriate. While ranges of 1-3 mg/l bialaphos or 1-3 mM glyphosate will typically be preferred, it is proposed that ranges of 0.1-50 mg/l bialaphos or 0.1-50 mM glyphosate will find utility.

An example of a screenable marker trait is the enzyme luciferase. In the presence of the substrate luciferin, cells expressing luciferase emit light which can be detected on photographic or x-ray film, in a luminometer (or liquid scintillation counter), by devices that enhance night vision, or by a highly light sensitive video camera, such as a photon counting camera. These assays are nondestructive and transformed cells may be cultured further following identification. The photon counting camera is especially valuable as it allows one to identify specific cells or groups of cells which are expressing luciferase and manipulate those in real time. Another screenable marker which may be used in a similar fashion is the gene coding for green fluorescent protein.

It further is contemplated that combinations of screenable and selectable markers will be useful for identification of transformed cells. In some cell or tissue types a selection agent, such as bialaphos or glyphosate, may either not provide enough killing activity to clearly recognize transformed cells or may cause substantial nonselective inhibition of transformants and nontransformants alike, thus causing the selection technique to not be effective. It is proposed that selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. It is proposed that combinations of selection and screening may enable one to identify transformants in a wider variety of cell and tissue types. This may be efficiently achieved using a gene fusion between a selectable marker gene and a screenable marker gene, for example, between an NPTII gene and a GFP gene.

B. Regeneration and Seed Production

Cells that survive the exposure to the selective agent, or cells that have been scored positive in a screening assay, may be cultured in media that supports regeneration of plants. In an exemplary embodiment, MS and N6 media may be modified by including further substances such as growth regulators. One such growth regulator is dicamba or 2,4-D. However, other growth regulators may be employed, including NAA, NAA+2,4-D or picloram. Media improvement in these and like ways has been found to facilitate the growth of cells at specific developmental stages. Tissue may be maintained on a basic media with growth regulators until sufficient tissue is available to begin plant regeneration efforts, or following repeated rounds of manual selection, until the morphology of the tissue is suitable for regeneration, at least 2 wk, then transferred to media conducive to maturation of embryoids. Cultures are transferred every 2 wk on this medium. Shoot development will signal the time to transfer to medium lacking growth regulators.

The transformed cells, identified by selection or screening and cultured in an appropriate medium that supports regeneration, will then be allowed to mature into plants. Developing plantlets are transferred to soilless plant growth mix, and hardened, e.g., in an environmentally controlled chamber, for example, at about 85% relative humidity, 600 ppm $CO_2$, and 25-250 microeinsteins $m^{-2}$ $s^{-1}$ of light. Plants may be matured in a growth chamber or greenhouse. Plants can be regenerated from about 6 wk to 10 months after a transformant is identified, depending on the initial tissue. During regeneration, cells are grown on solid media in tissue culture vessels. Illustrative embodiments of such vessels are petri dishes and Plant Cons. Regenerating plants can be grown at about 19 to 28° C. After the regenerating plants have reached the stage of shoot and root development, they may be transferred to a greenhouse for further growth and testing.

Seeds on transformed plants may occasionally require embryo rescue due to cessation of seed development and premature senescence of plants. To rescue developing embryos, they are excised from surface-disinfected seeds 10-20 days post-pollination and cultured. An embodiment of media used for culture at this stage comprises MS salts, 2% sucrose, and 5.5 g/l agarose. In embryo rescue, large embryos (defined as greater than 3 mm in length) are germinated directly on an appropriate media. Embryos smaller than that may be cultured for 1 wk on media containing the above ingredients along with $10^{-5}$M abscisic acid and then transferred to growth regulator-free medium for germination.

C. Characterization

To confirm the presence of the exogenous DNA or "transgene(s)" in the regenerating plants, a variety of assays may be performed. Such assays include, for example, "molecular biological" assays, such as Southern and Northern blotting and PCR™; "biochemical" assays, such as detecting the presence of a protein product, e.g., by immunological means (ELISAs and Western blots) or by enzymatic function; plant part assays, such as leaf or root assays; and also, by analyzing the phenotype of the whole regenerated plant.

D. DNA Integration, RNA Expression and Inheritance

Genomic DNA may be isolated from cell lines or any plant parts to determine the presence of the exogenous gene through the use of techniques well known to those skilled in the art. Note, that intact sequences will not always be present, presumably due to rearrangement or deletion of sequences in the cell. The presence of DNA elements introduced through the methods of this invention may be determined, for example, by polymerase chain reaction (PCR™). Using this technique, discreet fragments of DNA are amplified and detected by gel electrophoresis. This type of analysis permits one to determine whether a gene is present in a stable transformant, but does not prove integration of the introduced gene into the host cell genome. It is typically the case, however, that DNA has been integrated into the genome of all transformants that demonstrate the presence of the gene through PCR™ analysis. In addition, it is not typically possible using PCR™ techniques to determine whether transformants have exogenous genes introduced into different sites in the genome, i.e., whether transformants are of independent origin. It is contemplated that using PCR™ techniques it would be possible to clone fragments of the host genomic DNA adjacent to an introduced gene.

Positive proof of DNA integration into the host genome and the independent identities of transformants may be determined using the technique of Southern hybridization. Using this technique specific DNA sequences that were introduced into the host genome and flanking host DNA sequences can be identified. Hence the Southern hybridization pattern of a given transformant serves as an identifying characteristic of that transformant. In addition it is possible through Southern hybridization to demonstrate the presence of introduced genes in high molecular weight DNA, i.e., confirm that the introduced gene has been integrated into the host cell genome. The technique of Southern hybridization provides information that is obtained using PCR™, e.g., the presence of a gene, but also demonstrates integration into the genome and characterizes each individual transformant.

It is contemplated that using the techniques of dot or slot blot hybridization which are modifications of Southern hybridization techniques one could obtain the same information that is derived from PCR™, e.g., the presence of a gene.

Both PCR™ and Southern hybridization techniques can be used to demonstrate transmission of a transgene to progeny. In most instances the characteristic Southern hybridization pattern for a given transformant will segregate in progeny as one or more Mendelian genes (Spencer et al., 1992) indicating stable inheritance of the transgene.

Whereas DNA analysis techniques may be conducted using DNA isolated from any part of a plant, RNA will only be expressed in particular cells or tissue types and hence it will be necessary to prepare RNA for analysis from these tissues. PCR™ techniques also may be used for detection and quantitation of RNA produced from introduced genes. In this application of PCR™ it is first necessary to reverse transcribe RNA into DNA, using enzymes such as reverse transcriptase, and then through the use of conventional PCR™ techniques amplify the DNA. In most instances PCR™ techniques, while useful, will not demonstrate integrity of the RNA product. Further information about the nature of the RNA product may be obtained by Northern blotting. This technique will demonstrate the presence of an RNA species and give information about the integrity of that RNA. The presence or absence of an RNA species also can be determined using dot or slot blot Northern hybridizations. These techniques are modifications of Northern blotting and will only demonstrate the presence or absence of an RNA species.

E. Gene Expression

While Southern blotting and PCR™ may be used to detect the gene(s) in question, they do not provide information as to whether the corresponding protein is being expressed. Expression may be evaluated by specifically identifying the protein products of the introduced genes or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange or gel exclusion chromatography. The unique structures of individual proteins offer opportunities for use of specific antibodies to detect their presence in formats such as an ELISA assay. Combinations of approaches may be employed with even greater specificity such as western blotting in which antibodies are used to locate individual gene products that have been separated by electrophoretic techniques. Additional techniques may be employed to absolutely confirm the identity of the product of interest such as evaluation by amino acid sequencing following purification. Although these are among the most commonly employed, other procedures may be additionally used.

Assay procedures also may be used to identify the expression of proteins by their functionality, especially the ability of enzymes to catalyze specific chemical reactions involving specific substrates and products. These reactions may be followed by providing and quantifying the loss of substrates or the generation of products of the reactions by physical or chemical procedures. Examples are as varied as the enzyme to be analyzed and may include assays for PAT enzymatic activity by following production of radiolabeled acetylated phosphinothricin from phosphinothricin and $^{14}$C-acetyl CoA or for anthranilate synthase activity by following loss of fluorescence of anthranilate, to name two.

Very frequently the expression of a gene product is determined by evaluating the phenotypic results of its expression. These assays also may take many forms including but not limited to analyzing changes in the chemical composition, morphology, or physiological properties of the plant. Chemical composition may be altered by expression of genes encoding enzymes or storage proteins which change amino acid composition and may be detected by amino acid analysis, or by enzymes which change starch quantity which may be analyzed by near infrared reflectance spectrometry. Morphological changes may include greater stature or thicker stalks. Most often changes in response of plants or plant parts to imposed treatments are evaluated under carefully controlled conditions termed bioassays.

IV. Breeding Plants of the Invention

In addition to direct transformation of a particular plant genotype with a construct prepared according to the current invention, transgenic plants may be made by crossing a plant having a selected DNA of the invention to a second plant lacking the construct. For example, a selected acid phosphatase coding sequence can be introduced into a particular plant variety by crossing, without the need for ever directly transforming a plant of that given variety. Therefore, the current invention not only encompasses a plant directly transformed or regenerated from cells which have been transformed in accordance with the current invention, but also the progeny of such plants. As used herein the term "progeny" denotes the offspring of any generation of a parent plant prepared in accordance with the instant invention, wherein the progeny comprises a selected DNA construct prepared in accordance with the invention. "Crossing" a plant to provide a plant line having one or more added transgenes relative to a starting plant line, as disclosed herein, is defined as the techniques that result in a transgene of the invention being introduced into a plant line by crossing a starting line with a donor plant line that comprises a transgene of the invention. To achieve this one could, for example, perform the following steps:

(a) plant seeds of the first (starting line) and second (donor plant line that comprises a transgene of the invention) parent plants;

(b) grow the seeds of the first and second parent plants into plants that bear flowers;

(c) pollinate a flower from the first parent plant with pollen from the second parent plant; and (d) harvest seeds produced on the parent plant bearing the fertilized flower.

Backcrossing is herein defined as the process including the steps of:

(a) crossing a plant of a first genotype containing a desired gene, DNA sequence or element to a plant of a second genotype lacking the desired gene, DNA sequence or element;

(b) selecting one or more progeny plant containing the desired gene, DNA sequence or element;

(c) crossing the progeny plant to a plant of the second genotype; and (d) repeating steps (b) and (c) for the purpose of transferring a desired DNA sequence from a plant of a first genotype to a plant of a second genotype.

Introgression of a DNA element into a plant genotype is defined as the result of the process of backcross conversion. A plant genotype into which a DNA sequence has been introgressed may be referred to as a backcross converted genotype, line, inbred, or hybrid. Similarly a plant genotype lacking the desired DNA sequence may be referred to as an unconverted genotype, line, inbred, or hybrid.

V. Definitions

Expression: The combination of intracellular processes, including transcription and translation undergone by a coding DNA molecule such as a structural gene to produce a polypeptide.

Genetic Transformation: A process of introducing a DNA sequence or construct (e.g., a vector or expression cassette) into a cell or protoplast in which that exogenous DNA is incorporated into a chromosome or is capable of autonomous replication.

Heterologous: A sequence which is not normally present in a given host genome in the genetic context in which the sequence is currently found In this respect, the sequence may be native to the host genome, but be rearranged with respect to other genetic sequences within the host sequence. For example, a regulatory sequence may be heterologous in that it is linked to a different coding sequence relative to the native regulatory sequence.

Obtaining: When used in conjunction with a transgenic plant cell or transgenic plant, obtaining means either transforming a non-transgenic plant cell or plant to create the transgenic plant cell or plant, or planting transgenic plant seed to produce the transgenic plant cell or plant. Such a transgenic plant seed may be from an $R_0$ transgenic plant or may be from a progeny of any generation thereof that inherits a given transgenic sequence from a starting transgenic parent plant.

Promoter: A recognition site on a DNA sequence or group of DNA sequences that provides an expression control element for a structural gene and to which RNA polymerase specifically binds and initiates RNA synthesis (transcription) of that gene.

$R_0$ transgenic plant: A plant that has been genetically transformed or has been regenerated from a plant cell or cells that have been genetically transformed.

Regeneration: The process of growing a plant from a plant cell (e.g., plant protoplast, callus or explant).

Selected DNA: A DNA segment which one desires to introduce or has introduced into a plant genome by genetic transformation.

Transformation construct: A chimeric DNA molecule which is designed for introduction into a host genome by genetic transformation. Preferred transformation constructs will comprise all of the genetic elements necessary to direct the expression of one or more exogenous genes. In particular embodiments of the instant invention, it may be desirable to introduce a transformation construct into a host cell in the form of an expression cassette.

Transformed cell: A cell the DNA complement of which has been altered by the introduction of an exogenous DNA molecule into that cell.

Transgene: A segment of DNA which has been incorporated into a host genome or is capable of autonomous replication in a host cell and is capable of causing the expression of one or more coding sequences. Exemplary transgenes will provide the host cell, or plants regenerated therefrom, with a novel phenotype relative to the corresponding non-transformed cell or plant. Transgenes may be directly introduced into a plant by genetic transformation, or may be inherited from a plant of any previous generation which was transformed with the DNA segment.

Transgenic plant: A plant or progeny plant of any subsequent generation derived therefrom, wherein the DNA of the plant or progeny thereof contains an introduced exogenous DNA segment not naturally present in a non-transgenic plant of the same strain. The transgenic plant may additionally contain sequences which are native to the plant being transformed, but wherein the "exogenous" gene has been altered in order to alter the level or pattern of expression of the gene, for example, by use of one or more heterologous regulatory or other elements.

Vector: A DNA molecule designed for transformation into a host cell. Some vectors may be capable of replication in a host cell. A plasmid is an exemplary vector, as are expression cassettes isolated therefrom.

VI. Examples

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

EXAMPLE 1

Cloning and Expression Pattern of a Purple Acid Phosphatase Gene from *M. truncatula*

Figure 2:
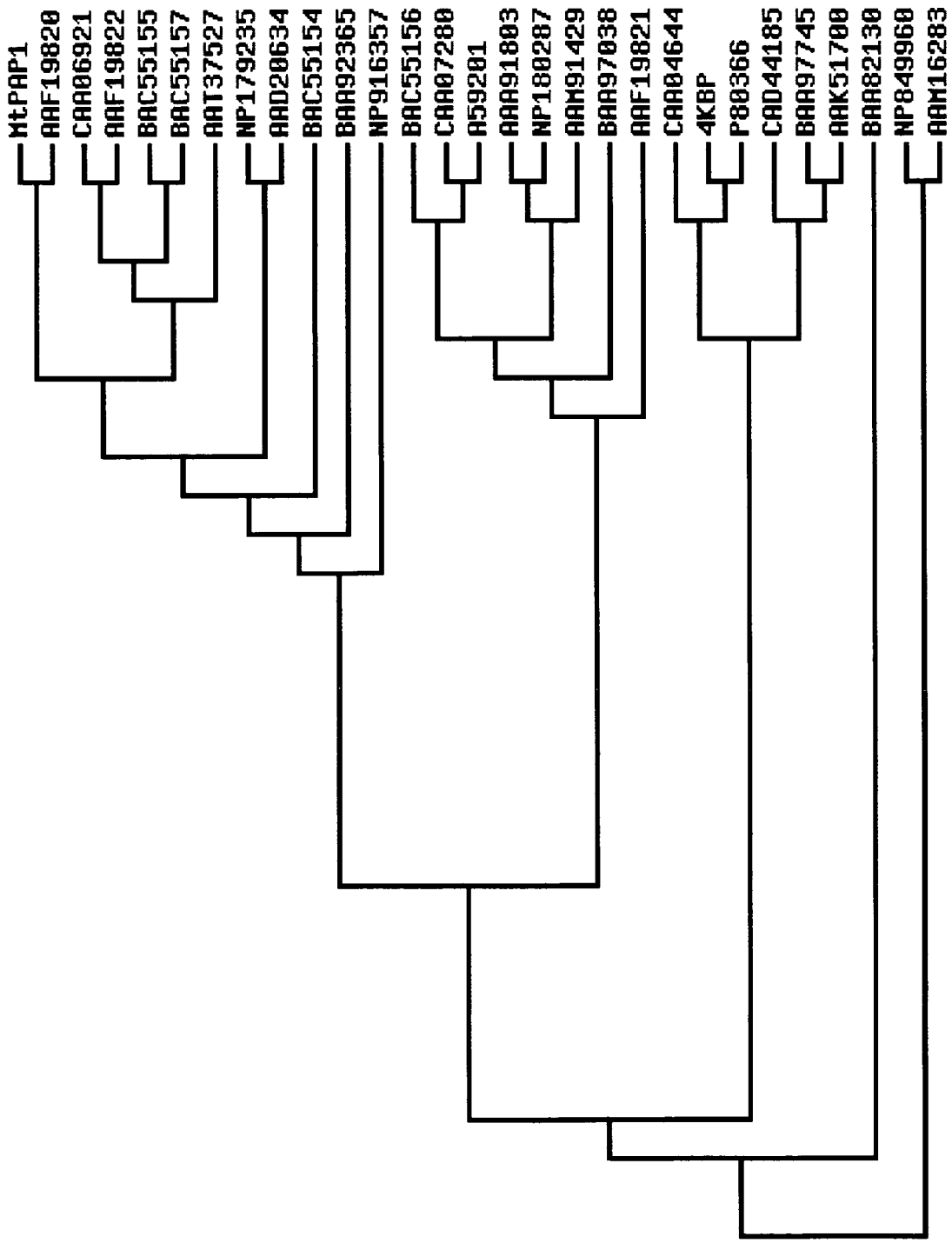
FIG. 2. Phylogenetic tree analysis of MtPAP1 with other purple acid phosphatases from different plant species. The sequences in the figure were selected based on Blast results of MtPAP1 in the NCBI GenBank. AAF19820 (*Glycine max* PAP precursor), CAA06921 (*Ipomoea batatas* PAP), AAF19822 (*Ipomoea batatas* PAP precursor), BAC55155 (*Nicotiana tabacum* PAP), BAC55157 (*Nicotiana tabacum* PAP), AAT37527 (*Solanum tuberosum* PAP2), NP179235 (*Arabidopsis thaliana* PAP10), AAD20634 (*Anchusa officinalis* PAP precursor), BAC55154 (*Nicotiana tabacum* PAP), BAA92365 (*Spirodela punctata* PAP), NP916357 (*Oryza sativa* putative PAP), BAC55156 (*Nicotiana tabacum* PAP), CAA07280 (*Ipomoea batatas* PAP), A59201 (*Ipomoea batatas* PAP3), AAA91803 (*Arabidopsis thaliana* secreted PAP precursor), NP 180287 (*Arabidopsis thaliana* iron(III)-zinc (II) PAP 12), AAM91429 (*Arabidopsis thaliana* At2g27190), BAA97038 (*Tagetes patula* APase precursor), AAF19821 (*Ipomoea batatas* PAP precursor), CAA04644 (*Phaseolus vulgaris* PAP precursor), P80366 (*Phaseolus vulgaris* Iron (III)-zinc(II) PAP), CAD44185 (*Lupinus luteus*), BAA97745 (*Lupinus albus* secretory APase precursor), AAK51700 (*Lupinus albus* secreted APase), BAA82130 (*Lupinus albus* APase), NP849960 (*Arabidopsis thaliana* PAP10), AAM16283 (*Arabidopsis thaliana* truncated putative PAP) (SEQ ID NOs:25-51) and 4 KBP (*Phaseolus vulgaris* PAP).

A full-length cDNA clone was obtained by screening a phosphate-starved cDNA library of *M. truncatula* roots with the coding region of a purple acid phosphatase gene from *Arabidopsis*. The cDNA was 1698 bp in length with an open reading frame (ORF) of 1398 bp predicted to encode an N-terminal signal peptide of 23 amino acids and a mature APase with a molecular mass of 51.3 kDa (SEQ ID NO:1). The predicted protein contains five conserved blocks of residues, GDLG/GDLSY/GNHE/VLMH/GHVH (SEQ ID NOs: 3-7), that are commonly found in plant PAPs (Schenk et al., 2000; Li et al., 2002). The five conserved residue blocks surround a complete set of seven invariant amino acid residues (in bold) involved in the ligation of the dimetal nuclear center in known PAPs. Sequence alignment showed that the predicted protein shares high levels of identity (78.5-85.8%) with purple acid phosphatases of *Glycine max, Ipomoea batatas, Nicotiana tabacum* and *Arabidopsis thaliana* (FIG. 2). The results indicate that the isolated cDNA likely represents a purple acid phosphatase gene and the cDNA was thus designated MtPAP1.

The expression pattern of the MtPAP1 gene was analyzed by northern hybridization with RNA isolated from different tissues of *M. truncatula*. Under high-Pi (2 mM) growth conditions, MtPAP1 transcripts were detected mainly in leaves, with only weak hybridization to root RNA (FIG. 1A). However, under low-Pi (10 μM) conditions, the transcript level was reduced in leaves and increased in roots, with the strongest hybridization signal detected in roots (FIG. 1A). Transcript levels were low in stems under both high and low Pi conditions (FIG. 1A).

Southern hybridization analysis indicated that two copies of MtPAP1 exist in the *M. truncatula* genome (FIG. 1B).

EXAMPLE 2

Localization of MtPAP1-GFP Fusion Protein in Transgenic *Arabidopsis*

Analysis of the MtPAP1 signal sequence by TargetP (Emanuelsson et al., 2000) revealed a secretion pathway score of 0.898, indicating that the protein was likely to be secreted to the outside of the cell. To analyze the localization of the APase protein in plant cells, a chimeric gene including the native signal peptide sequence (sp) and an in-frame fusion of MtPAP1 and GFP under the control of CaMV35S promoter was constructed (35S::sp-MtPAP1-GFP). For comparison, a second gene construct was made by replacing the native signal sequence with the patatin signal sequence from potato (35S::sp'-MtPAP1-GFP). The patatin signal peptide was shown to be necessary for the secretion of active recombinant phytase from soybean cell suspension cultures (Li et al., 1997).

In transgenic *Arabidopsis* plants carrying either 35S::sp-MtPAP1-GFP or 35S::sp'-MtPAP1-GFP, green fluorescence was mainly detected in apoplast of the cells (FIGS. 2A and 2B), indicating a similar accumulation pattern of the fusion protein for the two gene constructs, whereas in transgenics carrying the control gene construct CaMV35S::GFP, a free distribution of green fluorescence was observed in the cells (FIG. 2C).

EXAMPLE 3

Activity and Secretion of APases in Transgenic *Arabidopsis* Expressing MtPAP1

In order to express the gene exclusively in roots and particularly in the epidermis and root hairs, a root-specific promoter from phosphate transporter 1 (MtPT1) (Chiou et al., 2001) was used to drive the expression of MtPAP1. Two chimeric genes were constructed with the MtPT1 promoter, one containing the native signal sequence (MtPT1::sp-MtPAP1, FIG. 4A), the other having the patatin signal sequence (MtPT1::sp'-MtPAP1, FIG. 4B). The third chimeric gene was constructed with the CaMV35S promoter, containing the patatin signal sequence (CaMV35S::sp'-MtPAP1, FIG. 4C).

Transgenic *Arabidopsis* plants were produced with the three chimeric gene constructs following the floral dip method (Clough and Bent, 1998). T3 homozygous lines were obtained for each gene construct and were used for analysis. After germination and growth on normal MS medium (Murashige and Skoog, 1962) for one week, the transgenics were transferred to a modified MS medium containing phytate as the sole source of P and grown for two weeks. Nine lines from each gene construct were analyzed regarding their MtPAP1 transcript levels and acid phosphatase activities in roots (FIG. 3).

Three MtPT1::sp-MtPAP1 lines (1, 6, 8), five MtPT1::sp'-MtPAP1 lines (1', 4', 5', 6', 7∝and four CaMV35S::sp'-MtPAP1 lines (2", 5", 8", 9") showed relatively high levels of transgene expression (FIGS. 3A, 3C and 3E). Because of the background APase activities in plant cells, when APase activity was analyzed using whole-root extracts, the high expressors of the three gene constructs showed only 8.4% to 42.2% increase in APase activity compared with the empty vector control (FIG. 6). In contrast, when APase activity was measured in root apoplast extracts, the high expressors showed 4.6- to 9.9-fold higher enzyme activities than that of the control plant (FIGS. 3B, 3D and 3F). The increases in root apoplast APase activity of the high expressors were 4.6- to 7.9-fold for MtPT1::sp-MtPAP1 (FIG. 3B), 5.2- to 9.2-fold for MtPT1::sp'-MtPAP1 (FIG. 3D) and 7.2- to 9.9-fold for CaMV35S::sp'-MtPAP1 (FIG. 3F). The average APase activity of the high expressors of MtPT1::sp-MtPAP1 was 13.4% lower than that of MtPT1::sp'-MtPAP1, while the average value of the high expressors of MtPT1::sp'-MtPAP1 and CaMV35S::sp'-MtPAP1 were similar and had no significant difference. A clear positive relationship was observed between transcript levels and enzyme activities. For all the three gene constructs, plants with high transcript levels had high APase activities, whereas plants with very low or non-detectable mRNA had similar APase activities as the control plant (FIG. 3).

Staining for APase activity in roots and root exudates of the high expressors of the three gene constructs all showed much darker and more intense purple color than that of the control (FIG. 4), confirming that transgenic expression of MtPAP1 led to much more accumulation of APase in roots and its secretion into the rhizosphere.

In transgenic and control plants grown in liquid MS medium with phytate as the sole P source the intermediates of phytate (InsP6) degradation were analyzed by HPLC. The exudates from control roots only degraded InsP6 at a very low levels (FIG. 5A), whereas root exudates from the high expressors degraded InsP6 rapidly with a concomitant accumulation of InsP5, InsP4, InsP3, InsP2, InsP1 and Ins (FIG. 5B). Most of the InsP6 was degraded after growing transgenics for 24 h in liquid medium (FIG. 5B). Thus, the APase secreted from the transgenic roots was able to degrade phytate in the liquid medium.

EXAMPLE 4

Plant Growth, Biomass Production and P Accumulation of Transgenic *Arabidopsis* Plants The growth of the high expressors was much better than that of the control plants when phytate was used as the sole P source (FIG. 4, FIG. 8). Because of the stored P in seeds, the fresh weight and dry weight of all the young transgenic plants (15 d) were almost the same as the control plants (FIG. 6). The difference between the transgenics and the control became evident with plant development. At day 30, fresh weight and dry weight of most of the transgenic lines doubled that of control (FIG. 6). At day 45, fresh weight and dry weight of most of the transgenic lines tripled that of control (FIG. 6). Transgenic lines of the three gene constructs showed similar trends, although the average value of the MtPT1::sp-MtPAP1 lines was slightly lower than that of the MtPT1::sp'-MtPAP1 and CaMV35S::sp'-MtPAP1 lines.

Similar to the biomass production, no difference was observed between transgenics and control regarding P concentration and total P content at day 15 (FIG. 7). At day 30 and day 45, most of the transgenic lines showed higher P concentrations, and drastic increases in total P contents were found for all the transgenic lines (FIG. 7). Again, similar trends were observed for the three gene constructs tested.

EXAMPLE 5

Isolation of Acid Phosphatase cDNA Sequences from *M. truncatula*

The *Medicago truncatula* purple acid phosphatase cDNA was identified by a screening approach employing an *Arabidopsis* purple acid phosphatase gene as the query (U48448). Excised and cloned cDNA inserts were obtained using the ExAssist helper phage with SOLR strain, as described by the manufacturer (Stratagene, La Jolla, Calif.). Positive clones were sequenced and the full-length cDNA clone selected was designated MtPAP1. The Genbank accession number of MtPAP1 is AY804257.

EXAMPLE 6

Gene Constructs and Transformation of *Arabidopsis*

Three gene constructs were used for GFP subcellular localization analysis. The CaMV35S::GFP construct was created by inserting a HindIII-EcoRI fragment from the CaMV35S-sGFP(S65T)-nos plasmid (Chiu et al., 1996) into HindIII-EcoRI digested pCAMBIA3300. To make the MtPAP1-GFP fusion construct with the native signal peptide sequence (CaMV35S::sp-MtPAP1-GFP), the ORF of MtPAP1 was PCR amplified with forward primer 5'-TGTCGACATGGGTTTTCTTCATAG-3'(SalI) (SEQ ID NO:8) and reverse primer 5'-TCCATGGGATGGGAAACATGAGTTGT-3' (NcoI) (SEQ ID NO:9), digested with SalI and NcoI, and inserted into SalI-NcoI digested CaMV35S:GFP without codon shift. To make the MtPAP1-GFP fusion construct with the patatin signal sequence (CaMV35S::sp'-MtPAP1-GFP), the patatin signal sequence was obtained by amplifying potato DNA with forward primer 5'-AGTCGACATGGCAACTACTAAAT-3' (SalI) (SEQ ID NO:10) and reverse primer 5'-AGTCGACCGTAGCACATGTTGAA-3' (SalI) (SEQ ID NO:11); an SalI restriction site was created on both sides of the amplified patatin sequence. In the mean time, an MtPAP1 fragment without the native signal sequence was obtained by PCR amplification using forward primer 5'-TGTCGACGGCAGAACTAGTACTTT-3' (SalI) (SEQ ID NO:12) and reverse primer 5'-TCCATGGGATGGGAAA-CATGAGTTGT-3' (NcoI) (SEQ ID NO:13); SalI and NcoI restriction sites were created in the amplified fragment. The SalI digested patatin signal fragment, the SalI-NcoI digested MtPAP fragment, and the SalI-NcoI partial digested CaMV35S::GFP were ligated. Correct ligation product (CaMV35S::sp'-MtPAP1-GFP) was confirmed by DNA sequencing.

Three chimeric genes were constructed for the overexpression of MtPAP1. A root-specific promoter, MtPT1, was isolated from the phosphate transporter 1 gene (Chiou et al., 2001). An intermediate gene construct, MtPT1-GUS, was made by replacing the CaMV35S promoter of pCAMBIA3301 with the MtPT1 promoter. The MtPT1 promoter was amplified from *M. truncatula* DNA by using forward primer 5'-AGGATCCTATTATATGCATGGGCTG-3' (BamHI) (SEQ ID NO:14) and reverse primer 5'-TCCATGGACTGAATTTGTTACCTAGT-3' (NcoI) (SEQ ID NO:15), digested with BamHI and NcoI, and inserted into BamHI-NcoI digested pCAMBIA3301 to create the intermediate construct MtPT1-GUS. To construct MtPT1::sp-MtPAP1, the ORF of MtPAP1 was PCR amplified with forward primer 5'-GCCATGGGTTTTCTTCATAGTTTA-3' (NcoI) (SEQ ID NO:16) and reverse primer 5'-AGGTTACCATTGTTGGTGGTATTGA-3' (BstEII) (SEQ ID NO:17), digested by NcoI and BstEII, and ligated with NcoI-BstEII digested MtPT1-GUS. To construct MtPT1-sp'-MtPAP1, NcoI restriction sites were created in the patatin signal sequence by amplification of potato DNA with primers 5'-TCCATGGCAACTAC-TAAATCTTTT-3' (forward) (SEQ ID NO:18) and 5'-TCCATGGGCGTAGCACATGTTGAACT-3' (reverse) (SEQ ID NO:19); the MTPAP1 fragment without the native signal sequence, but with newly created NcoI and BstEII restriction sites, was obtained by PCR amplification using forward primer 5'-TCCATGGGCAGAACTAGTACTTT-3' (NcoI) (SEQ ID NO:20) and reverse primer 5'-AGGTTACCATTGT-TGGTGGTATTGA-3' (BstEII) (SEQ ID NO:21). MtPT1-sp'-MtPAP1 was created by ligating NcoI digested patatin signal sequence, NcoI-BstEII digested MtPAP1 fragment and NcoI-BstEII digested MtPT1-GUS. The third MtPAP1 construct, CaMV35S-sp'-MtPAP1, was created by ligating NcoI digested patatin signal sequence, NcoI-BstEII digested MtPAP1 fragment and NcoI-BstEII digested pCAMBIA3301.

DNA of the above binary vectors was transferred into the *Agrobacterium tumefaciens* strain C58 by the freeze-thaw method (Chen et al., 1994). Transgenic *Arabidopsis* (ecotype Columbia) plants were produced following the floral dip method (Clough and Bent, 1998). T3 homozygous lines were obtained after selfing and used for analysis.

EXAMPLE 7

Growth Conditions

*M. truncatula* was grown under conditions as described by Liu et al. (1998). Briefly, 10-day-old seedlings were grown on sterilized fine sand and fertilized with half-strength Hoagland's solution containing either 10 µM or 2 mM $KH_2PO_4$ three times a week. After three weeks, roots, leaves and stems were harvested, frozen in liquid nitrogen and stored at −80° C. for RNA isolation.

Seeds of transgenic *Arabidopsis* lines were surface sterilized with bleach and germinated on normal MS (Murashige and Skoog, 1962) agar medium containing 2% sucrose for eight days. The seedlings were then transferred to a modified MS medium containing 133 µM phytate (equivalent to 0.8 mM Pi) as the sole source of P. The seedlings and plants were grown at 24° C. in fluorescent light (240 µE $m^{-2}$ $s^{-1}$) at a photoperiod of 16 hours in the growth room. Roots of the 22-day-old (8 days on normal MS medium, two weeks on phytate containing MS medium) transgenic *Arabidopsis* lines were collected and used for RNA isolation and APase activity analysis. P concentration, fresh weight and dry weight were measured from 15-, 30- and 45-day-old plants.

EXAMPLE 8

Blot Hybridization Analysis

For Southern hybridization, twenty µg of *M. truncatula* genomic DNA was first digested with restriction enzymes EcoRI, HindIII and XhoI and separated through a 0.8% agarose gel. DNA gel blotting was carried out following standard protocols (Sambrook et al., 1989). To avoid cross hybridization of MtPAP1 with other similar sequences, the 3' untranslated region (UTR) was [$^{32}$P] dCTP labeled and used as the probe. Southern hybridizations were performed following the QuikHyb Hybridization protocols (Stratagene, La Jolla, Calif.).

For northern blot hybridization analysis total RNA was first isolated using TRI reagent (Molecular Research Center, Inc., Cincinnati, Ohio) and RNA gel blotting carried out according to standard protocols (Sambrook et al., 1989). For analyzing transcript levels in different organs of *M. truncatula*, the 3' UTR of MtPAP1 was used as the probe. For analyzing expression levels of transgenes in *Arabidopsis* root, the coding sequence of MtPAP1 was used as the probe. Northern hybridizations were performed using [$^{32}$P] dCTP labeled probes following the QuikHyb Hybridization protocols (Stratagene, La Jolla, Calif.).

EXAMPLE 9

Measurement of APase Activities and Staining of APase in Roots

Root samples were collected from 22-day-old plants and ground into powder with liquid nitrogen. APase activity was measured spectrophotometrically following the method described by Gilbert et al. (1999). For the measurement of APase activity in root apoplast, apoplast sap obtained from roots by the centrifugation method (Yu et al., 1999) was immediately used for APase activity assay (Gilbert et al., 1999)

Root staining for phosphomonoesterase activity was done by adding staining solution to petri dishes with transgenic plants. The staining solution consisted of 50 mM tri-sodium-citrate (TSC) buffer (pH 5.5), 37.5 mM α-naphthyl phosphate and 2.7 mM Fast Red TR (Zimmermann et al., 2003). The roots were stained for 2 hours at room temperature and then photographed.

EXAMPLE 10

HPLC Analysis of the Hydrolysis of Phytate by Root Exudates

Seeds of the control and transgenic lines were sowed on normal MS agar medium. Ten-day-old seedlings were transferred to wells containing liquid modified MS medium in which Pi was replaced by phytate. The wells were fixed in a rack and the seedlings were grown for another seven days in a shaker. The roots were then harvested, washed in deionized water and incubated in 50 ml of 5 mM maleate buffer, pH 5.5, containing 2 mM $CaCl_2$, 0.01% protease inhibitor cocktail (Sigma) and 2 mM InsP6 from rice (Sigma). One milliliter was sampled at time points 0, 12 and 24 h, and the enzyme was inactivated by the addition of 0.5 ml 15% TCA. Samples were analyzed by HPLC following standard procedures. The sum of InsP2, InsP1 and Ins was calculated as the difference between total initial InsP6 and the sum of measured values for the other InsP forms (Zimmermann et al., 2003).

EXAMPLE 11

Free P Assay and Total Phosphate Assay

For the free P assay, plant samples were ground to a fine powder in liquid nitrogen and suspended in 1% glacial acetic acid. After incubation at 42° C. for 30 min, the samples were centrifuged, and the supernatant was assayed at $OD_{820}$ as described by Ames (1966).

For the total phosphate assay, samples were collected to glass tubes containing 0.03 ml $Mg(NO_3)_2$ solution. The samples were dried and ashed by shaking over strong flames. After adding HCl and assay mix, total phosphate was determined by calorimetric assay at $OD_{820}$ (Ames, 1966).

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The references listed below are incorporated herein by reference to the extent that they supplement, explain, provide a background for, or teach methodology, techniques, and/or compositions employed herein.

U.S. Pat. No. 4,535,060
U.S. Pat. No. 5,302,523
U.S. Pat. No. 5,322,783
U.S. Pat. No. 5,384,253
U.S. Pat. No. 5,464,765
U.S. Pat. No. 5,508,184
U.S. Pat. No. 5,538,877
U.S. Pat. No. 5,538,880
U.S. Pat. No. 5,545,818
U.S. Pat. No. 5,550,318
U.S. Pat. No. 5,563,055
U.S. Pat. No. 5,591,616
U.S. Pat. No. 5,610,042
Abdullah et al., *Biotechnology*, 4:1087, 1986.
Abelson, *Science*, 283:2015, 1999.
Altschul et al., *J. Mol. Biol.*, 215:403-410, 1990.
Ames, In: *Methods in Enzymology*, Neufeld and Ginsburg (Eds.), Academic Press, NY, (8): 115-118, 1966.
Asmar et al., *Plant Soil*, 172:117-122, 1995.
Baldwin et al., *Plant Physiol.*, 125:728-737, 2001.
Bates, *Mol. Biotechnol.*, 2(2): 135-145, 1994.
Battraw and Hall, *Theor. App. Genet.*, 82(2):161-168, 1991.
Bevan et al., *Nucleic Acids Research*, 11(2):369-385, 1983.
Bhattacharjee et al., *J. Plant Bioch. Biotech.* 6, (2):69-73. 1997.
Bieleski, *Annu. Rev. Plant Physiol.*, 24:225-252, 1973.
Biocomputing: Informatics and Genome Projects, Smith (Ed.), Academic Press, NY, 1993.
Birren, et al., *Genome Analysis*, 1:543-559, 1997.
BLAST Manual, Altschul et al. (Eds.), NCBI NLM NIH, Bethesda, Md. 20894
Bower et al., *Plant J.*, 2:409-416. 1992.
Buising and Benbow, *Mol Gen Genet*, 243(1):71-81. 1994.
Callis et al., *Genes Dev.*, 1:1183-1200, 1987.
Carillo and Lipman, *Applied Math*, 48:1073, 1988.
Casa et al., *Proc. Natl. Acad. Sci. USA*, 90(23):11212-11216, 1993.
Chandler et al., *Plant Cell*, 1:1175-1183, 1989.
Chen et al., Biotechniques, 16:664-670, 1994.
Chiou et al., *Plant J.*, 25:281-293, 2001.
Chiu et al., *Curr. Biol.*, 6:325-330, 1996.
Chu et al., *Scientia Sinica*, 18:659-668, 1975.
Clough and Bent, *Plant J.*, 16:735-743, 1998.

Computational Molecular Biology, Lesk (Ed.), Oxford University Press, NY, 1988.
Computer Analysis of Sequence Data, Part I, Griffin and Griffin (Eds.), Humana Press, NJ, 1994.
Conkling et al., *Plant Physiol.*, 93:1203-1211, 1990.
Coulson, *Trends Biotech.*, 12:76-80, 1994.
Dalal, *Advances in Agronomy*, 29:83-117, 1977.
DE 3642 829
De Block et al., *EMBO J.*, 6(9):2513-2518, 1987.
De Block et al., *Plant Physiol.*, 91:694-701, 1989.
del Pozo et al., *Plant J.*, 19:579-589, 1999.
Dellaporta et al., In: *Chromosome Structure and Function: Impact of New Concepts*, 18th Stadler Genetics Symposium, 11:263-282, 1988.
Devereux et al., *Nucleic Acids Res.*, 12(1):387, 1984.
Downward, *BMJ*, 328(7450):1245-1248, 2004.
Duff et al., *Physiol. Plant.*, 90:791-800, 1994.
Ebert et al., *Proc. Natl. Acad. Sci. USA*, 84:5745-5749, 1987.
Emanuelsson et al., *J. Mol. Biol.*, 300:1005-1016, 2000.
EPA App. 154,204
Fire et al., *Nature*, 391(6669):806-811, 1998.
Fraley et al., *Bio/Technology*, 3:629-635, 1985.
Fromm et al., Nature, 319:791-793, 1986.
Gallie et al., *Plant Cell*, 1:301-311, 1989.
Gaston et al., *J. Environ. Qual.*, 32:1422-1429, 2003.
Gelvin et al., In: *Plant Molecular Biology Manual*, 1990.
Ghosh-Biswas et al., *J. Biotechnol.*, 32(1):1-10, 1994.
Gilbert et al., *Plant Cell Environ.*, 22:801-810, 1999.
Goldstein et al., *Plant Physiol.*, 87:711-715, 1988.
Goldstein et al., *Plant Physiol.*, 87:716-720, 1988.
Hagio et al., *Plant Cell Rep.*, 10(5):260-264, 1991.
Haran et al., *Plant Physiol.*, 124:615-626, 2000.
Haseloff et al., *Proc. Natl. Acad. Sci. USA*, 94(6):2122-2127, 1997.
He et al., *Plant Cell Reports*, 14 (2-3):192-196, 1994.
Helal, *Plant Soil*, 123:161-163, 1990.
Hensgens et al., *Plant Mol. Biol.*, 22(6):1101-1127, 1993.
Hentikoff and Hentikoff, *Proc. Natl. Acad. Sci USA*, 89:10915-10919, 1992.
Hiei et al., *Plant Mol. Biol.*, 35(1-2):205-218, 1997.
Hinchee et al., *BioTechnol.*, 6:915-922, 1988.
Hudspeth and Grula, *Plant Mol. Biol.*, 12:579-589, 1989.
Hunter et al., *J. Plant Nutr.*, 22:679-692, 1999.
Ikuta et al., *BioTechnol.*, 8:241-242, 1990.
Ishidia et al., *Nat. Biotechnol.*, 14(6):745-750, 1996.
Iyamuremye and Dick, *Advances in Agronomy*, 56:139-185, 1996.
Kaeppler et al., *Plant Cell Reports*, 9:415-418, 1990.
Kaeppler et al., *Theor. Appl. Genet.*, 84(5-6):560-566, 1992.
Katz et al., *J. Gen. Microbiol.*, 129:2703-2714, 1983.
Klee et al., *BioTechnology*, 3(7):637-642, 1985.
Knittel et al., *Plant Cell Reports*, 14(2-3):81-86, 1994.
Lawton et al., *Plant Mol. Biol.*, 9:315-324, 1987.
Lazzeri, *Methods Mol. Biol.*, 49:95-106, 1995.
Lehner et al., *Brief Funct. Genomic Proteomic.*, 3(1):68-83, 2004.
Li et al., *J. Biol. Chem.*, 277:27772-27781, 2002.
Li et al., *Plant Physiol.*, 114:1103-1111, 1997.
Liu et al., *Mol. Plant Microbe Interact.*, 11(1):14-22, 1998.
McCabe and Martinell, *BioTechnology*, 11(5):596-598, 1993.
McCormac et al., *Euphytica*, 99(1):17-25, 1998.
McLachlan, *Aust. J. Agric. Res.*, 31:441-448, 1980.
Mihaliak et al., *Meth. Plant Biochem.*, 9:261-279, 1993.
Miller et al., *Plant Physiol.*, 127:594-606, 2001.
Murakami et al., *Mol. Gen. Genet.*, 205:42-50, 1986.
Murashige and Skoog, *Physiol. Plant.*, 15:473-497, 1962.
Murashigeand Skoog, *Physiol. Plant.*, 15:473-497, 1962.
Nagatani et al., *Biotech. Tech.*, 11(7):471-473, 1997.
Needleman and Wunsch, *J. Mol. Biol.*, 48:443-453, 1970.
Odell et al., *Nature*, 313:810-812, 1985.
Ogawa et al., *Sci. Rep.*, 13:42-48, 1973.
Olah and Sherwood, *Phytopathology*, 61:65-69, 1971.
Omirulleh et al., *Plant Mol. Biol.*, 21(3):415-428, 1993.
Ow et al., *Science*, 234:856-859, 1986.
PCT Appln. WO 92/17598
PCT Appln. WO 94/09699
PCT Appln. WO 95/06128
PCT Appln. WO 97/04103
PCT Appln. WO 97/41228
Pote et al., *J. Environ. Qual.*, 32:2392-2398, 2003.
Potrykus et al., *Mol. Gen. Genet.*, 199:183-188, 1985.
Prasher et al., *Biochem. Biophys. Res. Commun.*, 126(3): 1259-1268, 1985.
Raghothama, *Annu. Rev. Plant Physiol. Plant Mol. Biol.*, 50:665-693, 1999.
Reichel et al., *Proc. Natl. Acad. Sci. USA*, 93(12):5888-5893, 1996.
Richardson et al., *Plant J.*, 25:641-649, 2001.
Ritala et al., *Plant Mol. Biol.*, 24(2):317-325, 1994.
Rogers et al., *Methods Enzymol.*, 153:253-277, 1987.
Rommens et al., *Plant Physiol.*, 135:421-431, 2004.
Sambrook et al., In: *Molecular cloning: a laboratory manual*, 2nd Ed., Cold Spring Harbor Laboratory, NY, 1989.
Schenk et al., *Gene*, 250:117-125, 2000.
Schumacher et al., *Plant Cell Rep.*, 6:410-413, 1987.
Sequence Analysis in Molecular Biology, von Heinje (Ed.), Academic Press, NY, 1987.
Sequence Analysis Primer, Gribskov and Devereux (Eds.), Stockton Press, NY, 1991.
Sheen et al., *Plant J.*, 8(5):777-784, 1995.
Singsit et al., *Transgenic Res.*, 6(2):169-176, 1997.
Stalker et al., *Science*, 242:419-422, 1988.
Sullivan et al., *Mol. Gen. Genet.*, 215(3):431-440, 1989.
Sutcliffe, *Proc. Natl. Acad. Sci. USA*, 75:3737-3741, 1978.
Tarafdar et al., *Biol. Fertil. Soils*, 5:308-312, 1988.
Thomas et al., *Plant Sci.* 69:189-198, 1990.
Thompson et al., *EMBO J.*, 6(9):2519-2523, 1987.
Thompson et al., *Euphytica*, 85(1-3):75-80, 1995.
Tian et al., *Plant Cell Rep.*, 16:267-271, 1997.
Tingay et al., *Plant J.*, 11(6):1369-1376, 1997.
Tomes et al., *Plant. Mol. Biol.* 14(2):261-268, 1990.
Tomscha et al., *Plant Physiol.*, 135:334-345, 2004.
Torbet et al., *Crop Science*, 38(1):226-231, 1998.
Torbet et al., *Plant Cell Reports*, 14(10):635-640, 1995.
Toriyama et al., *Theor Appl. Genet.*, 73:16, 1986.
Tsukada et al., *Plant Cell Physiol.*, 30(4)599-604, 1989.
Twell et al., *Plant Physiol.*, 91:1270-1274, 1989.
Van Eck et al., *Plant Cell Reports*, 14(5):299-304, 1995.
Vance et al., *New Phytol.*, 157:423-447, 2003.
Vasil et al., *Plant Physiol.*, 91:1575-1579, 1989.
Vogel et al., *Arch. Biochem. Biophys.*, 401:164-172, 2002.
Von Uexkull and Mutert, *Plant Soil*, 171:1-15, 1995.
Walker et al., *Proc. Natl. Acad. Sci. USA*, 84:6624-6628, 1987.
Wang et al., *Molec. Cell. Biol.*, 12(8):3399-3406, 1992.
Wasaki et al., *Plant Soil*, 248:129-136, 2003.
Wasaki et al., *Soil Sci. Plant Nutr.*, 45:439-449, 1999.
Wasaki et al., *Soil Sci. Plant Nutr.*, 45:937-945, 1999.
Wasaki et al., *Soil Sci. Plant Nutr.*, 46:427-437, 2000.
Whitelaw, *Advances in Agronomy*, 69:99-151, 2000.
Yamada et al., *Plant Cell Rep.*, 4:85, 1986.

Yan et al., *Plant Physiol.*, 125:1901-1911, 2001.
Yang and Russell, *Proc. Natl. Acad. Sci. USA*, 87:4144-4148, 1990.
Yu et al. *New Phytol.*, 143:299-304, 1999.
Zheng and Edwards, *J. Gen. Virol*, 71:1865-1868, 1990.
Zimmermann et al. *Plant Biotechnol. J.*, 1:353-360, 2003.
Zukowsky et al., *Proc. Natl. Acad. Sci. USA*, 80:1101-1105, 1983.

What is claimed is:

1. An isolated nucleic acid sequence encoding plant acid phosphatase, wherein the nucleic acid sequence is selected from the group consisting of: (a) a nucleic acid sequence encoding the polypeptide of SEQ ID NO:2; (b) a nucleic acid sequence comprising the sequence of SEQ ID NO: 1; (c) a nucleic acid sequence which hybridizes to SEQ ID NO: 1 under wash conditions of 0.15 M NaCl and 70° C. for 10 minutes; (d) a nucleic acid sequence encoding a polypeptide comprising at least 95% sequence identity over the full length of the polypeptide sequence of SEQ ID NO:2; and (e) a nucleic acid sequence fully complementary to the nucleic acid sequence of (a), (b), (c) or (d).

2. The isolated nucleic acid of claim 1, wherein the nucleic acid is defined as encoding the polypeptide of SEQ ID NO:2.

3. The isolated nucleic acid of claim 1, wherein the nucleic acid is defined as comprising the nucleic acid sequence of SEQ ID NO:1.

4. A recombinant vector comprising the isolated nucleic acid sequence of claim 1 operably linked to a heterologous promoter.

5. The recombinant vector of claim 4, further comprising at least one additional sequence chosen from the group consisting of: a regulatory sequence, a selectable marker, a leader sequence and a terminator.

6. The recombinant vector of claim 5, wherein the additional sequence is a heterologous sequence.

7. The recombinant vector of claim 4, wherein the promoter is a tissue-specific promoter.

8. The recombinant vector of claim 4, wherein the promoter is a root-specific promoter.

9. The recombinant vector of claim 4, defined as an isolated expression cassette.

10. A transgenic plant transformed with the recombinant vector of claim 4.

11. The transgenic plant of claim 10, further defined as a monocotyledonous plant.

12. The transgenic plant of claim 10, further defined as a dicotyledonous plant.

13. The transgenic plant of claim 10, further defined as a legume.

14. The transgenic plant of claim 10, further defined as an $R_0$ transgenic plant.

15. The transgenic plant of claim 10, further defined as a progeny plant of any generation of an $R_0$ transgenic plant, wherein the transgenic plant has the nucleic acid sequence from the $R_0$ transgenic plant.

16. A transgenic seed of the transgenic plant of claim 10, wherein the seed comprises the nucleic acid sequence.

17. A host cell transformed with the recombinant vector of claim 4.

18. The host cell of claim 17, wherein said host cell is a plant cell.

\* \* \* \* \*